(12) United States Patent
Yarbrough et al.

(10) Patent No.: US 8,889,156 B2
(45) Date of Patent: Nov. 18, 2014

(54) CALCIUM-BINDING AGENTS INDUCE HAIR GROWTH AND/OR NAIL GROWTH

(75) Inventors: Daniel K. Yarbrough, Los Angeles, CA (US); Xiaoyang Wu, Northridge, CA (US); Wenyuan Shi, Los Angeles, CA (US); Maxwell Anderson, Sequim, WA (US)

(73) Assignees: The Regents of the University of California, Oakland, CA (US); C3 Jian, Inc., Inglewood, CA (US)

( * ) Notice: Subject to any disclaimer, the term of this patent is extended or adjusted under 35 U.S.C. 154(b) by 906 days.

(21) Appl. No.: 12/700,163

(22) Filed: Feb. 4, 2010

(65) Prior Publication Data

US 2010/0239503 A1 Sep. 23, 2010

Related U.S. Application Data

(60) Provisional application No. 61/150,623, filed on Feb. 6, 2009.

(51) Int. Cl.
*A61K 9/00* (2006.01)
*A61K 8/64* (2006.01)
*A61Q 3/00* (2006.01)
*A61Q 7/00* (2006.01)

(52) U.S. Cl.
CPC ... *A61Q 3/00* (2013.01); *A61K 8/64* (2013.01); *A61Q 9/64* (2013.01); *A61Q 7/00* (2013.01)
USPC .......................................... 424/400

(58) Field of Classification Search
None
See application file for complete search history.

(56) References Cited

U.S. PATENT DOCUMENTS

| 6,492,326 | B1 * | 12/2002 | Robinson et al. | 514/18.6 |
|---|---|---|---|---|
| 6,673,900 | B2 | 1/2004 | Rowe | |
| 7,314,865 | B2 * | 1/2008 | Schacter et al. | 514/21.4 |
| 2003/0104979 | A1 | 6/2003 | Wei et al. | |
| 2004/0220094 | A1 | 11/2004 | Skinner | |

FOREIGN PATENT DOCUMENTS

| CA | 2489009 | | 11/2003 |
|---|---|---|---|
| CN | 101272801 | A | 9/2008 |
| JP | 2005239695 | | 9/2005 |
| WO | 9806844 | | 2/1998 |
| WO | WO99/60017 | | 11/1999 |
| WO | WO01/32878 | | 5/2001 |
| WO | 0197834 | | 12/2001 |
| WO | 2007038683 | | 4/2007 |
| WO | WO2007038683 | | 4/2007 |
| WO | WO 2007038683 | A2 * | 4/2007 |
| WO | 2007085846 | | 8/2007 |
| WO | 2008114082 | | 9/2008 |

OTHER PUBLICATIONS

Canadian Office Action dated Apr. 18, 2013, Application No. 2,622,915.
Hunter, G. K., et al., "Nucleation of hydroxyapatite by bone sialoprotein", Proc. Natl. Acad. Sci. USA, vol. 90, pp. 8562-8565, Sep. 1993.
George et al., "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process", The Journal of Biological Chemistry, vol. 271, No. 51, pp. 32869-32873, Dec. 20, 1996.
Veis et al., "Properties of the (DSS)n triplet repeat domain of rat dentin phosphophoryn", European Journal of Oral Sciences 1998, 106 (suppl 1): 234-238.
Extended European Search Report dated Mar. 4, 2013 for European Patent Application No. 10739132.8.
Chinese Office Action (with English translation) dated Dec. 19, 2012 for Chinese Patent Application No. 201080015906.0.
Chinese Office Action (with English translation) dated Jun. 17, 2014 for Chinese Patent Application No. 201080015906.0.

* cited by examiner

*Primary Examiner* — Paul Dickinson
(74) *Attorney, Agent, or Firm* — Gates & Cooper LLP

(57) ABSTRACT

This invention provides novel methods for inducing hair growth and/or inhibiting hair loss and/or inducing nail growth in a mammal. In various embodiments the methods involve administering, e.g., to a mammal in need thereof, a calcium-binding peptide and/or peptide-like moiety in an amount sufficient to induce hair growth and/or to inhibit hair loss. In certain embodiments the agent is topically and/or transdermally administered.

18 Claims, 11 Drawing Sheets

CALCIUM-BINDING AGENTS INDUCE HAIR GROWTH AND/OR NAIL GROWTH

CROSS-REFERENCES TO RELATED APPLICATIONS

This application claims benefit of and priority to U.S. Ser. No. 61/150,623, filed Feb. 6, 2009, which is incorporated herein by reference in its entirety for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The present invention is generally related to methods of promoting hair and/or nail growth in a mammal, and more particularly related to a novel use of calcium-binding peptides to promoting hair growth and/or to reduce hair loss and/or to induce or to increase the rate of nail growth.

BACKGROUND OF THE INVENTION

At present, effective methods for the treatment of androgenetic alopecia include oral and topical formulations of finasteride (PROPECIA®) or minoxidil (6-(1-piperidinyl)-2,4-pyrimidane-diamine 3-oxide, see, e.g., U.S. Pat. Nos. 3,382,247 and 3,644,363), and various surgical techniques for the autotransplantation of hair follicles from areas unaffected by hair loss or for the redistribution of follicles from within an area affected by hair loss. Due largely to the cost and/or invasiveness of these treatments, there is also a significant market for hair loss remedies whose effectiveness remains undemonstrated (see, e.g., Sawaya and Shapiro (2000), *Dermatologic Clinics* 18:47-61, and references therein). Female pattern hair loss can additionally be treated, with much lower rates of success, using antiandrogen therapy, cyproterone acetate, spironolactone, flutamide (see, e.g., Ross and Shapiro (2005), *Dermatologic Clinics* 23: 227-243). Beyond these, hair loss is most often addressed by concealment or by cosmetic treatment. Alopecia areata is an autoimmune condition that can be treated with immunomodulators and immunomodulatory treatments, such as psoralen/UVA therapy. Finasteride has also been used with widely varying results.

BRIEF SUMMARY OF THE INVENTION

In various embodiments this invention pertains to the discovery that calcium-biding peptides and/or other calcium-binding agents (e.g., as described herein) can induce hair regrowth in mammals and are believed to be useful to induce hair growth and/or to prevent hair loss in men or women (e.g., for baldness on the scalp for men (alopecia androgenetica), drug-induced alopecia, and the like).

In certain embodiments a calcium-binding moiety is provided, where the calcium-binding moiety is a polymer or concatamer comprising at least two, three, or four subunits of the Formula I shown herein (joined directly or via linker(s)) where at least two of the subunits are adjacent to each other and where subunits that are separated from each other by a moiety other than a subunit, are separated by a linkage having a persistence length greater than or equal to at least about 5 Å, 7 Å, 10 Å, or 14 Å where E, G, L, M, T, and X in Formula I are independently selected from the group consisting of carbon, nitrogen, oxygen, silicon, phosphorus, sulfur, boron, and selenium, in chemically compatible configuration; $R_3$, $R_3'$, $R_4$, $R_4'$, $R_6$, $R_6'$, $R_7$, $R_7'$, $R_9$, $R_9'$, $R_{10}$, $R_{10}'$, in Formula I are present or absent as required to satisfy the valence of the relevant backbone atom and, when present, are sterically unhindered moieties chemically compatible with E, G, L, M, T, and X; at least one of $R_2$ and $R_2'$ are independently selected from the group consisting of H, Cl, I, F, Br, or $CH_3$, and when $R_2$ or $R_2'$ are not H, Cl, I, F, Br, or $CH_3$ they are characterized by Formula XIX shown herein where atom Q of Formula XIX is selected from the group consisting of carbon, nitrogen, oxygen, silicon, phosphorus, sulfur, boron, and selenium, in any chemically reasonable configuration, with $R_2^d$ present or absent as required to satisfy the valence of atom Q; and where $R_2^a$ and $R_2^b$ are small, sterically unhindered groups; and either $R_2^d$ and/or $R_2^c$ are a negatively charged group, and when $R_2^c$ consists of a negatively charged moiety and $R_2^d$ is present, $R_2^d$ consists of a small sterically unhindered group such as a carbonyl oxygen or H, Cl, I, F, Br, or $CH_3$, and vice versa; and at least one of $R_5$ and $R_5'$ is occupied by a hydroxyl group positioned one center away from the backbone, and the other is a small, sterically unhindered group. In certain embodiments the moiety excludes peptides comprising the amino acid sequence $(X\text{-}Y\text{-}Z)_n$, where X is an amino acid selected from the group consisting of aspartic acid (Asp), glutamic acid (Glu), asparagine (Asn), alanine (Ala) and glutamine (Gln); and Y and Z are amino acids independently selected from the group consisting of alanine (Ala), serine (Ser), threonine (Thr), phosphoserine (pSer), phosphothreonine (pThr), and their derivatives; and n ranges from 1 to 100. In certain embodiments the calcium-binding moiety has the structure of Formula XXXVII as shown therein, where $R_1$ and $R_{11}$ are independently present or absent and when present are selected from the group consisting of a solid substrate or an effector; and n ranges from 2, 3, 4, 5, 6, 7, 8, 9, 10, 11, 12, 13, 14, 15, 16, 17, 18, 19, or 20 to 60, 70, 80, 90, or 100. In certain embodiments $R_1$ and/or $R_{11}$, when present comprise an effector independently selected from the group consisting of a detectable label, an affinity tag, a pharmaceutical, a pharmaceutical carrier, and an antimicrobial peptide. In certain embodiments the detectable label is selected from the group consisting of a radioactive label, a fluorescent label, a colorimetric label, a radio-opaque label, a luminescent label, a bioluminescent label, and a spin label. In certain embodiments $R_1$ and/or $R_{11}$, when present comprise an effector selected from the group consisting of a peptide, a protein, a carbohydrate, a nucleic acid, a lipid, an organic compound, an inorganic compound, and an organometallic compound. In certain embodiments $R_1$ and/or $R_{11}$, when present comprise an effector that is an anticancer or antimicrobial compound. In certain embodiments the effector comprises an antimicrobial peptide is linked to calcium-binding moiety via an amino acid linker sequence. In certain embodiments at least 2, 3, 4, 6, 7, 8, 9, 10, 11, or 12 subunits are present.

In certain embodiments the moiety consists of or comprises a domain characterized by a formula selected from the group consisting of $S^1—S^2\text{-}L^1\text{-}S^3—S^4$, and $S^1—S^2\text{-}L^1\text{-}S^3\text{-}L^2\text{-}S^4$ where $S^1$, $S^2$, $S^3$, and $S^4$ are independently selected subunits of Formula I; and $L^1$ and $L^2$ are independently selected linkers (e.g., as shown in Table 3). In certain embodiments the moiety is a peptide and $L^1$ and/or $L^2$, when present are independently selected peptide linkers at least 1, 2, 3, 4, 5, 6, 7, 8, 9, 10, 11, 12, 13, 14, 15, or 16 amino acids in length. In certain embodiments the moiety is a peptide and $L^1$ and/or $L^2$, when present are independently selected peptide linkers that range in length from about 2 amino acids to about 50 amino acids. In certain embodiments $L^1$ and/or $L^2$, when present comprise a peptide linker independently selected from the peptide linkers in Table 3. In certain embodiments $L^1$ and/or $L^2$, when present comprise a nonpeptide linker independently selected from the nonpeptide linkers in Table 3.

In certain embodiments $R_2^a$ and/or $R_2^b$, when present are independently selected from the group consisting of H, Cl, I, F, Br, and $CH_3$. In certain embodiments either $R_2^c$ or $R_2^d$ are selected from the group consisting of $SO_4^{2-}$, $PO_4^{2-}$, and a carboxylate oxygen. In certain embodiments $R_2^c$ is a negatively charged moiety and $R_2^d$ is present and selected from the group consisting of H, Cl, I, F, Br, and $CH_3$, or $R_2^d$ is a negatively charged moiety and $R_2^d$ is present and selected from the group consisting of H, Cl, I, F, Br, and $CH_3$. In certain embodiments $R_2$ and/or $R_2'$ are independently selected from the group consisting of structures according to Formulas XX-XXIV as shown herein. In various embodiments one or more of $R_3$, $R_3'$, $R_4$, $R_4'$, $R_6$, $R_6'$, $R_7$, $R_7'$, $R_9$, $R_9'$, $R_{10}$, and $R_{10}'$ are independently selected from the group consisting of —OH, —$CH_3$, —$NH_2$, —$SiH_3$, —SH, —SH, —$BH_2$, H, I, Cl, Br, F, ethyl, carbonyl, and a secondary amine group. In certain embodiments one or more of $R_3$, $R_3'$, $R_4$, $R_4'$, $R_6$, $R_6'$, $R_7$, $R_7'$, $R_9$, $R_9'$, $R_{10}$, and $R_{10}'$ are independently selected from the group consisting of structures according to Formulas XXV-XXVII as shown herein. In certain embodiments $R^5$ has a structure according to Formula XVIII as shown herein where $R_5'$ is selected from the group consisting of carbon, nitrogen, oxygen, silicon, phosphorus, sulfur, boron, and selenium, in a chemically compatible configuration; and $R_5^a$, $R_5^b$ are independently selected small sterically unhindered groups. In certain embodiments $R_5^a$ and $R_5^b$ are independently selected from the group consisting of H, Cl, Br, I, F, CH3, and OH.

In certain embodiments the E-G, L-M, and T-X bonds of Formulas I or XXXVII have significant double bond character, either as direct double bonds or as part of an extended conjugated orbital system (e.g., the E-G, L-M, and/or T-X bonds are selected from the group consisting of structures according to Formulas II-XII as shown herein). In certain embodiments the E-G, L-M, and/or T-X bonds are structurally constrained or aromatic linkages e.g., the E-G, L-M, and/or T-X bonds are independently selected from the group consisting of structures according to Formulas XIII-XVIII as shown herein). In certain embodiments the moiety comprises a backbone selected from the group consisting of a backbone comprising peptide bonds, a polyethyleneglycol (PEG) backbone, an alkane backbone, an ethylene bridged backbone, and an ester backbone. In various embodiments the moiety is not phosphorylated. In certain embodiments the moiety is in a pharmaceutically acceptable excipient (optionally formulated as a unit dosage formulation). In certain embodiments the moiety is formulated for an application mode selected from the group consisting of oral administration, topical administration, nasal administration, pulmonary administration, inhalation, subdermal administration, systemic administration, surgical administration, subdermal depot administration, and rectal administration.

Methods are also provided for inducing hair growth or inhibiting hair loss and/or inducing nail growth in a mammal. The methods typically involve comprising administering to the mammal a calcium-binding moiety as described above (and below herein) and/or a calcium-binding peptide (as described herein), e.g., comprising one or more peptide domains the domain(s) comprising the sequence $(X-Y-Z)_n$, where X is an amino acid selected from the group consisting of aspartic acid, glutamic acid, asparagine, alanine and glutamine or a conservative substitution thereof, Y and Z are amino acids independently selected from alanine, serine, threonine, phosphoserine, and phosphothreonine, or conservative substitutions thereof, and n is a number from 1, 2, 3, 4, 5, 6, 7, 8, 9, 10, 11, 12, 13, 14, 15, 16, 17, 18, 19, or 20 to 30, 40, 50, 60, 70, 80, 90, or 100; where when more than one of the domains is present the domains can be the same or different; and where the calcium-binding peptide moiety binds calcium phosphate; where the calcium-binding moiety and/or calcium-binding peptide moiety is administered in an amount sufficient to induce hair growth and/or to inhibit hair loss, and/or to induce nail growth in the mammal. In certain embodiments the mammal is a non-human mammal (e.g., feline, canine, equine, bovine, urcine, lagomorph, non-human primate) or a human. In certain embodiments the calcium-binding moiety and/or the calcium-binding peptide is topically administered.

In certain embodiments the method comprises inducing hair growth or inhibiting hair loss (e.g., in a human diagnosed with a condition selected from the group consisting of alopecia areata, androgenetic alopecia, pharmaceutically induced alopecia, and radiation-induced alopecia). In certain embodiments the administering comprises administering the calcium-binding moiety and/or the calcium-binding peptide to region of the scalp, eyebrow, mustache (upper lip), chest, and the like (i.e., to a region where hair growth is desired). In certain embodiments the administering comprises administering the calcium-binding moiety and/or the calcium-binding peptide as a component of a formulation selected from the group consisting of a shampoo, a hair conditioner, a hair detangler, a hair coloring agent, a hair growth tonic, cream, gel, or salve.

In certain embodiments the method comprises inducing nail growth. In certain embodiments the administering comprises administering the calcium-binding moiety and/or the calcium-binding peptide to a region selected from the group consisting of a nail, a nail bed, a cuticle, the coronet area of a hoof, the base of a horn. In certain embodiments the administering comprises administering the calcium-binding moiety and/or the calcium-binding peptide as a component of a formulation selected from the group consisting of a nail polish, a nail strengthener, a hoof balm, a varnish, a hoof or nail glue, a sealant, a cream, a lotion, a foot bath, a hoof bath, and the like.

In various embodiments of these methods, the calcium-binding moiety or calcium-binding peptide is a calcium-binding peptide. In certain embodiments the calcium-binding peptide moiety comprises two or more of the domains joined by a non-peptide linker. In certain embodiments peptide comprises the sequence $(X-Y-Z)_n$, where X is an amino acid selected from the group consisting of aspartic acid, glutamic acid, asparagine, alanine and glutamine, or a conservative substitution therefor, Y and Z are amino acids selected from alanine, serine, threonine, phosphoserine, and phosphothreonine, and or conservative substitution(s) therefor, and n is a number from 1 to 100. In certain embodiments n is 2, 3, 4, 5, 6, 7, 8, 9, 10, 11, 12, 13, 14, 15, 16, 17, 18, 19, or 20. In various embodiments the peptide comprises the sequence $(X-Y-Z)_n$, where X is an amino acid selected from the group consisting of aspartic acid, glutamic acid, asparagine, alanine and glutamine, Y and Z are amino acids selected from alanine, serine, threonine, phosphoserine, and phosphothreonine, and n is a number from 1 to 100, or from 2 to 50, or from 3 to 30, or from 4 to 20, 15, 12, 11, 10, 9, 8, 6, or 6. In various embodiments the peptide or peptide domains are a D peptide or a beta peptide or have a PEG or other non-peptide backbone. In various embodiments the peptide or peptide domains comprise two or more copies of the amino acid sequence of a peptide subunit listed in Table 2. In certain embodiments the peptide or peptide domains have a length of about 3, 6, 9, 12, 15, 18, 21, 24, 27, or 30 to about 100 amino acids. In certain embodiments the peptide or peptide domains have a length of 3, 6, 9, 12, 15, 18, 21, 24, 27, or 30 amino acids. In certain embodiments n is a number from 2 to 8 (e.g., 2, 3, 4, 5, 6, 7, or 8). In certain embodiments X is aspartic acid or a conservative substitution therefor. In certain embodiments Y and Z are serine or conservative substitutions therefor. In certain embodiments the calcium-binding moiety or calcium-binding peptide comprises an "L" peptide, a "D" peptide, or a beta peptide selected from the group consisting of 4DSS (SEQ ID NO:31), 5DSS (SEQ ID NO:22), 6DSS (SEQ ID NO:32), 7DSS (SEQ ID NO:28), 8DSS (SEQ ID NO:33), 9DSS (SEQ ID NO:42), and 10DSS (SEQ ID NO:43). In certain embodiments the calcium-binding moiety or calcium-binding peptide is not phosphorylated. In certain embodiments the calcium-binding moiety or calcium-binding peptide bears a protecting group.

Formulations are provided for inducing hair growth or inhibiting hair loss and/or inducing nail growth in a mammal. The formulation typically comprise a calcium-binding moiety as described herein and/or a calcium-binding peptide as described herein, e.g., comprising one or more peptide domains the domain(s) comprising the sequence $(X-Y-Z)_n$, where X is an amino acid selected from the group consisting of aspartic acid, glutamic acid, asparagine, alanine and glutamine or a conservative substitution thereof, Y and Z are amino acids independently selected from alanine, serine, threonine, phosphoserine, and phosphothreonine, or conservative substitutions thereof, and n is a number from 1 to 100; where when more than one of the domains is present the domains can be the same or different; and where the calcium-binding peptide moiety binds calcium phosphate; and a carrier that permits the calcium-binding moiety and/or the calcium-binding peptide moiety to induce hair growth and/or inhibit hair loss and/or induce nail growth when topically applied to a mammal. In certain embodiments the carrier comprises an emulsion (e.g., a water-in-oil emulsion, an oil-in-water emulsion, etc.). In certain embodiments the calcium-binding moiety and/or the calcium-binding peptide is attached to a calcium phosphate nanoparticle or microparticle. In certain embodiments the nanoparticle or microparticle comprises a calcium phosphate selected from the group consisting of hydroxyapatite, beta tricalcium phosphate, octacalcium phosphate and dicalcium phosphate dehydrate. In various embodiments the nanoparticle or microparticle ranges in size from about 1 nm to about 1 μm. In various embodiments the formulation can be provided as a component of a product selected from the group consisting of a shampoo, a hair conditioner, a hair detangler, a hair coloring agent, a hair rinse, a hair growth tonic, a cream, a gel, and a salve. In various embodiments the formulation is provided as a component of a product selected from the group consisting of a nail polish, a nail strengthener, and a hoof balm.

In various embodiments of the formulation the calcium-binding moiety or calcium-binding peptide is a calcium-binding peptide. In certain embodiments the calcium-binding peptide moiety comprises two or more of the domains joined by a non-peptide linker. In certain embodiments peptide comprises the sequence $(X-Y-Z)_n$, where X is an amino acid selected from the group consisting of aspartic acid, glutamic acid, asparagine, alanine and glutamine, or a conservative substitution therefor, Y and Z are amino acids selected from alanine, serine, threonine, phosphoserine, and phosphothreonine, and or conservative substitution(s) therefor, and n is a number from 1 to 100. In certain embodiments n is 2, 3, 4, 5, 6, 7, 8, 9, 10, 11, 12, 13, 14, 15, 16, 17, 18, 19, or 20. In various embodiments the peptide comprises the sequence $(X-Y-Z)_n$, where X is an amino acid selected from the group consisting of aspartic acid, glutamic acid, asparagine, alanine and glutamine, Y and Z are amino acids selected from alanine, serine, threonine, phosphoserine, and phosphothreonine, and n is a number from 1 to 100, or from 2 to 50, or from 3 to 30, or from 4 to 20, 15, 12, 11, 10, 9, 8, 6, or 6. In various embodiments the peptide or peptide domains are a D peptide or a beta peptide or have a PEG or other non-peptide backbone. In various embodiments the peptide or peptide domains comprise two or more copies of the amino acid sequence of a peptide subunit listed in Table 2. In certain embodiments the peptide or peptide domains have a length of about 3, 6, 9, 12, 15, 18, 21, 24, 27, or 30 to about 100 amino acids. In certain embodiments the peptide or peptide domains have a length of 3, 6, 9, 12, 15, 18, 21, 24, 27, or 30 amino acids. In certain embodiments n is a number from 2 to 8 (e.g., 2, 3, 4, 5, 6, 7, or 8). In certain embodiments X is aspartic acid or a conservative substitution therefor. In certain embodiments Y and Z are serine or conservative substitutions therefor. In certain embodiments the calcium-binding moiety or calcium-binding peptide comprises an "L" peptide, a "D" peptide, or a beta peptide selected from the group consisting of 4DSS (SEQ ID NO:31), 5DSS (SEQ ID NO:22), 6DSS (SEQ ID NO:32), 7DSS (SEQ ID NO:28), 8DSS (SEQ ID NO:33), 9DSS (SEQ ID NO:43), and 10DSS (SEQ ID NO:44). In certain embodiments the calcium-binding moiety or calcium-binding peptide is not phosphorylated. In certain embodiments the calcium-binding moiety or calcium-binding peptide bears a protecting group.

Also provided is the use of calcium-binding moiety described herein and or a calcium-binding peptide, e.g., a peptide comprising one or more peptide domains the domain(s) comprising the sequence $(X-Y-Z)_n$, where X is an amino acid selected from the group consisting of aspartic acid, glutamic acid, asparagine, alanine and glutamine or a conservative substitution thereof, Y and Z are amino acids independently selected from alanine, serine, threonine, phosphoserine, and phosphothreonine, or conservative substitutions thereof, and n is a number from 1 to 100; where when more than one of the domains is present the domains can be the same or different; and where the calcium-binding peptide moiety binds calcium phosphate; in the manufacture of a medicament for inducing hair growth or inhibiting hair loss and/or inducing nail growth in a mammal. In various embodiments the mammal is a human or a non-human mammal. In various embodiments the calcium-binding moiety and/or the calcium-binding peptide is formulated for topical administration. In various embodiments the medicament is for inducing hair growth or inhibiting hair loss (e.g., for treatment of a human diagnosed with a condition selected from the group consisting of alopecia areata, androgenetic alopecia, pharmaceutically induced alopecia, and radiation-induced alopecia, and the like). In various embodiments the medicament comprises said calcium-binding moiety and/or said calcium-binding peptide as a component of a formulation selected from the group consisting of a shampoo, a hair conditioner, a hair detangler, a hair coloring agent, a hair growth tonic, cream, gel, or salve. In various embodiments the use comprises inducing nail growth. In certain embodiments the medicament comprises the calcium-binding moiety and/or the calcium-binding peptide formulated for application to a region selected from the group consisting of a nail, a nail bed, a cuticle, the coronet area of a hoof, the base of a horn. In certain embodiments the medicament comprises the calcium-binding moiety and/or the calcium-binding peptide as a component of a formulation selected from the group consisting of a nail polish, a nail strengthener, and a hoof balm. In certain embodiments the calcium-binding moiety or calcium-binding peptide is a calcium-binding peptide. In certain embodiments the calcium-binding peptide moiety comprises two or more of the domains joined by a non-peptide linker. In certain embodiments peptide comprises the sequence $(X-Y-Z)_n$, where X is an amino acid selected from the group consisting of aspartic acid, glutamic acid, asparagine, alanine and glutamine, or a conservative substitution therefor, Y and Z are amino acids selected from alanine, serine, threonine, phosphoserine, and phosphothreonine, and or conservative substitution(s) therefor, and n is a number from 1 to 100. In certain embodiments n is 2, 3, 4, 5, 6, 7, 8, 9, 10, 11, 12, 13, 14, 15, 16, 17, 18, 19, or 20. In various embodiments the peptide comprises the sequence $(X-Y-Z)_n$, where X is an amino acid selected from the group consisting of aspartic acid, glutamic acid, asparagine, alanine and glutamine, Y and Z are amino acids selected from alanine, serine, threonine, phosphoserine, and phosphothreonine, and n is a number from 1 to 100, or from 2 to 50, or from 3 to 30, or from 4 to 20, 15, 12, 11, 10, 9, 8, 6, or 6. In various embodiments the peptide or peptide domains are a D peptide or a beta peptide or have a PEG or other non-peptide backbone. In various embodiments the peptide or peptide domains comprise two or more copies of the amino acid sequence of a peptide subunit listed in Table 2. In certain embodiments the peptide or peptide domains have a length of about 3, 6, 9, 12, 15, 18, 21, 24, 27, or 30 to about 100 amino acids. In certain embodiments the peptide or peptide domains have a length of 3, 6, 9, 12, 15, 18, 21, 24, 27, or 30 amino acids. In certain embodiments n is a number from 2 to 8 (e.g., 2, 3, 4, 5, 6, 7, or 8). In certain embodiments X is aspartic acid or a conservative substitution therefor. In certain embodiments Y and Z are serine or conservative substitutions therefor. In certain embodiments the calcium-binding moiety or calcium-binding peptide comprises an "L" peptide, a "D" peptide, or a beta peptide selected from the group consisting of 4DSS (SEQ ID NO:31), 5DSS (SEQ ID NO:22), 6DSS (SEQ ID NO:32), 7DSS (SEQ ID NO:28), 8DSS (SEQ ID NO:33), 9DSS (SEQ ID NO:43), and 10DSS (SEQ ID NO:44). In certain embodiments the calcium-binding moiety or calcium-binding peptide is not phosphorylated. In certain embodiments the calcium-binding moiety or calcium-binding peptide bears a protecting group.

Methods are provided for treating a tooth defect and/or sensitivity characterized by tooth demineralization in a subject. The methods typically involve administering a composition comprising a calcium-binding moiety and/or a calcium-binding peptide as described hereinto the subject, where the administration results in tooth remineralization. In certain embodiments the calcium-binding moiety and/or a calcium-binding peptide is administered in conjunction with a desensitizing/remineralizing agent.

Methods are provided for treating a bone defect characterized by decreased bone density in a subject. The methods typically involve administering to the subject a composition comprising a calcium-binding moiety and/or a calcium binding peptide as described herein, where the administration results in an increase in bone density.

Methods are also provided for identifying a tooth defect characterized by tooth demineralization in a subject. The methods typically involve administering a composition comprising a calcium-binding moiety and/or calcium-binding peptide as described herein where the calcium-binding moieties and/or calcium-binding peptides in the composition are attached to (e.g., conjugated to) a detectable marker, and where the calcium-binding moieties preferentially bind demineralized tooth surfaces. The methods can further comprise detecting the detectable marker thereby identifying and/or localizing the defect.

In certain embodiments methods are provided for identifying a bone defect characterized by bone demineralization in a subject. The methods typically involve administering a composition comprising a calcium-binding moiety and/or calcium-binding peptide described herein to the subject, where the calcium-binding moieties in the composition are attached to (e.g., conjugated to) a detectable marker, and where the calcium-binding moieties preferentially bind to demineralized bone surfaces. The methods can further comprise detecting the detectable marker thereby identifying and/ or localizing the defect.

DEFINITIONS

The term "calcium-binding moiety" includes calcium-binding peptides as well as non-peptide calcium-binding molecules as described herein.

The term "peptide" as used herein refers to a polymer of amino acid residues typically ranging in length from 2 to about 50, 80, or about 100 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, phosphonamide, carbomate, hydroxylate, and the like (see, e.g., Spatola, (1983) *Chem. Biochem. Amino Acids and Proteins* 7: 267-357), where the amide is replaced with a saturated amine (see, e.g., Skiles et al., U.S. Pat. No. 4,496,542; and Kaltenbronn et al., (1990) Pp. 969-970 in Proc. 11th American Peptide Symposium, ESCOM Science Publishers, The Netherlands, and the like)).

The term "residue" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. These modified amino acids are illustrative and not intended to be limiting.

"DSS peptides", as used herein, include calcium-binding peptides comprising repeats of the Asp-Ser-Ser motif (e.g., as described in PCT Publication WO 2007/038683) and/or variations thereof, e.g., as described herein. In certain embodiments "DSS peptides" include calcium-binding peptides/proteins having multiple domains comprising repeats of the Asp-Ser-Ser motif and variations thereof "DSS" peptides can also comprise conjugates wherein two or more domains comprising repeats of the Asp-Ser-Ser motif and variations thereof are attached by non-peptide linkers thereby forming a multi-domain conjugate.

"β-peptides" comprise of "β amino acids", which have their amino group bonded to the β carbon rather than the α-carbon as in the 20 standard biological amino acids. The only commonly naturally occurring β amino acid is β-alanine.

Peptoids, or N-substituted glycines, are a specific subclass of peptidomimetics. They are closely related to their natural peptide counterparts, but differ chemically in that their side chains are appended to nitrogen atoms along the molecule's backbone, rather than to the α-carbons (as they are in natural amino acids).

The terms "conventional" and "natural" as applied to peptides herein refer to peptides, constructed only from the naturally-occurring amino acids: Ala, Cys, Asp, Glu, Glu, Phe, Gly, His, Ile, Lys, Leu, Met, Asn, Pro, Gln, Arg, Ser, Thr, Val, Trp, and Tyr. A compound of the invention "corresponds" to a natural peptide if it elicits a biological activity (e.g., Ca binding activity) similar to that of the naturally occurring peptide. The elicited activity may be the same as, greater than or less than that of the natural peptide. In general, a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. The following are illustrative, but non-limiting N-substituted glycine replacements: N-(1-methylprop-1-yl)glycine substituted for isoleucine (Ile), N-(prop-2-yl)glycine for valine (Val), N-benzylglycine for phenylanlaine (Phe), N-(2-hydroxyethyl)glycine for serine (Ser), and the like. In certain embodiments substitutions need not be "exact". Thus for example, in certain embodiments N-(2-hydroxyethyl)glycine may substitute for Ser, Thr, Cys, and/or Met; N-(2-methylprop-1-yl)glycine may substitute for Val, Leu, and/or Ile. In certain embodiments N-(2-hydroxyethyl)glycine can be used to substitute for Thr and Ser, despite the structural differences: the side chain in N-(2-hydroxyethyl)glycine is one methylene group longer than that of Ser, and differs from Thr in the site of hydroxy-substitution. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

Where an amino acid sequence is provided herein, L-, D-, or beta amino acid versions of the sequence are also contemplated as well as retro, inversion, and retro-inversion isoforms. In addition, conservative substitutions are contemplated. Non-protein backbones, such as PEG, alkane, ethylene bridged, ester backbones, and other backbones are also contemplated. Also fragments ranging in length from about 5, 6, 7, 8, 9, 10, 11, 12, 13, 14, 15, 16, 17, 18, 19, 20, 21, 22, 23, 24, or 25 amino acids up to the full length minus one amino acid of the peptide are contemplated where the fragment retains at least 50%, preferably at least 60% 70% or 80%, more preferably at least 90%, 95%, 98%, 99%, or at least 100% of the activity (e.g., binding specificity and/or avidity) of the corresponding unsubstituted peptide are contemplated.

In certain embodiments, conservative substitutions of the amino acids comprising any of the sequences described herein are contemplated. In various embodiments one, two, three, four, or five different residues are substituted. The term "conservative substitution" is used to reflect amino acid substitutions that do not substantially alter the activity (e.g., antimicrobial activity and/or specificity) of the molecule. Typically conservative amino acid substitutions involve substitution one amino acid for another amino acid with similar chemical properties (e.g. charge or hydrophobicity). Certain conservative substitutions include "analog substitutions" where a standard amino acid is replaced by a non-standard (e.g., rare, synthetic, etc) amino acid differing minimally from the parental residue. Amino acid analogs are considered to be derived synthetically from the standard amino acids without sufficient change to the structure of the parent, are isomers, or are metabolite precursors. Examples of such "analog substitutions include but are not limited to 1) Lys-Orn, 2) Leu-Norleucine, 3) Lys-Lys[TFA], 4) Phe-Phe[Gly], and 5) δ-amino butylglycine-ξ-amino hexylglycine, where Phe[gly] refers to phenylglycine (a Phe derivative with a H rather than $CH_3$ component in the R group), and Lys[TFA] refers to a Lys where a negatively charged ion (e.g., TFA) is attached to the amine R group. Other conservative substitutions include "functional substitutions" where the general chemistries of the two residues are similar, and can be sufficient to mimic or partially recover the function of the native peptide. Strong functional substitutions include, but are not limited to 1) Gly/Ala, 2) Arg/Lys, 3) Ser/Tyr/Thr, 4) Leu/Ile/Val, 5) Asp/Glu, 6) Gln/Asn, and 7) Phe/Trp/Tyr, while other functional substitutions include, but are not limited to 8) Gly/Ala/Pro, 9) Tyr/H is, 10) Arg/Lys/His, 11) Ser/Thr/Cys, 12) Leu/Ile/Val/Met, and 13) Met/Lys (special case under hydrophobic conditions). Various "broad conservative substations" include substitutions where amino acids replace other amino acids from the same biochemical or biophysical grouping. This is similarity at a basic level and stems from efforts to classify the original 20 natural amino acids. Such substitutions include 1) nonpolar side chains: Gly/Ala/Val/Leu/Ile/Met/Pro/Phe/Trp, and/or 2) uncharged polar side chains Ser/Thr/Asn/Gln/Tyr/Cys. In certain embodiments broad-level substitutions can also occur as paired substitutions. For example, Any hydrophilic neutral pair [Ser, Thr, Gln, Asn, Tyr, Cys]+[Ser, Thr, Gln, Asn, Tyr, Cys] can may be replaced by a charge-neutral charged pair [Arg, Lys, His]+[Asp, Glu]. The following six groups each contain amino acids that, in certain embodiments, are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W). Where amino acid sequences are disclosed herein, amino acid sequences comprising, one or more of the above-identified conservative substitutions are also contemplated.

In certain embodiments, peptides compromising at least 80%, preferably at least 85% or 90%, and more preferably at least 95% or 98% sequence identity with any of the sequences described herein (and preferably retain at least 50%, 60%, 70%, 80%, 90% 95%, 98% or 100% or more binding specificity and/or avidity of the unmodified peptide) are also contemplated. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides of this invention sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman (1981) *Adv. Appl. Math.* 2: 482, by the homology alignment algorithm of Needleman & Wunsch (1970) *J. Mol. Biol.* 48: 443, by the search for similarity method of Pearson & Lipman (1988) *Proc. Natl. Acad. Sci., USA*, 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

"Treating" or "treatment" of a condition as used herein may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "consisting essentially of" when used with respect to an calcium-binding peptide or other moiety as described herein, indicates that the peptide or other moiety encompassed by variants, analogues, or derivatives thereof possess substantially the same or greater binding activity and/or specificity and/or avidity as the referenced moiety.

The terms "isolated" "purified" or "biologically pure" refer to material which is substantially or essentially free from components that normally accompany it as found in its native state. In the case of a peptide, an isolated (naturally occurring) peptide is typically substantially free of components with which it is associated in the cell, tissue, or organism. The term isolated also indicates that the peptide is not present in a phage display, yeast display, or other peptide library.

The terms "coadministration" or "administration in conjunction with" when used in reference to the use of a calcium-binding peptide or calcium-binding moiety and another agent (e.g., desensitizing and/or remineralizing agent) indicates that calcium-binding peptide or calcium-binding moiety and other agent are administered so that there is at least some chronological overlap in the activity of the two agents. In sequential administration there may even be some substantial delay (e.g., minutes or even hours) between administration of the two agents as long as the delivery agent the activity of each is present in a manner that provides an increased/enhanced result.

In various embodiments the amino acid abbreviations shown in Table 1 are used herein.

TABLE 1

Amino acid abbreviations.

| Name | Abbreviation | |
|---|---|---|
| | 3 Letter | 1 Letter |
| Alanine | Ala | A |
| βAlanine (NH$_2$—CH$_2$—CH$_2$—COOH) | βAla | |
| Arginine | Arg | R |
| Asparagine | Asn | N |

TABLE 1-continued

Amino acid abbreviations.

| Name | Abbreviation | |
|---|---|---|
| | 3 Letter | 1 Letter |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| episilon-aminocaproic acid (NH$^2$—(CH$_2$)$_5$—COOH) | Ahx | J |
| 4-aminobutanoic acid (NH$_2$—(CH$_2$)$_3$—COOH) | gAbu | |
| tetrahydroisoquinoline-3-carboxylic acid | | O |
| Lys(N(epsilon)-trifluoroacetyl) | | K[TFA] |
| α-aminoisobutyric acid | Aib | B |

BRIEF DESCRIPTION OF THE DRAWINGS

FIG. 7A: Binding of (DSS)n-containing peptides of various lengths. FIGS. 7B and 7C: binding of sequence variants.

FIG. 12 FIG. 1: Comparison of peptide-treated (left 2 digits, labeled "A") and mock-treated (right 2 digits, labeled "P") nails on Day 19 of the experiment. Digits 1 and 2 were treated with (D)-DSS in AOT/isopropanol nanoemulsion every third day for 19 days. Significantly more growth is seen in these nails than in digits 3 and 4, which were mock-treated with PBS.

DETAILED DESCRIPTION OF THE INVENTION

Figure 1:
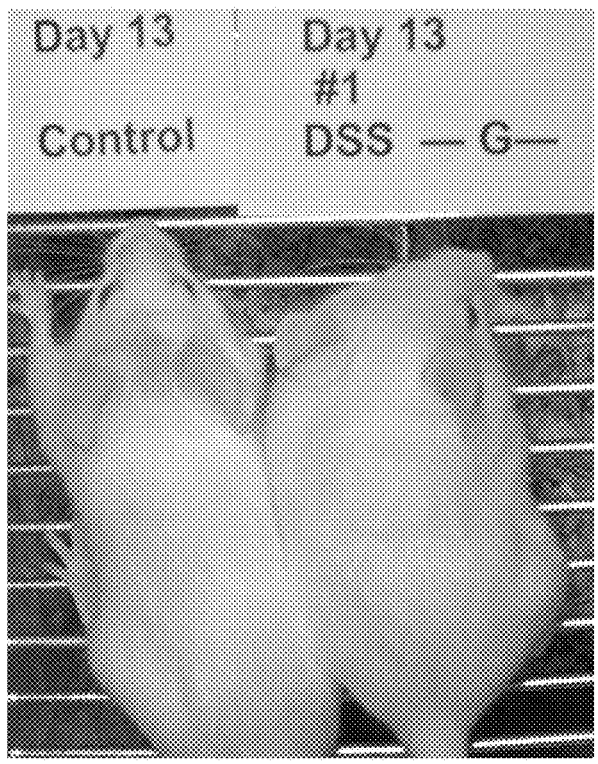
FIG. 1 shows DSS-Treated (below) and mock-treated (above) mice showing hair regrowth 13 days after shaving of the scalp.

In certain embodiments this invention pertains to the discovery that calcium-binding agents (e.g., peptides) described herein and in PCT Publication No: WO/2007/038683 induce hair growth and/or nail growth. It is believe the calcium-binding peptides and other calcium-binding moieties described herein can be used to restore hair and/or to inhibit hair loss in mammals and/or to induce nail growth and/or repair.

In certain embodiments the methods involve administering to a subject in need thereof one or more calcium-binding peptide(s) (e.g., as described herein and/or PCT application WO/2007/038683) and/or one or more of the other calcium-binding moieties described herein. In various embodiments the calcium-binding peptides and/or other moieties are provided in nondegradable forms. Illustrative nondegradable peptides can consist, for example, of peptides with all constituent amino acids in the (D) stereoisomer, peptides with modified backbones, peptidomimetics, or derivatized polymers such as peptide-conjugated linear polymers, copolymers, or dendrimers.

Administration of these peptides to sites of hair loss causes hair to grow at rates significantly greater than those normally observed. In certain embodiments this administration can be achieved by topical administration, dermal administration, intradermal administration, transdermal administration, subdermal administration, transdermal injection, transdermal iontophoresis (see U.S. Pat. No. 6,526,316), surgical implantation, or other means. In certain embodiments the compound is formulated with an acceptable carrier such as, for example, polymer reverse micelles, dimethylsulfoxide (DMSO), and the like for topical administration, or normal saline solution for injection or surgical implantation. In addition dendrimer forms themselves are likely to show enhanced transdermal penetration on topical application without the use of exotic carriers.

Advantages of this approach include, but are not limited to its efficacy, as currently existing approaches, including finasteride, provide only limited hair regrowth. The growth seen thus far using calcium-binding peptides in a mouse model is more significant than that reported for other compounds using other experimental systems. These methods have been tested in an animal model (mouse) and shown to be safe and effective in trials in this system.

In addition, the various calcium-binding moieties described herein can bind to surfaces in a tissue specific manner. In certain embodiments variants have been identified that bind specifically to dentin or enamel (see, e.g., FIG. 3), periodontal bone (human), long bones (rat), degraded mineral surfaces (caries, in the tooth model), and titanium (with a binding interface). Toxicity testing shows no acute toxicity, no organ damage and no antigenic response.

In various embodiments these constructs can be directed to 1) recruit calcium phosphate layers to pretreated tooth surfaces (see FIG. 3); 2) nucleate hydroxyapatite crystal formation on enamel, dentin, and abiotic surfaces; 3) provide targeted delivery of antimicrobial compounds to calcium-bearing microbial biofilms; 4) substantially increase the rate of healing in critical defects; 5) bind to Calcium Oxalate crystals; and 6) distinguish between Calcium Phosphate and Strontium Phosphate crystals. These uses are illustrative and not limiting.

In various embodiments the calcium-binding peptides and/or calcium-binding moieties described herein and/or chimeric constructs comprising these can be used to remineralize dental defects; diagnose bone and tooth defects, enhance osteointegration in dental and other osseous implants; enhance bone healing; treat osteomyelitis and osteoporosis; inhibit inappropriate mineralization; and target therapeutics to mineralized tissue defects or sites of inappropriate mineralization. These uses are illustrative and not limiting.

Calcium-Binding Agents.

Calcium-Binding Peptides ("DSS" Peptides).

In certain embodiments the calcium-binding agents include, but are not limited to calcium-binding peptides. Calcium-binding peptides are moieties that comprise or consist of one or more calcium-binding peptide domains (e.g., DSS peptide domains such as those described in PCT Publication WO 2007/038683 which is incorporated herein by reference for the calcium-binding peptides described herein). Where multiple calcium-binding peptide domains are present they can be chemically conjugated together or can be directly attached via, for example a peptide bond or joined, for example via a peptide linker to form multi-domain calcium-binding peptides.

In certain embodiments, a series of calcium-binding peptides made up of variations of the Asp-Ser-Ser motif ("DSS" peptides) are provided as well as moieties comprising multiple calcium-binding peptides. These "DSS" peptides have been shown to bind tightly and specifically to calcium phosphate surfaces. In addition, these peptides have been shown to recruit calcium phosphate to such surfaces and to serve as binding moieties for the attachment of fluorescent labels to calcified surfaces regardless of their phosphorylation state.

The peptides/peptide domains described herein, referred to generally as DSS peptides, can be composed of various numbers and/or combinations of a subunit; the three amino acid Asp-Ser-Ser motif of DPP or variations thereof. Examples of three amino acid repeats that may be utilized include, but are not limited to, Asp-Ser-Ser (DSS), Glu-Ser-Ser (ESS), Asp-Thr-Thr (DTT), Glu-Thr-Thr (ETT), Asn-Ser-Ser (NSS), Asn-Thr-Thr (NTT), Gln-Ser-Ser (QSS), Gln-Thr-Thr (QTT), and variations thereof. Alternatively or in addition to these repeat sequences, the peptides disclosed herein may include minor variations of these repeats, including but not limited to Asp-Ser-Thr (DST), Asp-Ala-Ala (DAA), or Ala-Ser-Thr (AST), and the like. In various embodiments one or more amino acid residues within a three amino acid repeat may be chemically modified. For example, in certain embodiments the peptides can contain one or more Ser or Thr residues in which a hydroxyl group has been modified by the addition of a phosphate group (pSer, pThr), etc. In various embodiments the peptides vary in length from three to greater than fifty or 100 amino acids. In certain embodiments other modified residues include, but are not limited to phosphorylated, sulfated, sulfonated, or acylated version of Ser, Thr, Gly, or Ala.

The binding affinity of the peptides disclosed herein for calcified surfaces cam be controlled by altering the composition and number of repeats. For example, inclusion of one or more Asp-Ser-Ser repeats will increase the binding affinity of the peptide, because this sequence exhibits the highest affinity of any of the repeats tested. The binding affinity of the peptide may also be increased by increasing the number of three amino acid repeats. Peptides containing more than six repeats generally exhibit greater binding affinity than those with fewer repeats. In certain embodiments, the peptides disclosed herein may have a binding affinity (KA) for hydroxyapatite of greater than 15,000 $M^{-1}$. In certain embodiments, this binding affinity may be greater than 50,000 $M^{-1}$, in other embodiments greater than 100,000 $M^{-1}$, in other embodiments greater than 200,000 $M^{-1}$, and in other embodiments greater than 300,000 $M^{-1}$.

In certain embodiments, the peptides can contain one or more additional amino acids that are not part of a three amino acid repeat sequence. For example, in certain embodiments, the repeat portion of the peptide may be fused to an amino acid sequence having an additional functionality, such as for example an antimicrobial peptide sequence such as 2c-4 (RWRWRWF, SEQ ID NO:1), PL135 (FHFHLHF, SEQ ID NO:2), b-34 (LKRF LKWF KRF, SEQ ID NO:3), and the like. In certain of these embodiments, the repeat portion of the peptide can be fused to the additional amino acid sequence via a linker sequence, such as for example a triglycine sequence.

In certain embodiments, the peptides disclosed herein comprise the subunit sequence $(X-Y-Z)_n$, wherein X is an amino acid selected from aspartic acid (Asp), glutamic acid (Glu), asparagine (Asn), alanine (Ala) and glutamine (Gln), Y and Z are amino acids selected from alanine (Ala), serine (Ser), threonine (Thr), phosphoserine (pSer), phosphothreonine (pThr), and their derivatives, and n is a number between 1 and 100, preferably ranging from about 2 to about 50 or 100, more preferably ranging from about 4 to about 20. In certain embodiments, n ranges from 1 to 15, in other embodiments, n ranges from 1 to 10, and in certain embodiments n ranges from 3 to 4, 6, or 8. In certain embodiments, n is 1, 2, 3, 4, 5, 6, 7, 8, 9, 10, 11, 12, 13, 14, 15, 16, 17, 18, 19, 20, 21, 22, 23, 24, or 25. Illustrative 3 amino acid "DSS" ("XYZ") subunits are shown in Table 2.

TABLE 2

Illustrative "DSS" (XYZ) subunits.

| X | Y | Z | X | Y | Z |
|---|---|---|---|---|---|
| Asp | Ala | Ala | Asn | Thr | pSer |
| Asp | Ala | Ser | Asn | Thr | pThr |
| Asp | Ala | Thr | Asn | pSer | Ala |
| Asp | Ala | pSer | Asn | pSer | Ser |
| Asp | Ala | pThr | Asn | pSer | Thr |

TABLE 2-continued

Illustrative "DSS" (XYZ) subunits.

| X | Y | Z | X | Y | Z |
|---|---|---|---|---|---|
| Asp | Ser | Ala | Asn | pSer | pSer |
| Asp | Ser | Ser | Asn | pSer | pThr |
| Asp | Ser | Thr | Asn | pThr | Ala |
| Asp | Ser | pSer | Asn | pThr | Ser |
| Asp | Ser | pThr | Asn | pThr | Thr |
| Asp | Thr | Ala | Asn | pThr | pSer |
| Asp | Thr | Ser | Asn | pThr | pThr |
| Asp | Thr | Thr | Ala | Ala | Ala |
| Asp | Thr | pSer | Ala | Ala | Ser |
| Asp | Thr | pThr | Ala | Ala | Thr |
| Asp | pSer | Ala | Ala | Ala | pSer |
| Asp | pSer | Ser | Ala | Ala | pThr |
| Asp | pSer | Thr | Ala | Ser | Ala |
| Asp | pSer | pSer | Ala | Ser | Ser |
| Asp | pSer | pThr | Ala | Ser | Thr |
| Asp | pThr | Ala | Ala | Ser | pSer |
| Asp | pThr | Ser | Ala | Ser | pThr |
| Asp | pThr | Thr | Ala | Thr | Ala |
| Asp | pThr | pSer | Ala | Thr | Ser |
| Asp | pThr | pThr | Ala | Thr | Thr |
| Glu | Ala | Ala | Ala | Thr | pSer |
| Glu | Ala | Ser | Ala | Thr | pThr |
| Glu | Ala | Thr | Ala | pSer | Ala |
| Glu | Ala | pSer | Ala | pSer | Ser |
| Glu | Ala | pThr | Ala | pSer | Thr |
| Glu | Ser | Ala | Ala | pSer | pSer |
| Glu | Ser | Ser | Ala | pSer | pThr |
| Glu | Ser | Thr | Ala | pThr | Ala |
| Glu | Ser | pSer | Ala | pThr | Ser |
| Glu | Ser | pThr | Ala | pThr | Thr |
| Glu | Thr | Ala | Ala | pThr | pSer |
| Glu | Thr | Ser | Ala | pThr | pThr |
| Glu | Thr | Thr | Gln | Ala | Ala |
| Glu | Thr | pSer | Gln | Ala | Ser |
| Glu | Thr | pThr | Gln | Ala | Thr |
| Glu | pSer | Ala | Gln | Ala | pSer |
| Glu | pSer | Ser | Gln | Ala | pThr |
| Glu | pSer | Thr | Gln | Ser | Ala |
| Glu | pSer | pSer | Gln | Ser | Ser |
| Glu | pSer | pThr | Gln | Ser | Thr |
| Glu | pThr | Ala | Gln | Ser | pSer |
| Glu | pThr | Ser | Gln | Ser | pThr |
| Glu | pThr | Thr | Gln | Thr | Ala |
| Glu | pThr | pSer | Gln | Thr | Ser |
| Glu | pThr | pThr | Gln | Thr | Thr |
| Asn | Ala | Ala | Gln | Thr | pSer |
| Asn | Ala | Ser | Gln | Thr | pThr |
| Asn | Ala | Thr | Gln | pSer | Ala |
| Asn | Ala | pSer | Gln | pSer | Ser |
| Asn | Ala | pThr | Gln | pSer | Thr |
| Asn | Ser | Ala | Gln | pSer | pSer |
| Asn | Ser | Ser | Gln | pSer | pThr |
| Asn | Ser | Thr | Gln | pThr | Ala |
| Asn | Ser | pSer | Gln | pThr | Ser |
| Asn | Ser | pThr | Gln | pThr | Thr |
| Asn | Thr | Ala | Gln | pThr | pSer |
| Asn | Thr | Ser | Gln | pThr | pThr |
| Asn | Thr | Thr | | | |

In various embodiments, conservative amino acid substitutions for each position (X, and/or Y, and/or Z) are contemplated.

The subunits can be repeated contiguously (e.g., 8DSS: DSS DSS DSS DSS DSS DSS DSS DSS, SEQ ID NO:33), or, in certain embodiments, one or more subunits can be interspersed with one or more other subunits (e.g., DSS NSS DSS NSS (SEQ ID NO:5), and the like), and/or with non-subunit sequences. In certain embodiments domains comprising one or more subunits (e.g., n=1, 2, 3, 4, 5, 6, 7, 8, 9, 10, 11, 12, 13, 14, 15, 16, 17, 18, 19, 20, 21, 22, 23, 24, 25, etc.) can be joined to each other to form calcium-binding agents comprising multiple calcium-binding domains. The domains can be joined to each directly, or via a chemical linker to form conjugates or they can be joined via a peptide linker(s) to form a multi-domain peptide/protein.

In certain embodiments, the multiple binding domain moiety comprises at least two domains, at least three domains, at least four domains, at least five domains, at least six domains or more. The Ca binding domains comprising such a construct can be the same or different As indicated above, various Ca-binding domains comprising such a construct can be joined directly to each other, or two, or more of such domains can be attached to each other via a linker. An illustrative, but non-limiting, list of suitable linkers is provided in Table 3.

TABLE 3

Illustrative peptide and non-peptide linkers for joining Ca binding domains and/or for joining a Ca binding moiety (e.g., peptide) to one or more effectors (e.g., AMPs, detectable labels, and the like).

| Linker | SEQ ID NO: |
|---|---|
| AAA | |
| SAT | |
| PYP | |
| ASA | |
| GGG | |
| SGG | |
| GGGG | 6 |
| GGGGG | 7 |
| GGSGGS | 8 |
| ASASA | 9 |
| PSGSP | 10 |
| PSPSP | 11 |
| ASASA | 12 |
| PSPSP | 13 |
| KKKK | 14 |
| RRRR | 15 |
| Gly$_4$Ser | 16 |
| (Gly$_4$Ser)$_2$ | 17 |
| (Gly$_4$Ser)$_3$ | 18 |
| (Gly$_4$Ser)$_4$ | 19 |
| (Gly$_4$Ser)$_5$ | 20 |
| (Gly$_4$Ser)$_6$ | 21 |
| 2-nitrobenzene or O-nitrobenzyl | |
| Nitropyridyl disulfide | |
| Dioleoylphosphatidylethanolamine (DOPE) | |
| S-acetylmercaptosuccinic acid | |
| 1,4,7,10-tetraazacyclododecane-1,4,7,10-tetracetic acid (DOTA) | |
| β-glucuronide and β-glucuronide variants | |
| Poly(alkylacrylic acid) | |
| Benzene-based linkers (for example: 2,5-Bis(hexyloxy)-1,4-bis[2,5-bis(hexyloxy)-4-formyl-phenylenevinylene]benzene) and like. | |
| Disulfide linkages | |
| Poly(amidoamine) or like dendrimers linking multiple target and killing peptides in one molecule | |
| Carbon nanotubes | |
| Hydrazone and hydrazone variant linkers | |
| PEG of any chain length | |
| Succinate, formate, acetate butyrate, other like organic acids | |
| Aldols, alcohols, or enols | |
| Peroxides | |
| Alkane or alkene groups of any chain length | |
| One or more porphyrin or dye molecules containing free amide and carboxylic acid groups | |
| One or more DNA or RNA nucleotides, including polyamine and polycarboxyl-containing variants | |
| Inulin, sucrose, glucose, or other single, di or polysaccharides | |
| Linoleic acid or other polyunsaturated fatty acids | |
| Variants of any of the above linkers containing halogen or thiol groups | |

(all amino-acid-based linkers could be L, D, β, PEG backbone, or other forms)

DSS-Like Compounds.

In certain embodiments more general DSS-like calcium-binding moieties are provided. Typically such DSS-like compounds are composed of monomers that are themselves at least 9 atoms long, with an acetic acid moiety or it's physicochemical equivalent attached to the 2nd atom, and a methanolic or hydroxymethyl moiety or its physicochemical equivalent attached to the 5th and 8th atoms. This monomer may be repeated any number of times and may be attached to any other moiety.

Even more generally, this represents a polymer or concatamer of subunits of the form shown below in Formula I:

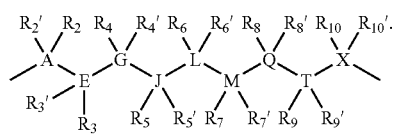

I

Typically, positions E, G, L, M, T, and X can each consist of carbon, nitrogen, oxygen, silicon, phosphorus, sulfur, boron, or selenium, in any chemically compatible combination or configuration, $R_3$, $R_3'$, $R_4$, $R_4'$, $R_6$, $R_6'$, $R_7$, $R_7'$, $R_9$, $R_9'$, $R_{10}$, $R_{10}'$, present or absent as required to satisfy the valence of the relevant backbone atom.

In various embodiments preferably, the E-G, and/or L-M, and/or T-X bonds have significant double bond character, either as direct double bonds or as part of an extended conjugated orbital system. Examples of systems of this nature include, but are not limited to structures according to Formulas II-XII:

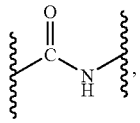

II

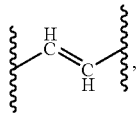

III

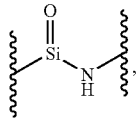

IV

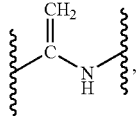

V

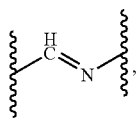

VI

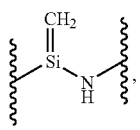

VII

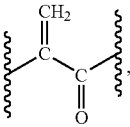

VIII

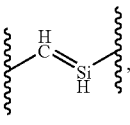

IX

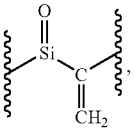

X

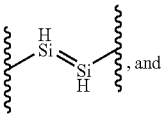

, and

XI

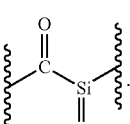

.

XII

In certain embodiments it is possible that structurally constrained or aromatic linkages might fill these positions. Such linkages include, but are not limited to structures according to Formulas XIII-XVIII:

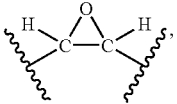

XIII

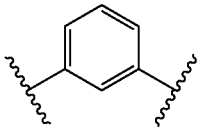

XIV

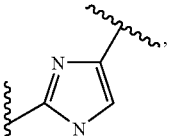

XV

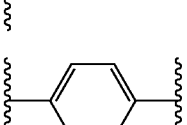

XVI

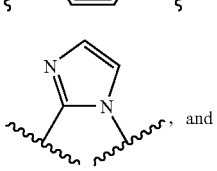

, and

XVII

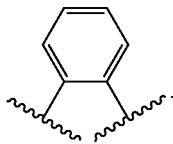

and the like.

Where $R_2$ consists of any moiety other than H, Cl, I, F, Br, or $CH_3$, $R_2'$ preferably is H, Cl, I, F, Br, or $CH_3$ and vice versa. In various embodiments moieties other than H, Cl, I, F, Br, or $CH_3$ in this position take the form of Formula XIX:

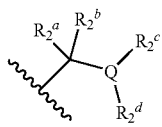

XIX where atom Q is carbon, nitrogen, oxygen, silicon, phosphorus, sulfur, boron, or selenium, in any chemically compatible configuration, with $R_2^d$ present or absent as required to satisfy the valence of atom Q, and where $R_2^a$ and $R_2^b$ each consist of a small, sterically unhindered group such as H, Cl, I, F, Br, or $CH_3$, and the like, and either $R_2^d$ or $R_2^c$ consist of a negatively charged group, such as sulfate ($SO_4^{2-}$), phosphate ($PO_4^{2-}$), or a carboxylate oxygen, and the like. In certain embodiments where $R_2^c$ is a negatively charged moiety and $R_2^d$ is present, $R_2^d$ is a small sterically unhindered group such as a carbonyl oxygen or H, Cl, I, F, Br, or $CH_3$, and the like, and vice versa.

Examples of moieties for $R_2$ or $R_2'$ include, but are not limited to structures according to Formulas XX-XXIV:

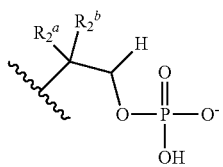

XX

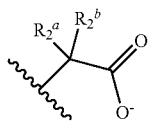

XXI

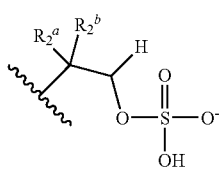

XXII

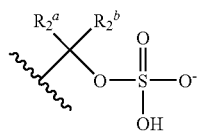

XXIII

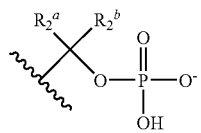

XXIV

In various embodiments $R_3$, $R_3'$, $R_4$, $R_4'$, $R_6$, $R_6'$, $R_7$, $R_7'$, $R_9$, $R_9'$, $R_{10}$, $R_{10}'$, can be any relatively unhindered moiety, as chemically appropriate given the identity of E, G, L, M, T, and X. Examples include, but are not limited to —OH, —$CH_3$, —$NH_2$, —$SiH_3$, —SH, —SH, —$BH_2$, H, I, Cl, Br, F, or ethyl, carbonyl, or secondary amine groups including, but not limited to structures according to Formulas XXV-XXVII:

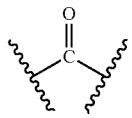

XXV

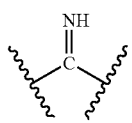

XXVI

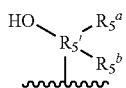

XXVII

In certain embodiments in the positions $R_5$ and $R_5'$, one position can be occupied by a hydroxyl group positioned one center away from the backbone, and the other occupied by a small, sterically unhindered group, preferably H, but also Cl, I, Br, F, —OH, —$CH_3$, —$NH_2$, —$SiH_3$, —SH, —SH, —$BH_2$, and the like are not prohibited.

An example of a hydroxyl group positioned one center away from the backbone is a structure according to Formula XVIII:

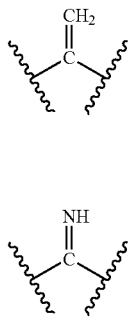

XVIII

Here, in various embodiments, $R_5'$ is carbon, nitrogen, oxygen, silicon, phosphorus, sulfur, boron, or selenium, in any chemically reasonable configuration and $R_5^a$, $R_5^b$ are independently selected small sterically unhindered groups (e.g., H, Cl, Br, I, F, $CH_3$, OH, etc.).

Specific compounds with suitable activity include but are not limited to: Compounds with a polyethyleneglycol (PEG) backbone including, but not limited to structures according to Formulas XXIX and XXX:

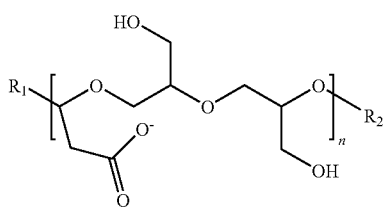

XXIX

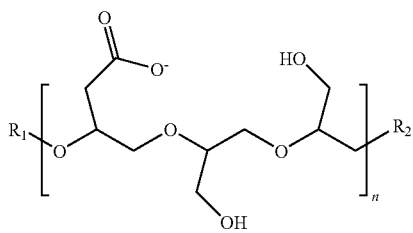

XXX

These structures are equivalent except where $R_1$ and $R_2$ impart directionality.

Compounds with an alkane backbone including, but not limited to structures according to Formulas XXXI and XXXII:

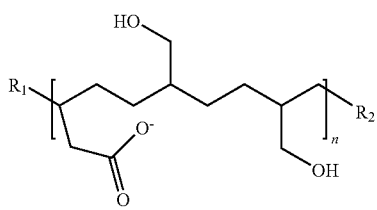

XXXI

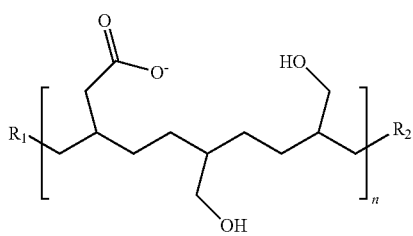

XXXII

These structures are equivalent except where $R_1$ and $R_2$ impart directionality.

Compounds with an ethylene bridged backbone including, but not limited to structures according to Formulas XXXIII and XXXIV:

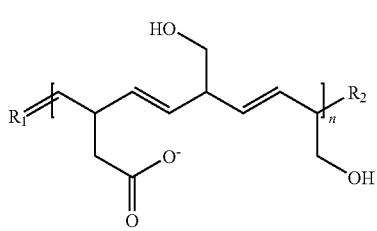

XXXIII

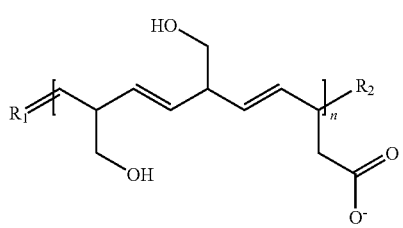

XXXIV

These structures are equivalent except where $R_1$ and $R_2$ impart directionality.

Compounds with an ester backbone including but not limited to backbones shown by the structures according to Formulas XXXV and XXXVI:

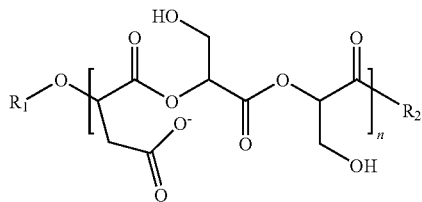

XXXV

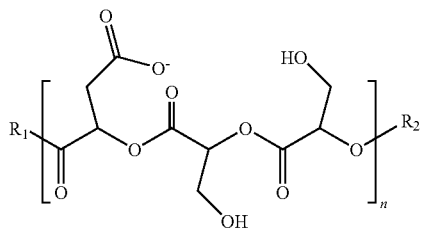

XXXVI

These structures are equivalent except where $R_1$ and $R_2$ impart directionality. Again it will be appreciated that concatamers comprising these subunits (and/or other subunits described herein) with or without intervening linkers are contemplated. Where one or more linkers separate subunits, in certain embodiments, the concatamer comprise at least 2, preferably at least 3, more preferably at least 4, still more preferably at least 5, 6, 7, 8, 9, 10, 11, 12, 13, 14, 15, 16, 17, 18, 19, 20 subunits. In various embodiments where subunits are separated by one or more linkers, at least two of the subunits are separated by a linker providing a persistence length equivalent to or greater than about 4 amino acids (e.g., about 14 Å or greater).

Additional compounds include compounds with a peptide backbone.

In various embodiments the subunits of the compounds described herein are adjacent to each other and the compound is a polymer of these subunits. In certain embodiments one or more linkers can separate the subunits. Typically, however, at least two subunits will be adjacent to each other in a calcium-binding moiety. Thus, for example, in certain illustrative embodiments, the calcium-binding moiety can comprise a structure of the form $S^1_w\text{-}S^2_x\text{-}L^1_y\text{-}S^3_z\text{-}S^4_m$, or $S^1_w\text{—}S^2_x\text{-}L^1\text{-}S^3_z\text{-}L^2\text{-}S^4_m$ where the "S" indicates a subunit as described herein, "L" indicates a linker (e.g., as shown in Table 3), and w, x, y, z, and m are range from 0 to 100, more preferably from about 4 to about 100 (e.g., as described above for "n"), most preferably 4, 5, 6, 7, 8, 9, 10, 11, 12, 13, 14, 15, 16, 17, 18, 19, 20, 21, 22, 23, 24, or 25. Typically when the subunits are not adjacent, they are separated by a linkage having a persistence length greater than or equal to at least one, two, or three amino acids, preferably greater than or equal to 4 amino acids.

In certain embodiments the moieties described herein can comprise regions represented by Formula XXXVII:

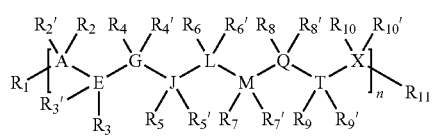

XXXVII where $R_1$ and $R_{11}$ are independently present or absent and when present are selected from the group consisting of a solid substrate (e.g., a surface, a particle, a nanoparticle, etc.) and/or an effector (e.g., as described herein), and n ranges from about 2, 3, or 4 up to about 100 (e.g., as described above). Various illustrative effectors include, but are not limited to detectable labels, drugs, drug carriers, antimicrobial peptides, and the like.

In various embodiments the agents described herein (e.g., the DSS-like moieties) expressly exclude one or more of the agents described in PCT Publication WO 2007/038683. Accordingly in certain embodiments, the formulas described herein expressly exclude excludes peptides comprising or consisting of the amino acid sequence $(X-Y-Z)_n$, where X is an amino acid selected from the group consisting of aspartic acid (Asp), glutamic acid (Glu), asparagine (Asn), alanine (Ala) and glutamine (Gln), and Y and Z are amino acids independently selected from the group consisting of alanine (Ala), serine (Ser), threonine (Thr), phosphoserine (pSer), phosphothreonine (pThr), and their derivatives; and n ranges from 1 to 100. In certain embodiments the formulas described herein expressly exclude one or more of the subunits shown in Table 2.

Protecting Groups.

While the various peptides described herein may be shown with no protecting groups, in certain embodiments they can bear one, two, three, four, or more protecting groups. In various embodiments, the protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus.

In various embodiments the addition of a protecting group, particularly to the carboxyl and in certain embodiments the amino terminus can improve the stability and/or efficacy of the peptide.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g., groups having the formula: $CH_3—(CH_2)_n—CO—$ where n ranges from about 1 to about 20, preferably from about 1 to about 16 or 18, more preferably from about 3 to about 13, and most preferably from about 3 to about 10.

In certain embodiments, the protecting groups include, but are not limited to alkyl chains as in fatty acids, propeonyl, formyl, and others. Particularly preferred carboxyl protecting groups include amides, esters, and ether-forming protecting groups. In one embodiment, an acetyl group is used to protect the amino terminus and/or an amino group is used to protect the carboxyl terminus (i.e., amidated carboxyl terminus). In certain embodiments blocking groups include alkyl groups of various lengths, e.g., groups having the formula: $CH_3—(CH_2)_n—CO—$ where n ranges from about 3 to about 20, preferably from about 3 to about 16, more preferably from about 3 to about 13, and most preferably from about 3 to about 10.

In certain embodiments, the acid group on the C-terminal can be blocked with an alcohol, aldehyde or ketone group and/or the N-terminal residue can have the natural amide group, or be blocked with an acyl, carboxylic acid, alcohol, aldehyde, or ketone group.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, xanthyl (Xan), trityl (Trt), 4-methyltrityl (Mtt), 4-methoxytrityl (Mmt), 4-methoxy-2,3,6-trimethyl-benzenesulphonyl (Mtr), mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), benzyloxy (BzlO), benzyl (Bzl), benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), cyclohexyloxy (cHxO), t-butoxymethyl (Bum), t-butoxy (tBuO), t-butyl (tBu), acetyl (Ac), and trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis*, 2nd ed., John Wiley & Sons, Inc. Somerset, N.J.). In illustrative embodiment, for example, acetylation is accomplished during the synthesis when the peptide is on the resin using acetic anhydride. Amide protection can be achieved by the selection of a proper resin for the synthesis. For example, a rink amide resin can be used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

Where amino acid sequences are disclosed herein, amino acid sequences comprising, one or more protecting groups, e.g., as described above (or any other commercially available protecting groups for amino acids used, e.g., in a boc or fmoc peptide synthesis) are also contemplated.

Peptide Circularization.

In certain embodiments the moieties described herein (e.g., calcium-binding peptides, chimeric constructs comprising calcium binding moieties, etc.) are circularized/cyclized to produce cyclic peptides. Cyclic peptides, as contemplated herein, include head/tail, head/side chain, tail/side chain, and side chain/side chain cyclized peptides. In addition, peptides contemplated herein include homodet, containing only peptide bonds, and heterodet containing in addition disulfide, ester, thioester-bonds, or other bonds.

The cyclic peptides can be prepared using virtually any art-known technique for the preparation of cyclic peptides. For example, the peptides can be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

In various embodiments cyclization can be achieved via direct coupling of the N- and C-terminus to form a peptide (or other) bond, but can also occur via the amino acid side chains. Furthermore it can be based on the use of other functional groups, including but not limited to amino, hydroxy, sulfhydryl, halogen, sulfonyl, carboxy, and thiocarboxy. These groups can be located at the amino acid side chains or be attached to their N- or C-terminus.

Accordingly it is to be understood that the chemical linkage used to covalently cyclize the peptides of the invention need not be an amide linkage. In many instances it may be desirable to modify the N- and C-termini of the linear or non-cyclized peptide so as to provide, for example, reactive groups that may be cyclized under mild reaction conditions. Such linkages include, by way of example and not limitation amide, ester, thioester, $CH_2$—NH, etc. Techniques and reagents for synthesizing peptides having modified termini and chemistries suitable for cyclizing such modified peptides are well-known in the art.

Alternatively, in instances where the ends of the peptide are conformationally or otherwise constrained so as to make cyclization difficult, it may be desirable to attach linkers to the N- and/or C-termini to facilitate peptide cyclization. Of course, it will be appreciated that such linkers will bear reactive groups capable of forming covalent bonds with the termini of the peptide. Suitable linkers and chemistries are well-known in the art and include those previously described.

Cyclic peptides and depsipeptides (heterodetic peptides that include ester (depside) bonds as part of their backbone) have been well characterized and show a wide spectrum of biological activity. The reduction in conformational freedom brought about by cyclization often results in higher receptor-binding affinities. Frequently in these cyclic compounds, extra conformational restrictions are also built in, such as the use of D- and N-alkylated-amino acids, $\alpha,\beta$-dehydro amino acids or $\alpha,\alpha$-disubstituted amino acid residues.

Methods of forming disulfide linkages in peptides are well known to those of skill in the art (see, e.g., Eichler and Houghten (1997) *Protein Pept. Lett.* 4: 157-164).

Reference may also be made to Marlowe (1993) *Biorg. Med. Chem. Lett.* 3: 437-44 who describes peptide cyclization on TFA resin using trimethylsilyl (TMSE) ester as an orthogonal protecting group; Pallin and Tam (1995) *J. Chem. Soc. Chem. Comm.* 2021-2022) who describe the cyclization of unprotected peptides in aqueous solution by oxime formation; Algin et al. (1994) *Tetrahedron Lett.* 35: 9633-9636 who disclose solid-phase synthesis of head-to-tail cyclic peptides via lysine side-chain anchoring; Kates et al. (1993) *Tetrahedron Lett.* 34: 1549-1552 who describe the production of head-to-tail cyclic peptides by three-dimensional solid phase strategy; Tumelty et al. (1994) *J. Chem. Soc. Chem. Comm.* 1067-1068, who describe the synthesis of cyclic peptides from an immobilized activated intermediate, where activation of the immobilized peptide is carried out with N-protecting group intact and subsequent removal leading to cyclization; McMurray et al. (1994) *Peptide Res.* 7: 195-206) who disclose head-to-tail cyclization of peptides attached to insoluble supports by means of the side chains of aspartic and glutamic acid; Hruby et al. (1994) *Reactive Polymers* 22: 231-241) who teach an alternate method for cyclizing peptides via solid supports; and Schmidt and Langer (1997) *J. Peptide Res.* 49: 67-73, who disclose a method for synthesizing cyclotetrapeptides and cyclopentapeptides.

These methods of peptide cyclization are illustrative and non-limiting. Using the teaching provide herein, other cyclization methods will be available to one of skill in the art.

Uses of Calcium-Binding Agents.

Hair Growth.

Figure 2:
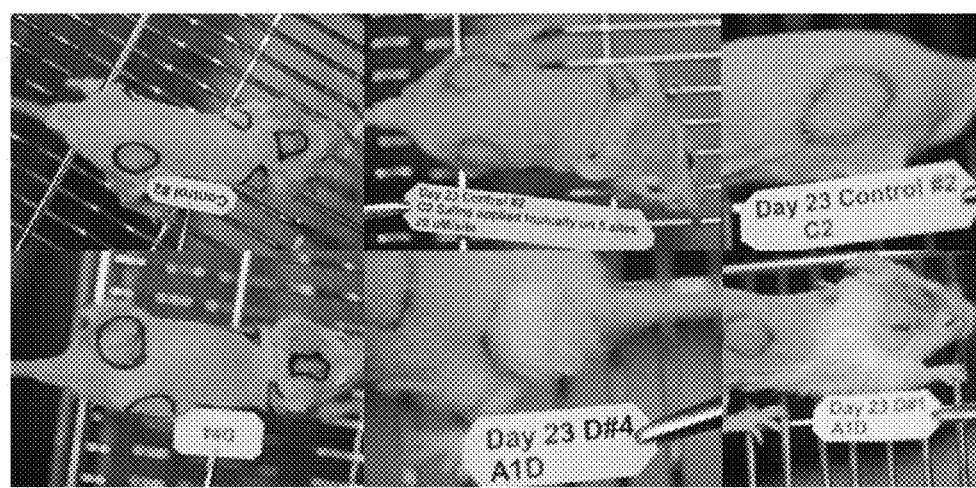
FIG. 2 illustrates the effect of calcium-binding compounds on hair growth in mice. Leftmost panel in each series shows mice at Day 0 after preparation and before treatment. Rightward panels show the mice at Day 23, the endpoint date. The top series shows the negative control receiving daily treatment with topical saline. The bottom series shows mice receiving daily treatment with a topical formulation of a DSS compound applied in outlined patches, demonstrating significant hair growth compared to controls.

It was a surprising and unexpected discovery that the calcium-binding peptides and other calcium-binding moieties described herein can induce hair growth when applied to the skin of a mammal (see, e.g., FIGS. 1 and 2). It is believed the agents can be used to induce hair growth, hair regrowth, and/or to inhibit hair loss in a mammal afflicted with a condition inducing hair loss (e.g., alopecia, chemotherapy, etc.). Typically the agent will be applied to the subject in need thereof in an amount sufficient to induce hair growth and/or to reduce hair loss.

The agent(s) can be administered via any of a number of routes including, for example topical administration, dermal/intradermal administration, transdermal administration, subdermal administration, transdermal iontopheresis, transdermal delivery of dendrimers, using polymer reverse micelles, using lipid reverse micelles, and the like.

In various embodiments hair growth or inhibition of hair loss comprises inhibition of hair loss on one or more regions where hair growth/maintenance is desired (e.g., one or more regions such as the head, the eyebrow, the mustache region (upper lip), the chest, and the like).

In certain embodiments the calcium-binding peptides and/or other calcium-binding moieties described herein are formulated for topical, dermal, intradermal, transdermal, or subdermal administration (e.g., as a rinses, tonic, solutions, emulsion, foam, cream, gel, ointments, dusting powder, liniment or balm, lotion, ointment, etc.).

In certain embodiments the calcium-binding peptides and/or other calcium-binding moieties described herein and/or formulations thereof are provided as components used in the treatment, maintenance, cleaning, or coloring of hair. Thus, for example, in certain embodiments, the calcium-binding peptides and/or other calcium-binding moieties described herein and/or formulations thereof are provided as components of a shampoo, a hair conditioner, a hair coloring agent, a hair detangler, a hair rinse, and the like.

Nail Growth.

Figure 12:
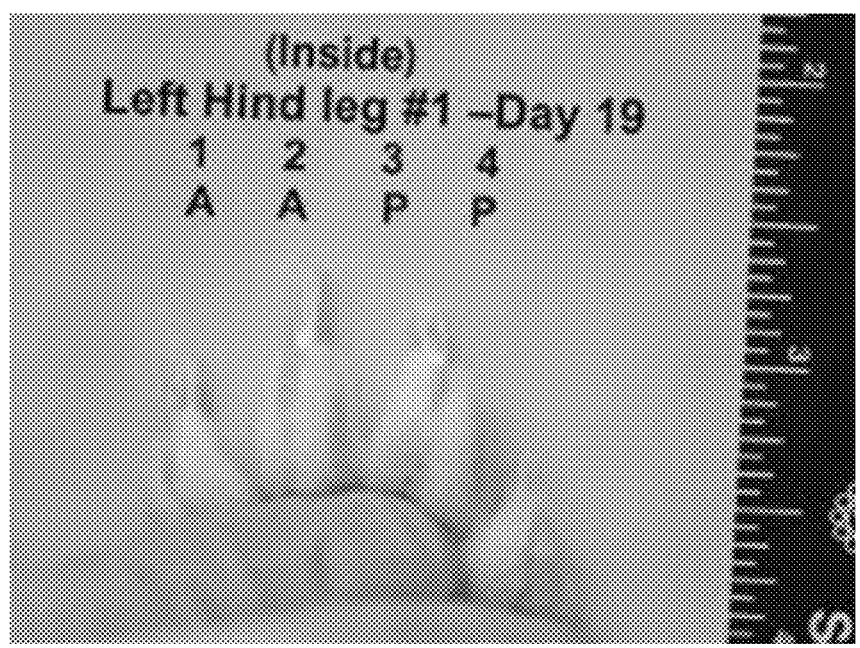
Figure 13:
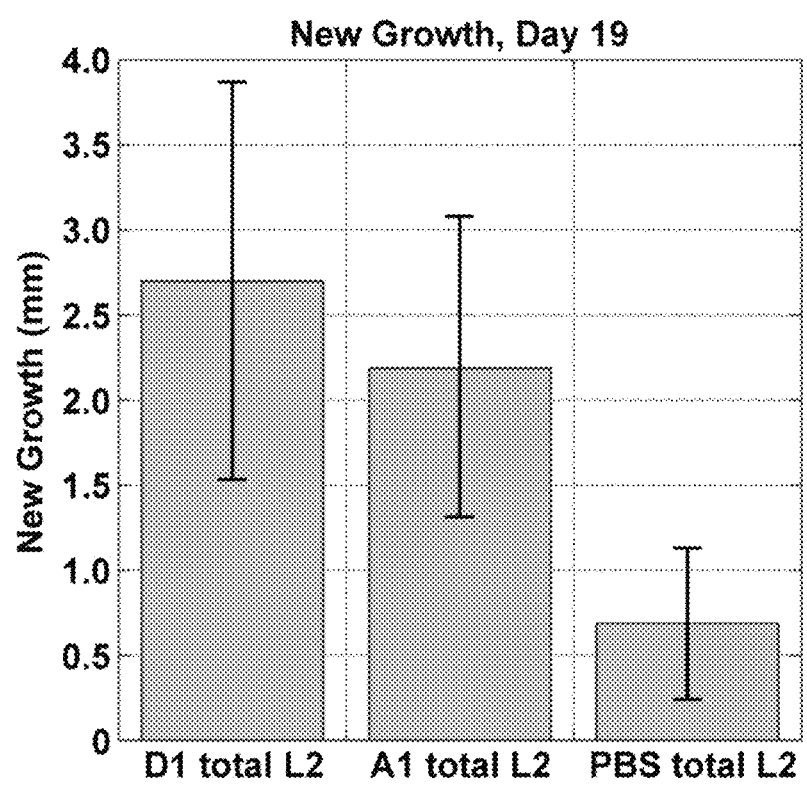
FIG. 13 shows a comparison of nail growth related to various treatments. After 19 days of treatment, nails were measured and the amount of new growth was determined for each treatment. New growth was significantly greater in nails treated with (D)-DSS-containing formulations

It was a surprising and unexpected discovery that the calcium-binding peptides and other calcium-binding moieties described herein can induce nail growth when applied to the nail, nail matrix, cuticle, and the like of a mammal (see, e.g., FIGS. 12 and 13). The peptides and other calcium-binding moieties can also be use to improve the growth and health of fingernails, toenails, animal hooves, claws, and horns.

In certain embodiments the calcium-binding peptides and other calcium-binding moieties described herein are applied to the nail matrix (cuticle), the coronet area of a hoof, or the base of the horn to enhance growth of the nail, claw, hoof, or horn. Formulations developed for dermal, intradermal, subdermal, and transdermal delivery are also effective for this purpose.

In certain embodiments the calcium-binding peptides and/or other calcium-binding moieties described herein and/or formulations thereof are provided as components used in the treatment, maintenance, cleaning, or coloring of nails, hooves, or horns. Thus, for example, in certain embodiments, the calcium-binding peptides and/or other calcium-binding moieties described herein and/or formulations thereof are provided as components of a formulation selected from the group consisting of a nail polish, a nail strengthener, a hoof balm, a varnish, a hoof or nail glue, a sealant, a cream, a lotion, a foot bath, a hoof bath, and the like.

In certain embodiments the calcium-binding peptides and other calcium-binding moieties described herein are applied daily or less frequently until the desired result is achieved.

Remineralization

The calcium-binding peptides and other calcium-binding moieties described herein induce calcium phosphate crystal growth on demineralized enamel and on both demineralized and nondemineralized dentin, depending on treatment conditions. Likewise, these agents can induce remineralization of bone. Thus, in certain embodiments, compositions comprising the calcium-binding agents disclosed herein may be used to enhance mineralization by recruiting free-floating calcium phosphate particles to calcified surfaces. These agents can bind to calcified surfaces and/or free-floating calcium phosphate aggregates. Concurrent binding of calcified surfaces and free-floating aggregates results in increased calcium phosphate concentration near the calcified surface, which leads to enhanced remineralization of the surface. By modulating the size and binding affinity of the agents, it is possible to alter the amount of calcium bound to the surface. In certain embodiments, remineralization of teeth results in complete or partial occlusion of dentinal tubules.

Compositions comprising the calcium-binding peptides and other moieties disclosed herein can be thus be used to remineralize a tooth, prevent or slow tooth demineralization, treat tooth damage, form mineral layers at or below the surface of a tooth, alter the mineral density of a tooth, such as for example increasing or decreasing mineral density, or seal a dental site. Likewise, these compositions can be used to treat a bone defect, injury, tumor, anomalous growth, illness, or bone loss, cause the formation of mineral layers at or below the surface of a bone, or alter the density of a bone, such as for example by increasing or decreasing density. In these embodiments, a composition comprising one or more calcium-binding agents as described above is applied at or near the site of the affected bone or bones. In certain embodiments, compositions comprising the calcium-binding agents disclosed herein can be used to treat calcification, calcareous lesions, or mineralized defects in tissues and organs other than bone, including arterial plaque.

As shown in Example 6, the calcium-binding peptides and other calcium-binding moieties described herein can enhance demineralization when used in conjunction with a tooth desensitizer/remineralizer (e.g., QUELL® desensitizer). Accordingly, methods are contemplated where the calcium-binding peptides and other calcium-binding moieties are used in conjunction with each other to enhance tooth remineralization and/or desensitization. Similarly compositions are contemplated comprising one or more of the calcium-binding peptides and other calcium-binding moieties described herein and one or more desensitizer/remineralizing agents. In certain embodiments the desensitizing/remineralizing agent includes calcium (e.g., calcium chloride and/or potassium phosphate), but need not be so limited. Illustrative desensitizing/remineralizing agents are shown in Table 4.

TABLE 4

Illustrative, but not limiting, desensitizers/remineralizing agents for use in conjunction with one or more calcium binding peptides and/or calcium binding moieties described herein.

| Product | Manufacturer | Active Agent(s) |
| --- | --- | --- |
| ADMIRA ® PROTECT SINGLEDOSE | Voco Gmbh | HEMA, Fluoride, Ormocer |
| D/SENSE CRYSTAL ® | Centrix | Potassium Nitrate, Calcium Oxalate |
| DURAFLOR ® SODIUM fluoride varnish | Medicom | Sodium Fluoride |
| DURAPHAT ® | Colgate Oral Pharmaceuticals | Sodium Fluoride |
| GEL-KAM DENTINBLOC ® | Colgate Oral Pharmaceuticals | Sodium Fluoride & Stannous Fluoride |
| GLUMA ® DESENSITIZER | Heraeus Kulzer | Glutaraldehyde |
| HEALTH-DENT ® DESENSITIZER | Healthdent'l | Benzalkonium Chloride |
| HEMASEAL ® & CIDE ® | Advantage Dental Products | Chlorhexidine, HEMA |
| HURRISEAL ® | Beutlich Pharmaceuticals | HEMA |
| QUELL ® DESENSITIZER | Pentron Clinical Technologies | Calcium Chloride, Potassium Phosphate |
| SUPER SEAL ® | Phoenix Dental | Oxalate Acid, Potassium Salt |
| SYSTEMP ® DESENSITIZER | Ivoclar Vivadent | Glutaraldehyde, Maleic Acid, Polyethylene Glycol, Dimethacrylate |
| ULTRAEZ ® | Ultradent | Potassium Nitrate, Fluoride |
| ZAROSEN ® | Cetylite Industries | Strontium Chloride |
| NovaMin ® containing products | Sultan Healthcare | calcium, phosphorus, silica and sodium |

In certain embodiments the calcium-binding peptide/moiety and the desensitizing/remineralizing agent are provided in a product such as a tooth paste, a mouthwash, a desensitizing cream, gel, paste, and the like.

Unlike current approaches to remineralization of tooth surfaces that rely on flooding the oral cavity with formulations of free or protein-bound calcium (e.g., formulations of free calcium, protein-bound calcium, sodium fluoride, stannous fluoride, and the like), these compounds cause calcium phosphate aggregates to specifically adhere to the tooth surface, thus increasing the local concentration of calcium and phosphate and increasing the probability that this calcium phosphate will be incorporated into demineralized regions of the tooth. Current pharmaceutical therapies for injuries or diseases of calcified tissues rely on surrounding the area of the desired surface, either directly (topically) or by systemic administration, with free solutions of the therapeutic compound of interest in the hope that some fraction will interact with the calcified surface.

Attachment to Calcified Surfaces/Substrates.

In certain embodiments, compositions comprising the calcium-binding peptides and other calcium-binding moieties described herein can be used as a means for specific attachment of desirable chemical moieties or particles to calcified surfaces, such as those of bones and teeth. The calcium-binding peptides and other calcium-binding moieties can be provided with an attached linker, and/or reactive site, or attached moiety (e.g., antibiotic, detectable label, etc.) and binding of the peptide or other calcium-binding moiety to a calcium-containing substrate provides the reactive group, linker localized at that site for subsequent attachment of a desired effector or where the effector of interest is attached to the calcium-binding peptide or other moiety the effector is thereby delivered to the calcium-containing substrate.

Assays for Dysfunctional Calcification.

In certain embodiments, compositions comprising the calcium-binding peptides and other calcium-binding moieties described herein can be used for in situ and in vivo assays for inappropriate calcification. For example, these compositions can be used to diagnose, identify, localize, or treat calcification, calcareous lesions, or mineralized defects in tissues and organs other than bone, including for example arterial plaque, kidney stones, or sesamoids. Assays currently in use for determining the presence of calcification include dye binding methods, incorporation of radioactive isotopes, X-ray transmission analysis, and quantitative chemical analysis. Each of these methods suffers from certain disadvantages. In dye binding methods, a sample is exposed to a calcium-chelating fluorescent dye such as tetracycline, calcein, or alizarin, and incorporation of the dye into the tissue of interest is visualized. Although the dyes can be introduced in vivo, visualization of the signal requires excision of the tissue of interest. Treatment of fixed tissue with silver ions (von Kossa staining) can also be used to identify sites of calcification, but this method cannot be applied in vivo and is subject to significant levels of background staining. Incorporation of radioactive isotopes such as $^{45}$Ca provides precise and quantitative information about the localization and rate of calcification in vivo, but has the drawback of exposing experimental subjects to high levels of ionizing radiation. X-ray transmission analysis provides high spatial resolution and can be accomplished in live animals, but cannot uniquely identify calcium deposits among the various other features visible in an X-ray image. In vitro quantitative chemical analysis of calcium deposits provides robust determinations of the type and amount of mineral present, but these methods are labor intensive and result in the loss of information about the location and structure of the tissue involved.

Visualization/Detection of Calcified Tissues or Regions.

In certain embodiments, compositions comprising the calcium-binding peptides and other moieties disclosed herein can be labeled fluorescently or otherwise and utilized as an improved means of visualizing calcified regions in a tissue of interest. These agents can be readily synthesized in high yields, and they have improved safety, toxicity, and ease of use compared to currently available methods. The sequence or composition of the agent can be altered to change the relative affinity of the agent for specific tissue or surface types (e.g., as described herein in the examples). This will allow the agent to discriminate between dentin, enamel, bone, and other calcified tissues or surfaces, and between healthy and diseased tissues. This property allows these compounds to be used as probes for injuries or pathological lesions in calcified tissue. The agents can be used alone, or in conjunction with other known methods for detecting calcification. In contrast to currently available calcium-binding fluorophores, that are limited to those that can chelate calcium ions while retaining their fluorescence, the peptides and other calcium-binding agents described herein can be attached to any fluorophore. This greatly expands the palette of colors that can be used to label calcified surfaces, and allows precise tailoring of emission wavelengths and detection technologies to each individual experiment. By conjugating these agents with fluorescent, colorimetric, radioactive, NMR-active, or other dyes or indicators and treating biological samples with these conjugates, it becomes possible to make quantitative observations of the extent of calcification in situ and in vivo without fixing or greatly disturbing the sample. Due to their high specificity and rapid binding rates, such conjugates can provide lower background staining than von Kossa silver ion staining methods. The wide variety of labels that can be attached to these calcium-binding agents offers enormous flexibility with regards to binding conditions and detection methods, which greatly increases the ease and quality with which biological, biomedical, biotechnological, environmental, and other research can be conducted.

Diagnostic Agents.

The peptides and other calcium-binding moieties described herein have great potential as diagnostic agents because unlike current methods of identifying injuries, infections, tumors or other lesions of calcified tissues, which rely primarily on visual or radiological observation, the peptides disclosed herein can be used to detect such events without reliance on the human eye. Various agents described herein have been shown to specifically target demineralized enamel and nondemineralized dentin. In particular, these agents have exhibited the ability to preferentially bind carious tooth lesions. Further, various variants have exhibited the ability to target precise subportions of the tooth structure, such as for example root tip dentin, basal enamel, mantle dentin, cortical enamel, and enamel surface. Compositions comprising calcium-binding agents conjugated to various detectable moieties, such as for example fluorescent, colorimetric, radioactive, NMR-active or other dyes or indicators, can be administered to a subject to target specific portions of the tooth and to identify those portions of the tooth exhibiting demineralization or other damage. The composition of the agents can be selected such that specific types of tissue or tissue damage can be targeted. Use of these agents allows for specific identification of damaged regions including those that can have been too small to see or otherwise obscured, greatly increasing the ease and accuracy of diagnosis for these lesions. Likewise, in certain embodiments, compositions comprising the calcium-binding agents disclosed herein can be used as contrast agents for X-ray, Computed Tomography, or Magnetic Resonance Imaging.

Targeting Moieties.

In certain embodiments, compositions comprising the calcium-binding peptides and other moieties disclosed herein can be used to target therapeutic compounds to the surfaces of bones, teeth, or other calcified tissues. For example, calcium-binding moieties can be conjugated to antimicrobial compounds, bone and tooth development modulators, or any other compound that can be attached to the moiety. Conjugation of a therapeutic compound to one of these moieties can be used to localize the therapeutic compound to a calcified surface, leading to increased local concentration of the compound and enhanced effectiveness. By localizing the compound to a tissue of interest, these moieties reduce the concentration of the compound needed to achieve the desired effect. In addition to improving efficacy, specific targeting of the therapeutic compound to a tissue of interest spares nontarget tissues from potentially damaging effects of the compound. The composition or length of the calcium-binding moiety can be adjusted to allow specific targeting to injured or diseased regions of the tissue.

Treating Microbial Infection.

In certain embodiments, compositions comprising the calcium-binding moieties disclosed herein can be used to treat a microbial infection, such as for example a bacterial infection. In these embodiments, the peptides can be linked to an antimicrobial peptide, such as for example a 2c-4, b-34, or PL-135 peptide (SEQ ID NOs: 26, 30, and 32, in WO 2007/038683, respectively) or to another antimicrobial moiety.

Based on the ability of the calcium-binding agents disclosed herein to selectively bind calcium or calcium phosphates, compositions comprising these agents can be incorporated into a sensor for the detection of calcium in drinking water, wastewater, industrial solutions, foods, beverages, research applications, or any solution for which determination of the presence of calcium is desired. Likewise, these compositions can be used to control the deposition of calcium minerals in, for example, industrial, manufacturing, medical, research, household, or personal applications. Further, these compositions can be employed to determine the presence or amount of various calcium minerals in, for example, cell cultures, tissues, experimental animals, experimental human subjects, or other research applications.

Chimeric Constructs.

The calcium-binding peptides and/or peptide-like calcium-binding moieties disclosed herein can be directly or indirectly linked, either covalently or noncovalently, to one or more conjugates or moieties. Such conjugates or moieties include, but are not limited to, other peptides, polypeptides, proteins, carbohydrates, nucleic acids, lipids, organic compounds, inorganic compounds, organometallic compounds, therapeutic moieties such as for example an anticancer or antimicrobial agent. Other examples of conjugates or moieties that can be linked to the calcium-binding peptides disclosed herein include detectable markers such as for example fluorophores, chromophores, affinity tags, radioactive labels, or spin labels. In addition, one or more atoms within a calcium-binding peptide or an attached conjugate or moiety can be replaced, for example, with a radioactive or NMR-active isotope.

The linkage between a calcium-binding agent and a conjugate or moiety can occur at the amino terminus of a peptide, the carboxy terminus of a peptide, or through an internal site in the peptide, or through a convenient group on a non-peptide calcium-binding agent. In certain embodiments, the agent can be linked to a conjugate or moiety via an amino acid linker, such as for example a triglycine linker sequence, or a non-amino acid linker. Illustrative suitable linkers are shown in Table 3.

Chemical Conjugation.

Chimeric moieties can be formed by joining one or more of the calcium-binding peptides or other moieties described herein to one or more effectors. In certain embodiments the Ca-binding moieties are attached directly to the effector(s) via naturally occurring reactive groups or the targeting moiety and/or the effector(s) can be functionalized to provide such reactive groups.

In various embodiments the Ca-binding moieties are attached to effector(s) via one or more linking agents. Thus, in various embodiments the Ca-binding moieties and the effector(s) can be conjugated via a single linking agent or multiple linking agents. For example, the Ca-binding moiety and the effector can be conjugated via a single multifunctional (e.g., bi-, tri-, or tetra-) linking agent or a pair of complementary linking agents. In another embodiment, the Ca-binding moiety and the effector are conjugated via two, three, or more linking agents. Suitable linking agents include, but are not limited to, e.g., functional groups, affinity agents, stabilizing groups, and combinations thereof.

In certain embodiments the linking agent is or comprises a functional group. Functional groups include monofunctional linkers comprising a reactive group as well as multifunctional crosslinkers comprising two or more reactive groups capable of forming a bond with two or more different functional targets (e.g., labels, proteins, macromolecules, semiconductor nanocrystals, or substrate). In some preferred embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine ($NH_2$), hydroxyl (—OH), aldehyde (—CHO), alcohol (ROH), ketone ($R_2CO$), active hydrogen, ester, sulfhydryl (SH), phosphate (—$PO_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful in forming chimeric moieties include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) *Advanced Organic Chemistry*, 3rd Ed., John Wiley & Sons, New York, Hermanson (1996) *Bioconjugate Techniques*, Academic Press, San Diego; and Feeney et al. (1982) *Modification of Proteins; Advances in Chemistry Series*, Vol. 98, American Chemical Society, Washington, D.C.

In certain embodiments, the linking agent comprises a chelator. For example, the chelator comprising the molecule, DOTA (1,4,7,10-tetrakis(carboxymethyl)-1,4,7,10-tetraazacyclododecane), can readily be labeled with a radiolabel, such as $Gd^{3+}$ and $^{64}Cu$, resulting in $Gd^{3+}$-DOTA and $^{64}Cu$-DOTA respectively, attached to the Ca-binding moiety. Other suitable chelates are known to those of skill in the art, for example, 1,4,7-triazacyclononane-N,N',N''-triacetic acid (NOTA) derivatives being among the most well known (see, e.g., Lee et al. (1997) *Nucl Med. Biol.* 24: 2225-23019).

A "linker" or "linking agent" as used herein, is a molecule that is used to join two or more molecules. In certain embodiments the linker is typically capable of forming covalent bonds to both molecule(s) (e.g., the Ca-binding moiety and the effector). Suitable linkers are well known to those of skill in the art and include, but are not limited to, straight or branched-chain carbon linkers, heterocyclic carbon linkers, or peptide linkers. In certain embodiments the linkers can be joined to the constituent amino acids through their side groups (e.g., through a disulfide linkage to cysteine). However, in certain embodiments, the linkers will be joined to the alpha carbon amino and carboxyl groups of the terminal amino acids.

A bifunctional linker having one functional group reactive with a group on one molecule (e.g., a Ca-binding peptide), and another group reactive on the other molecule (e.g., an antimicrobial peptide), can be used to form the desired conjugate. Alternatively, derivatization can be performed to provide functional groups. Thus, for example, procedures for the generation of free sulfhydryl groups on peptides are also known (See U.S. Pat. No. 4,659,839).

In certain embodiments the linking agent is a heterobifunctional crosslinker comprising two or more different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In one embodiment, the heterobifunctional crosslinker is SMCC.

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). Illustrative linking protocols are provided herein in Examples 2 and 3. Illustrative suitable linkers include, but are not limited to those shown in Table 3.

Fusion Proteins.

In certain embodiments where the Ca-binding moiety and effector are both peptides or both comprise peptides, the chimeric moiety can be chemically synthesized or recombinantly expressed as a fusion protein (i.e., a chimeric fusion protein).

In certain embodiments the chimeric fusion proteins are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins of the present invention may be cloned using DNA amplification methods such as polymerase chain reaction (PCR). Thus, for example, the nucleic acid encoding a Ca-binding moiety is PCR amplified, using a sense primer containing the restriction site for NdeI and an antisense primer containing the restriction site for HindIII. This produces a nucleic acid encoding the Ca-binding sequence and having terminal restriction sites. Similarly an effector and/or effector/linker/spacer can be provided having complementary restriction sites. Ligation of sequences and insertion into a vector produces a vector encoding the fusion protein.

While the Ca-binding moieties and effector(s) can be directly joined together, one of skill will appreciate that they can be separated by a peptide spacer/linker consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270).

One of skill would recognize that modifications can be made to the fusion proteins without diminishing their biological activity. Some modifications may be made to facilitate the cloning, expression, or incorporation of the Ca-binding molecule into a fusion protein. Such modifications are well known to those of skill in the art and include, for example, a methionine added at the amino terminus to provide an initiation site, or additional amino acids placed on either terminus to create conveniently located restriction sites or termination codons.

As indicated above, in various embodiments a peptide linker/spacer is used to join the one or more Ca-binding moieties to one or more effector(s). In various embodiments the peptide linker is relatively short, typically less than about 10 amino acids, preferably less than about 8 amino acids and more preferably about 3 to about 5 amino acids. Suitable illustrative linkers include, but are not limited to various peptide linkers shown above in Table 3.

Administration and Formulations.

In certain embodiments, the calcium-binding agents described herein and/or the chimeric constructs comprising such moieties (e.g., calcium-binding agents attached to antimicrobial peptide(s), detectable label(s), etc.) are administered to a mammal in need thereof, to a cell, to a tissue, to a composition (e.g., a food), etc.). In various embodiments the compositions can be administered to detect and/or locate, and/or quantify the presence of abnormal calcification and/or demineralization, and the like. In various embodiments the compositions can be administered to inhibit hair loss and/or to induce hair growth, and/or to increase nail growth or repair, hoof growth or repair, horn growth or repair, and the like.

These active agents (calcium-binding moieties and/or calcium-binding peptides and/or chimeric constructs comprising calcium-binding moieties and/or calcium-binding peptides attached to one or more effectors (e.g., detectable labels, antimicrobial, etc.) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

Methods of formulating such derivatives are known to those of skill in the art. For example, the disulfide salts of a number of delivery agents are described in PCT Publication WO 00/059863. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein are useful for parenteral, topical, dermal, intradermal, subdermal, oral, nasal (or otherwise inhaled), pulmonary, rectal, or other local administration, such as by aerosol or transdermally to induce calcification and/or nail growth, and/or hair growth and/or to deliver an effector to a site of calcification or defective calcification. The compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, lipid complexes, etc.

The active agents (e.g., calcium-binding agents and/or chimeric constructs) described herein can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, surfactants, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., active) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain therapeutic applications, the compositions of this invention are administered, e.g., topically administered, transdermally administered (e.g., to induce hair growth and/or to inhibit hair loss) in an amount sufficient to prevent and/or cure and/or at least partially prevent or arrest the pathology and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms in) the patient.

The concentration of active agent(s) can vary widely, and will be selected primarily based on activity of the active ingredient(s), body weight and the like in accordance with the particular mode of administration selected and the patient's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic and/or prophylactic regimen in a particular subject or group of subjects.

In certain embodiments, the active agents of this invention are administered to the oral cavity. This is readily accomplished by the use of toothpaste, mouthwash, lozenges, aerosol sprays, strips that adhere to the teeth (e.g., whitestrips), coated swabs, gels, varnishes, quick dissolving strips (e.g., oral pain relieving strips (e.g. ORAFILM®), breath freshening strips, antihistamine strips) and the like.

In certain embodiments, the active agent(s) of this invention are administered topically, e.g., to the skin surface, to a topical lesion or wound, to a surgical site, to a surgical implant, and the like.

In certain embodiments the active agents of this invention are administered systemically (e.g., orally, or as an injectable) in accordance with standard methods well known to those of skill in the art. In other preferred embodiments, the agents can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Other formulations for topical delivery include, but are not limited to, ointments, gels, sprays, fluids, and creams. Ointments are semisolid preparations that are typically based on petrolatum or other petroleum derivatives. Creams containing the selected active agent are typically viscous liquid or semi-solid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and non-sensitizing.

As indicated above, various buccal, and sublingual formulations are also contemplated.

In certain embodiments, one or more active agents of the present invention can be provided as a "concentrate", e.g., in a storage container (e.g., in a premeasured volume) ready for dilution, or in a soluble capsule ready for addition to a volume of water, alcohol, hydrogen peroxide, or other diluent.

B) Nanoemulsion Formulations.

In certain embodiments the calcium-binding moieties and/or calcium-binding peptides and/or chimeric moieties described herein are formulated in a nanoemulsion. Nanoemulsions include, but are not limited to oil in water (O/W) nanoemulsions, and water in oil (W/O) nanoemulsions. Nanoemulsions can be defined as emulsions with mean droplet diameters ranging from about 20 to about 1000 nm. Usually, the average droplet size is between about 20 nm or 50 nm and about 500 nm. The terms sub-micron emulsion (SME) and mini-emulsion are used as synonyms.

Illustrative oil in water (O/W) nanoemulsions include, but are not limited to:

Surfactant micelles—micelles composed of small molecules surfactants or detergents (e.g., SDS/PBS/2-propanol) which are suitable for predominantly hydrophobic peptides.

Polymer micelles—micelles composed of polymer, copolymer, or block copolymer surfactants (e.g., Pluronic L64/PBS/2-propanol) which are suitable for predominantly hydrophobic peptides;

Blended micelles: micelles in which there is more than one surfactant component or in which one of the liquid phases (generally an alcohol or fatty acid compound) participates in the formation of the micelle (e.g., Octanoic acid/PBS/EtOH) which are suitable for predominantly hydrophobic peptides;

Integral peptide micelles—blended micelles in which the peptide serves as an auxiliary surfactant, forming an integral part of the micelle (e.g., amphipathic peptide/PBS/mineral oil) which are suitable for amphipathic peptides; and Pickering (solid phase) emulsions—emulsions in which the peptides are associated with the exterior of a solid nanoparticle (e.g., polystyrene nanoparticles/PBS/no oil phase) which are suitable for amphipathic peptides.

Illustrative water in oil (W/O) nanoemulsions include, but are not limited to:

Surfactant micelles—micelles composed of small molecules surfactants or detergents (e.g., dioctyl sulfosuccinate/PBS/2-propanol, Isopropylmyristate/PBS/2-propanol, etc.) which are suitable for predominantly hydrophilic peptides;

Polymer micelles—micelles composed of polymer, copolymer, or block copolymer surfactants (e.g., PLURONIC® L121/PBS/2-propanol), which are suitable for predominantly hydrophilic peptides;

Blended micelles—micelles in which there is more than one surfactant component or in which one of the liquid phases (generally an alcohol or fatty acid compound) participates in the formation of the micelle (e.g., capric/caprylic diglyceride/PBS/EtOH) which are suitable for predominantly hydrophilic peptides;

Integral peptide micelles—blended micelles in which the peptide serves as an auxiliary surfactant, forming an integral part of the micelle (e.g., amphipathic peptide/PBS/polypropylene glycol) which are suitable for amphipathic peptides; and Pickering (solid phase) emulsions—emulsions in which the peptides are associated with the exterior of a solid nanoparticle (e.g., chitosan nanoparticles/no aqueous phase/mineral oil) which are suitable for amphipathic peptides.

As indicated above, in certain embodiments the nanoemulsions comprise one or more surfactants or detergents. In some embodiments the surfactant is a non-anionic detergent (e.g., a polysorbate surfactant, a polyoxyethylene ether, etc.). Surfactants that find use in the present invention include, but are not limited to surfactants such as the TWEEN®, TRITON®, and TYLOXAPOL® families of compounds.

In certain embodiments the emulsions further comprise one or more cationic halogen containing compounds, including but not limited to, cetylpyridinium chloride. In still further embodiments, the compositions further comprise one or more compounds that increase the interaction ("interaction enhancers") of the composition with microorganisms (e.g., chelating agents like ethylenediaminetetraacetic acid, or ethylenebis (oxyethylenenitrilo)tetraacetic acid in a buffer).

In some embodiments, the nanoemulsion further comprises an emulsifying agent to aid in the formation of the emulsion. Emulsifying agents include compounds that aggregate at the oil/water interface to form a kind of continuous membrane that prevents direct contact between two adjacent droplets. Certain embodiments of the present invention feature oil-in-water emulsion compositions that may readily be diluted with water to a desired concentration without impairing their properties (e.g., calcium binding, hair or nail growth inducing/accelerating, etc.).

In addition to discrete oil droplets dispersed in an aqueous phase, certain oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water).

These lipid structures are formed as a result of hydrophobic forces that drive apolar residues (e.g., long hydrocarbon chains) away from water. The above lipid preparations can generally be described as surfactant lipid preparations (SLPs). SLPs are minimally toxic to mucous membranes and are believed to be metabolized within the small intestine (see e.g., Hamouda et al., (1998) *J. Infect. Disease* 180: 1939).

In certain embodiments the emulsion comprises a discontinuous oil phase distributed in an aqueous phase, a first component comprising an alcohol and/or glycerol, and a second component comprising a surfactant or a halogen-containing compound. The aqueous phase can comprise any type of aqueous phase including, but not limited to, water (e.g., dionized water, distilled water, tap water) and solutions (e.g., phosphate buffered saline solution, or other buffer systems). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In certain embodiments, the oil phase comprises 30-90 vol % of the oil-in-water emulsion (i.e., constitutes 30-90% of the total volume of the final emulsion), more preferably 50-80%.

In certain embodiments the alcohol, when present, is ethanol.

While the present invention is not limited by the nature of the surfactant, in some preferred embodiments, the surfactant is a polysorbate surfactant (e.g., TWEEN 20®, TWEEN 40®, TWEEN 60®, and TWEEN 80®), a pheoxypolyethoxyethanol (e.g., TRITON® X-100, X-301, X-165, X-102, and X-200, and TYLOXAPOL®), or sodium dodecyl sulfate, and the like.

In certain embodiments a halogen-containing component is present. the nature of the halogen-containing compound, in some preferred embodiments the halogen-containing compound comprises a chloride salt (e.g., NaCl, KCl, etc.), a cetylpyridinium halide, a cetyltrimethylammonium halide, a cetyldimethylethylammonium halide, a cetyldimethylbenzylammonium halide, a cetyltributylphosphonium halide, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, tetradecyltrimethylammonium bromide, and the like In certain embodiments the emulsion comprises a quaternary ammonium compound. Quaternary ammonium compounds include, but are not limited to, N-alkyldimethyl benzyl ammonium saccharinate, 1,3,5-Triazine-1,3,5(2H,4H, 6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl)ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl)octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis(alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

Nanoemulsion formulations and methods of making such are well known to those of skill in the art and described for example in U.S. Pat. Nos. 7,476,393, 7,468,402, 7,314,624, 6,998,426, 6,902,737, 6,689,371, 6,541,018, 6,464,990, 6,461,625, 6,419,946, 6,413,527, 6,375,960, 6,335,022, 6,274,150, 6,120,778, 6,039,936, 5,925,341, 5,753,241, 5,698,219, an d5,152,923 and in Fanun et al. (2009) Microemulsions: Properties and Applications (Surfactant Science), CRC Press, Boca Ratan Fl.

C) Formulations Optimizing Activity.

In certain embodiments, formulations are selected to optimize binding specificity, and/or binding avidity, and/or stability/conformation, and/or delivery/activity of the calcium-binding moiety, calcium-binding peptide, and/or chimeric moiety described herein. In certain embodiments, suitable formulations include, but are not limited to the following:

For injection, a calcium-binding moiety and/or calcium-binding peptide (e.g., 4DSS, 6DSS, 8DSS, 10DSS, (D)-4DSS, (D)-6DSS, (D)-8DSS, (D)-10DSS, etc.) is dissolved/mixed in sterile distilled water, saline solution, or ringers solution and adjusted to a pH that ranges from about pH 4 to about pH 8, or about pH 4.6 to about pH 7.9, or an approximately neutral pH (e.g., pH 7.3). In certain embodiments, the calcium-binding peptide and/or calcium-binding moiety is present at a concentration ranging from about 0.4 or about 1 mg/mL to a about 500 mg/mL, or from about 10 mg/mL to about 100 mg/mL, or from about 25 mg/mL to about 75 mg/mL, and in certain embodiments about 40-50 mg/mL. In illustrative formulation, the peptide is dissolved/mixed to a concentration of 46.7 mg/mL in sterile distilled water, pH adjusted to 7.3 with 5M NaOH.

Illustrative topical formulations include, but are not limited to:

A formulation comprising (or consisting essentially of) the calcium-binding peptide (e.g., 4DSS (SEQ ID NO:31), 6DSS (SEQ ID NO:32), 8DSS (SEQ ID NO:33), 10DSS (SEQ ID NO:44), (D)-4DSS, (D)-6DSS, (D)-8DSS, (D)-10DSS, etc.) and/or calcium-binding moiety is present at a concentration ranging from about 0.4 or about 1 mg/mL to a about 500 mg/mL, or from about 10 mg/mL to about 100 mg/mL, or from about 25 mg/mL to about 75 mg/mL, or about 40-50 mg/mL, or about 0.466 mg/mL to about 46.7 mg/mL in DMSO.

2) An emulsion comprising (or consisting essentially of):
  a) about 1% to about 80%, or about 1% to about 50%, or about 1% to about 20% calcium-binding moiety and/or calcium-binding peptide in a solution, suspension, or mixture in a pharmaceutically acceptable buffer solution with a pH ranging from about pH 4 to about pH 8, or about pH 4.6 to about pH 7.9, or about pH 5 or 6 to about pH 7.9;
  b) about 1% to about 60%, about 50%, or about 40% Pluronic 17R4, 22R4, 25R4, L62, L63, L64, P65, P75, P84, P85 F68, F77, F87, or comparable block copolymer; and
  c) remainder or substantial remainder alcohol (e.g., 2-propanol, ethanol, propanol, or similar alcohol). Typically the peptide solution and pluronic solution are prepared separately and then combined. One illustrative formulation comprises 10% of a 46.7 mg/mL solution of (D)-8DSS in sterile distilled water, pH adjusted to 7.0 with 5M NaOH suspended in a solution of 10% Pluronic 17R4 (Poly(propylene glycol)-block-poly(ethylene glycol)-block-polypropylene glycol); BASF, Florham Park, N.J.) in 2-propanol.

3) An emulsion comprising (or consisting essentially of):
  a) about 1% to about 80%, or about 1% to about 50%, or about 1% to about 20% calcium-binding moiety and/or calcium-binding peptide in a solution, suspension, or mixture in a pharmaceutically acceptable buffer solution with a pH ranging from about pH 4 to about pH 8, or about pH 4.6 to about pH 7.9, or about pH 5 or 6 to about pH 7.9;
  b) about) about 1% to about 60%, about 50%, or about 40% dioctyl sulfosuccinate, lecithin, isopropyl myristate, or comparable surfactant capable of forming water-in-oil emulsions; and
  c)) remainder or substantial remainder alcohol (e.g., 2-propanol, ethanol, propanol, or similar alcohol). Typically the peptide solution and surfactant solution are prepared separately and then combined. One illustrative formulation comprises 10% of a 46.7 mg/mL solution of (D)-8DSS in sterile distilled water, pH adjusted to 7.0 with 5M NaOH suspended in a solution of 17.8% dioctyl sulfosuccinate in 2-propanol.

4) Emulsions (2) and/or (3), further incorporating 1-50%, 1-30%, or 1-20% emollient (e.g., one or more emollients selected from the group consisting of glycerin, glycerol, glyceryl monooleate, diprobase, aloe vera, jojoba oil, glycerol, vitamin A (e.g., retinal, retinoic acid, palmitate, retinal, tretinoin, and isotretinoin, etc.), triethanolamine, vitamin E, soybean oil, avocado oil, coconut oil, etc.).

5) Compositions comprising 0.00001-30%, or 0.00001-20%, or 0.00001-10% (w/v) of the calcium-binding moiety and/or calcium-binding peptide attached to calcium phosphate (including hydroxyapatite, beta tricalcium phosphate, octacalcium phosphate or other calcium phosphate forms) nano or microparticles (with an average particle size between 1 nm and 400 nm, or between 1 nm and 1 μm, or between 1 nm and 1,000 μm) suspended in a pharmaceutically acceptable carrier (including, not limited to isopropyl alcohol, buffered saline solution, an emulsion, and the like).

While the methods and compositions are described herein with respect to use in humans, they are also suitable for animal, e.g., veterinary use. Thus certain suitable organisms include, but are not limited to humans, non-human primates, canines, equines, felines, porcines, ungulates, lagomorphs, and the like.

The foregoing formulations and administration methods are intended to be illustrative and not limiting. It will be appreciated that, using the teaching provided herein, other suitable formulations and modes of administration can be readily devised.

Kits.

In another embodiment this invention provides kits for inducing hair growth and/or inhibiting hair loss, for detecting abnormal calcification and/or demineralization, for inducing remineralization, and the like. The kits typically comprise a container containing one or more of the active agents (i.e., the calcium-binding agents and/or chimeric moieties) described herein. In certain embodiments the active agent(s) can be provided in a unit dosage formulation (e.g., suppository, tablet, caplet, patch, etc.) and/or may be optionally combined with one or more pharmaceutically acceptable excipients.

In addition, the kits optionally include labeling and/or instructional materials providing directions (i.e., protocols) for the practice of the methods or use of the "therapeutics" or "prophylactics" or detection reagents of this invention. Certain instructional materials describe the use of one or more active agent(s) of this invention to induce hair growth and/or inhibit hair loss, to detecting abnormal calcification and/or demineralization, to induce remineralization, and the like. The instructional materials may also, optionally, teach preferred dosages/therapeutic regimen, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Calcium-Binding Peptides Induce Hair Growth

FIG. 1 shows DSS-treated (right) and mock-treated (left) mice showing hair regrowth 13 days after shaving of the scalp. FIG. 2 illustrates the effect of calcium-binding compounds on hair growth in mice. Leftmost panel in each series shows mice at day 0 after preparation and before treatment. Rightward panels show the mice at day 23, the endpoint date. The top series shows the negative control receiving daily treatment with topical saline. The bottom series shows mice receiving daily treatment with a topical formulation of a DSS compound applied in outlined patches, demonstrating significant hair growth compared to controls.

Example 2

Nucleation of Hydroxyapatite on Tooth Enamel and Dentin by DSS Peptides

To determine whether applying DSS to various preparations of tissue promoted HA nucleation, that could ultimately lead to tissue remineralization, sagittally sectioned adult human teeth (obtained after extraction during normal clinical practice) were polished using a Streurs grinding wheel, and prepared for nucleation experiments. Half of the sections were demineralized with 35% phosphoric acid for 15 minutes, then rinsed thoroughly with deionized water. The other half were left untreated. All samples were then sonicated for five minutes to remove excess debris left from cutting and grinding and/or demineralization. Samples were treated with 12.5 μM 8DSS dissolved in 50 mM HEPES buffer solution (pH 7.0), buffer solution only, or left untreated. Samples were then immersed into a simulated body fluid (SBFn), meant to accelerate nucleation of hydroxyapatite (HA) crystals, for 4 hours. Following the nucleation step, samples were immersed in a magnesium and bicarbonate free solution (SBFg) in order to allow the nucleated HA crystals to grow. Table 5 shows the composition of SBFn and SBFg solutions in comparison with blood plasma. Both solutions were adjusted to pH 6.8. Crystals were grown in order to amplify the nucleated crystals for easy visualization by SEM.

TABLE 5

| SBFn and SBFg solution composition. | | | | | | | | |
|---|---|---|---|---|---|---|---|---|
| Ionic Conc. | Na+ | K+ | $Ca^{2+}$ | $Mg^{2+}$ | $HCO_3^-$ | $Cl^-$ | $HPO_4^{2-}$ | $SO_4^{2-}$ |
| Blood Plasma | 142.0 | 5.0 | 2.5 | 1.5 | 27.0 | 103.0 | 1.0 | 0.5 |
| SBFn | 284.0 | 10.0 | 5.0 | 3.0 | 54.0 | 206.0 | 2.0- | 1.0 |
| SBFg | 284.0 | 4.0 | 5.0 | 0 | 0 | 294.0 | 2.0 | 0 |

Figure 3:
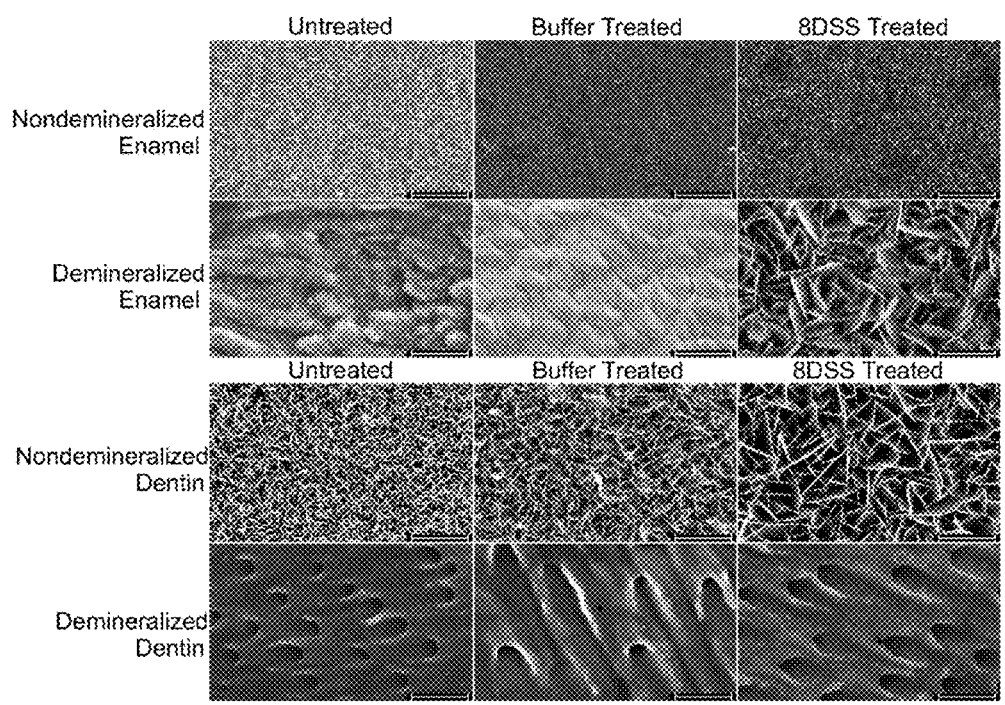
FIG. 3 illustrates nucleation of hydroxyapatite on enamel (top) and dentin (bottom) surfaces. Surfaces were prepared and treated as indicated by the labels, followed by imaging using Scanning Electron Microscopy. The upper group (top two rows) represents enamel samples, while the lower group (bottom two rows) represents dentin samples. Within each group, the top row represents samples that were not demineralized prior to treatment, and the bottom row represents samples that were demineralized by treatment with phosphoric acid. Scanning electron micrographs are shown, scale bars=1 0 pM. Left column: samples that were not exposed to any treatment prior to nucleation and crystal growth. Center column: samples that were exposed to buffer only prior to nucleation and crystal growth. Right column: samples that were exposed to 12.5 pM 8DSS (SEQ ID NO:33) peptide prior to nucleation and crystal growth. Crystal growth indicates early nucleation.

The surface of the nondemineralized, untreated, and buffer treated enamel remained largely amorphous, indicating little or no crystal growth (and thus little or no nucleation) (FIG. 3, upper two rows). However, significant crystal growth (indicating early and robust nucleation) was observed in demineralized enamel exposed to 8DSS peptide (FIG. 3, upper two rows). This indicates that DSS peptides can specifically recognize demineralized enamel and nucleate hydroxyapatite growth on the demineralized enamel surface.

The surface of the nondemineralized dentin exhibited some degree of crystal growth in the untreated and buffer treated samples. However, the most significant growth, and thus the earliest and most robust nucleation, occurred in the sample treated with the 8DSS peptide (FIG. 3, lower two rows). We have previously demonstrated the ability of DSS peptides, in conjunction with existing remineralization regimens, to cause deposition of thick layers of calcium phosphate sufficient to occlude the dentinal tubules on demineralized dentin. These results indicate that with a slightly different treatment crystal nucleation occurs primarily on nondemineralized dentin. Thus, depending on the specific treatment regimen employed, DSS peptides can be used to deposit layers of calcium phosphate on demineralized dentin or to cause robust nucleation of hydroxyapatite crystal growth on fully mineralized surfaces. This means that DSS peptides can be used, for example, to treat tooth sensitivity due to exposure of dentinal tubules, to remineralize mechanically debrided dentin involved caries, or to repair fractured dentinal surfaces.

Example 3

Tissue Specific Binding of DSS Peptides in Human Teeth

Figure 4:
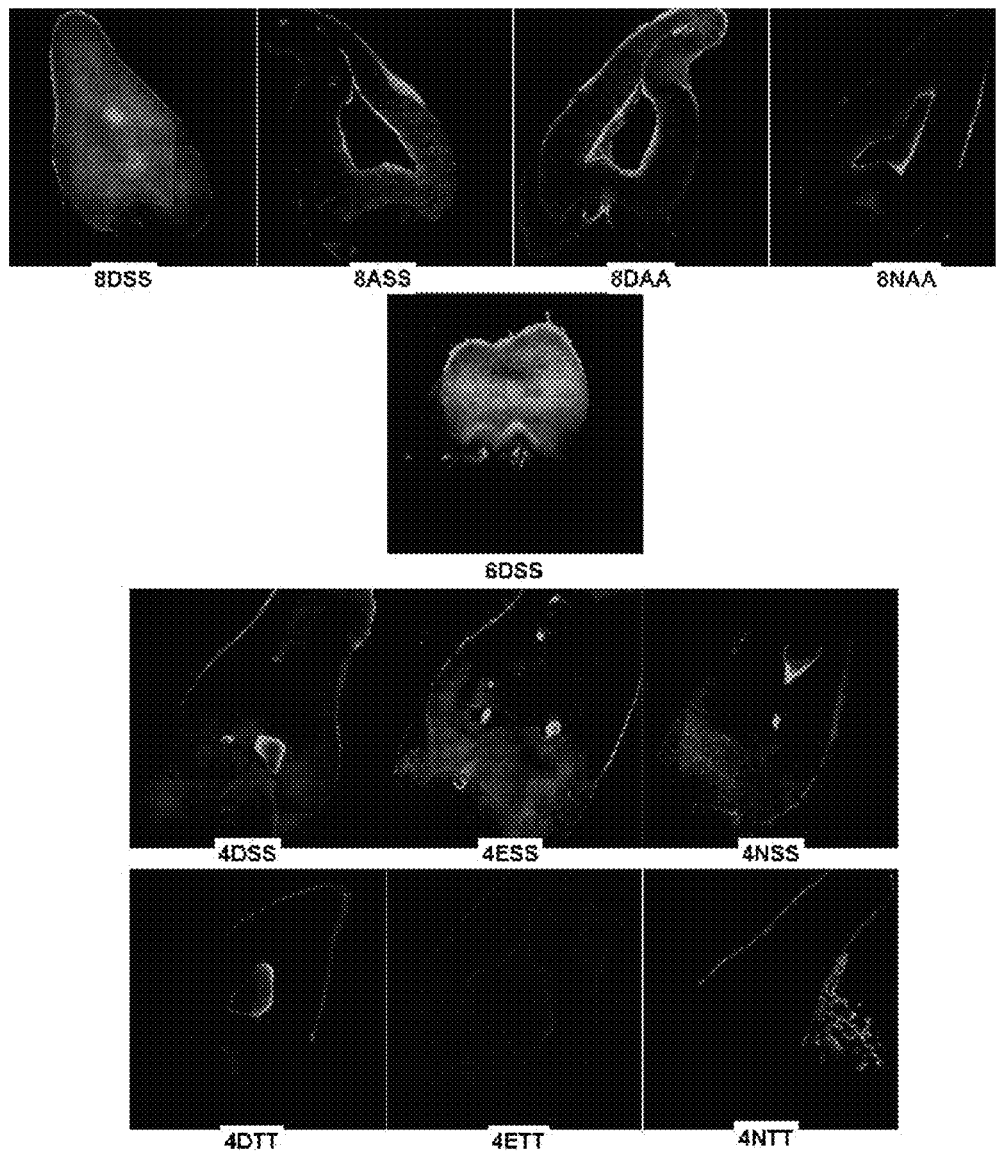
FIG. 4 provides fluorescence micrographs showing tissue specificity in the binding of DSS peptides and variants (8DSS=SEQ ID NO:33; 8ASS=SEQ ID NO:26; 8DAA=SEQ ID NO:40; 8NAA=SEQ ID NO:41; 6DSS=SEQ ID NO:32; 4DSS=SEQ ID NO:31; 4ESS=SEQ ID NO:34; 4NSS=SEQ ID NO:35; 4DTT=SEQ ID NO:36; 4ETT=SEQ ID NO:37; 4NTT=SEQ ID NO:38). Adult human teeth were exposed to 12.5 pM 5(6)-carboxyfluorescein-labeled peptide without demineralization, washed extensively, and imaged by CLSM. For each section, multiple scans were collected and assembled in an automated mode to generate panels of images representing an area of 13×13 mm, sufficient in most cases to encompass the whole section. The peptides used for each section are labeled beneath each panel, and within each panel the tooth is oriented with the root toward the top of the image and the crown toward the bottom. Tissue layers are labeled as follows: RTD=Root Tip Dentin; CPD=Circumpulpal Dentin; MD=Mantle Dentin; P=Pulp Cavity Wall; DEJ=Dentin-Enamel Junction; E=Enamel; BE=Basal Enamel; CE=Cortical Enamel; CL=Carious Lesion; PB=Periodontal Bone.

In order to investigate the tissue specificity of DSS peptide binding to tooth tissue, sections of human teeth were exposed to DSS peptides and variants, then imaged by CLSM. The peptides utilized for these experiments were 8DSS (SEQ ID NO:33), 8ASS (SEQ ID NO:26), 8DAA (SEQ ID NO:40), 8NAA (SEQ ID NO:41), 4DSS (SEQ ID NO:31), 4ESS (SEQ ID NO:34), 4NSS (SEQ ID NO:35), 4DTT (SEQ ID NO:36), 4ETT (SEQ ID NO:37), 4NTT (SEQ ID NO:38), and 6DSS (SEQ ID NO:32). Sagittal sections of human teeth extracted during normal clinical practice were polished and then incubated for ten minutes in a solution of the appropriate 5(6) carboxyfluorescein-labeled peptide (12.5pM) containing 10 mM NaCl and 50 mM HEPES, pH 7.0. Control samples were prepared without peptide. Samples were washed extensively after treatment and imaged by CLSM using blue laser illumination (λ=488 nm) and a FITC emission filter, with identical camera and microscope settings for each sample. For each section, multiple scans were collected and assembled in an automated mode to generate panels of images representing an area of 13×13 mm, sufficient in most cases to encompass the whole section. As suggested by previous binding affinity results, peptides containing the sequence (DSS) exhibited the highest levels of binding to tooth surfaces, with 6DSS (SEQ ID NO:32) and 8DSS (SEQ ID NO:33) showing the greatest levels of staining. The results of these experiments are set forth in FIG. 4. 8DSS (SEQ ID NO:33), 6DSS (SEQ ID NO:32), and 4DSS (SEQ ID NO:31) bound primarily to the mantle dentin, with a sharply delineated dentin-enamel junction, low or no binding to the root tip dentin or the basal enamel, and no detectable binding to either the cortical enamel or the enamel surface. Significant binding was also seen to the edges of the pulp cavity. 8ASS (SEQ ID NO:26), 4ESS (SEQ ID NO:34), and 4NSS (SEQ ID NO:35) exhibited similar patterns, though at lower levels of binding. 8DAA (SEQ ID NO:40) exhibited an inversion of this binding pattern, with primary binding to the root tip dentin and cortical enamel, as well as to the dentin-enamel junction and the pulp cavity wall. 8DAA (SEQ ID NO:40) exhibited little or no binding to the mantle dentin, circumpulpal dentin, or basal enamel. 4DTT (SEQ ID NO:36) and 4ETT (SEQ ID NO:37) exhibited binding patterns similar to those of 4DSS (SEQ ID NO:31) and 4ESS (SEQ ID NO:34), though at sharply reduced levels.

8NAA (SEQ ID NO:40) exhibited very little binding to any healthy tissue, but did bind somewhat to a carious lesion present in the sample (see Example below). 4NTT exhibited strong binding to a fragment of periodontal bone attached to the sample, but very low levels of binding to the healthy tooth tissue. These results suggest that specific layers of the tooth can be targeted with high specificity using specific peptides.

Example 4

Preferential Binding of DSS Peptides to Carious Lesions in Teeth

Figure 5:
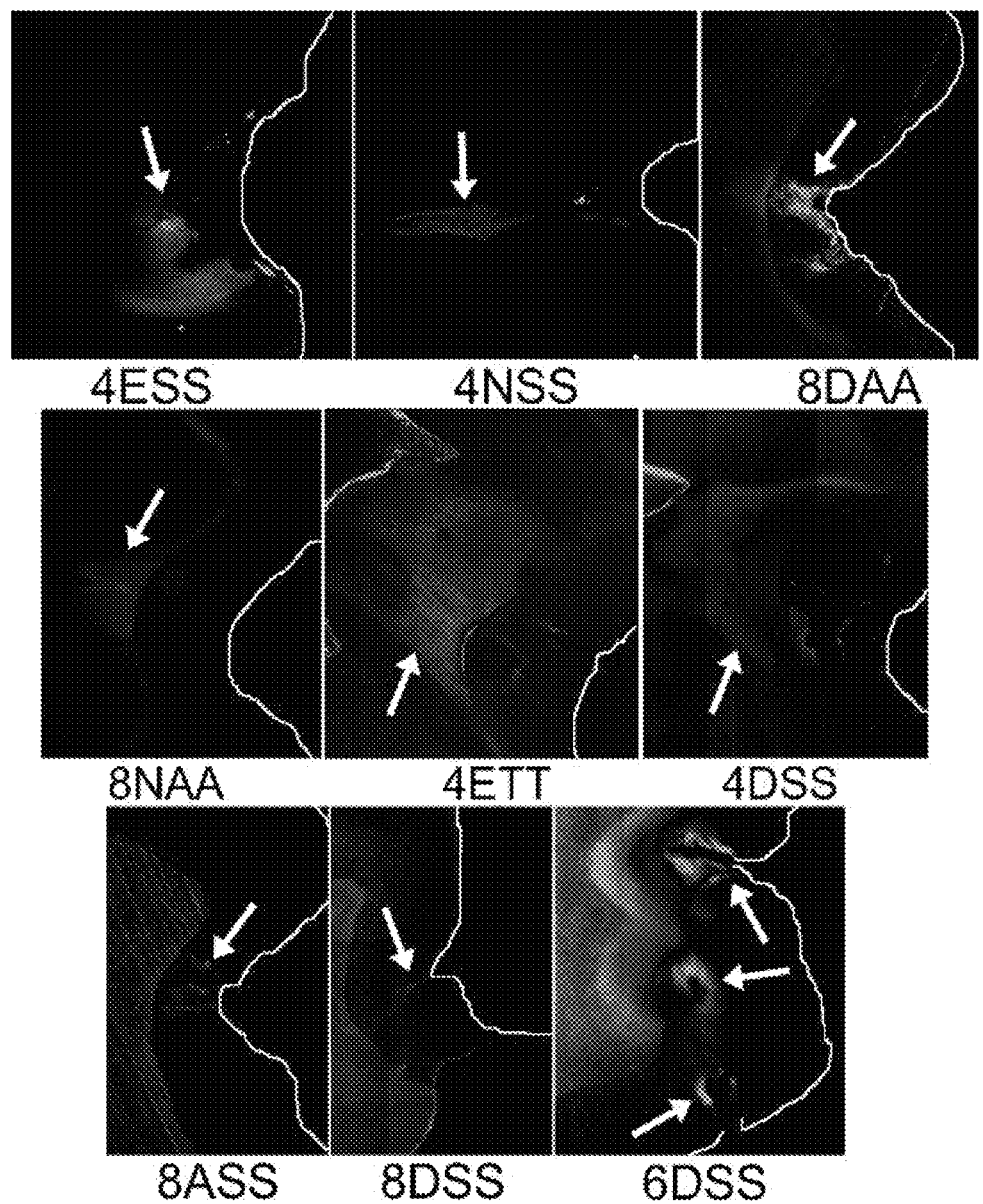
FIG. 5 provides fluorescence micrographs showing specific binding of DSS peptides and variants (4ESS=SEQ ID NO:34; 4NSS=SEQ ID NO:35; 8DAA=SEQ ID NO:40; 8NAA=SEQ ID NO:41; 4ETT=SEQ ID NO:37; 4DSS=SEQ ID NO:31; 8ASS=SEQ ID NO:26; 8DSS=SEQ ID NO:33; 6DSS=SEQ ID NO:32) to carious lesions in teeth. Adult human teeth were exposed to 12.5 µM 5(6)-carboxyfluorescein-labeled peptide without demineralization, washed extensively, and imaged by CLSM. Microscope and camera settings were optimized separately for each sample. Each panel shows a region of the tooth section encompassing a carious lesion. White traces on the right side of each panel identify the position of the tooth surface, while arrows indicate the position of the stained lesion.
Figure 6:
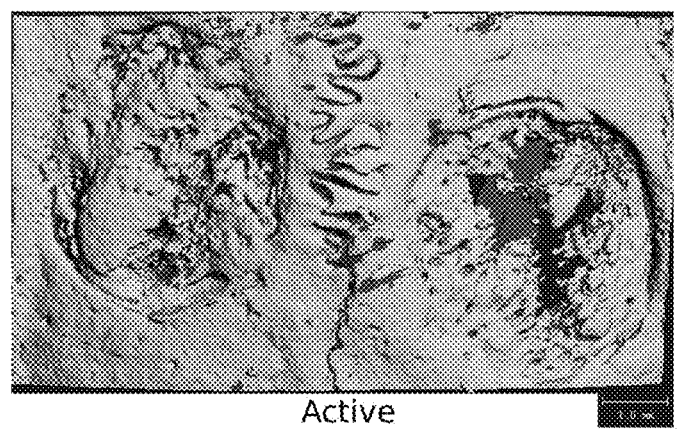
FIG. 6 illustrates that calcium-binding moieties described herein substantially increase the rate of healing in critical diameter rat calvarial defects. The micro CT shows bone deposition at 3 weeks (scale embedded in CT photo).
Figure 6:
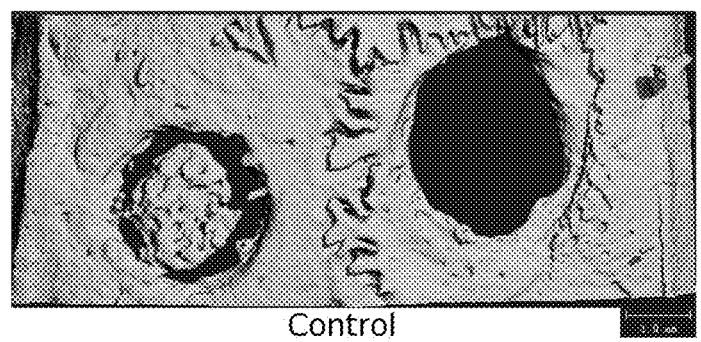

Sections of human teeth containing obvious carious lesions, which consist of demineralized enamel, were polished and exposed to 5(6)-carboxyfluorescein-labeled DSS peptides and variants. The sections were washed extensively and imaged by CLSM using blue laser illumination (λ=488 nm) and a FITC emission filter, with microscope and camera settings adjusted for each sample to optimize the signal detected from each peptide. The images were examined to identify the relative levels of peptide binding in healthy versus carious tissue. 4ESS (SEQ ID NO:34), 4NSS (SEQ ID NO:35), 8DAA (SEQ ID NO:39), 8NAA (SEQ ID NO:41), 4ETT (SEQ ID NO:37), 4DSS (SEQ ID NO:31), 8ASS (SEQ ID NO:26), 8DSS (SEQ ID NO:33), and 6DSS (SEQ ID NO:32) exhibited highly specific binding to carious lesions, with little or no binding to the surrounding healthy enamel (FIG. 5; some of these lesions are visible in FIG. 4 as well). Other peptides were not tested, but based on these results binding to carious lesions is presumed. Of these peptides, 4ESS (SEQ ID NO:34), 4NAA (SEQ ID NO:44), 8DSS (SEQ ID NO:33), 6DSS (SEQ ID NO:32), 4DSS (SEQ ID NO:31), 8DAA (SEQ ID NO:33), and 8ASS (SEQ ID NO:26) exhibited exceptionally strong staining of carious lesions with relatively weak (often completely absent) binding of surrounding enamel. The ability of these peptides to bind carious lesions, while exhibiting little or no binding to the fully mineralized surface of healthy enamel, indicate that these peptides can be used to identify dental caries or lesions of the tooth. Given their ability to remineralize at sites of enamel degradation, they can also be used to initiate remineralization at sites of enamel degradation such as caries or injury sites without causing inappropriate nucleation on healthy tissue surfaces.

Example 5

Antimicrobial Activities of DSS Peptide-Antimicrobial Compound Fusions

In order to determine the suitability of calcium-binding peptides to serve as targeting moieties to deliver therapeutic compounds to mineralized surfaces, peptides were synthesized containing an N-terminal $(DSS)_4$ (SEQ ID NO:31), $(DSS)_5$ (SEQ ID NO:22), or $(DSS)_6$ (SEQ ID NO:32) peptide, a triglycine (GGG) linker, and a 2c-4 antimicrobial peptide (RWRWRWF, SEQ ID NO:1 (SEQ ID NO:26 in WO 2007/038683)). The sequences of these fusion proteins are DSS DSS DSS DSS GGG RWRWRWF (SEQ ID NO:23), DSS DSS DSS DSS DSS GGG RWRWRWF (SEQ ID NO:24), and DSS DSS DSS DSS DSS DSS GGG RWRWRWF (SEQ ID NO:25) (see SEQ ID NOs:27-29, respectively in WO 2007/038683). The antimicrobial activity of these peptides against anaerobic planktonic bacteria was determined by a modification of a previously described assay. Briefly, *Streptococcus mutans* strain UA159 cells were diluted to ~1×10⁵ cfu/mL in Todd-Hewitt (TH) broth medium and mixed with either suspended hydroxyapatite nanocrystals (Berkeley Advanced Biomaterials, Inc., 0.03% w/v) or, for control samples, an equivalent volume of deionized water. Aliquots were transferred into 96-well plates (Fisher). Serial dilutions of the peptides were then made and added to the bacteria. The minimum inhibitory concentration (MIC) of each peptide was determined by identifying the concentration of peptide that completely inhibited bacterial growth after an incubation of approximately 24 hours, as measured by absorbance of cell suspensions at a wavelength of 600 nm. Peptide 2c-4 shows an MIC of 2 pM against planktonic *S. mutans* by itself. When conjugated to a $(DSS)_4$ (SEQ ID NO:31) moiety to generate peptide 4DSS-2c4, its MIC rises to 52.5 pM, a significant loss of efficacy that is unaffected by the addition of 0.03% (w/v) hydroxyapatite. However, as previously shown, the $(DSS)_4$ (SEQ ID NO:31) moiety shows lower affinity for hydroxyapatite than do peptides with more DSS repeats, and the high positive charge of the 2c-4 peptide may interact with the high negative charge of the $(DSS)_4$ (SEQ ID NO:31) moiety to inhibit activity somewhat. Nonetheless, some antimicrobial activity is retained by this peptide.

Alternatively, conjugation of a $(DSS)_6$ (SEQ ID NO:32) moiety to b-34 antimicrobial peptide (DSS DSS DSS DSS DSS DSS GGG LKRF LKWF KRF (SEQ ID NO:27) (SEQ ID NO:30 in WO 2007/038683) to generate peptide 6DSS-b-34 (SEQ ID NO:31 in WO 2007/038683) leads to an improvement in antimicrobial activity over that of the parent peptide (MIC=3.1 pM for 6DSS-b-34 versus 5.6 pM for b-34). Although the addition of 0.03% HA reduces the antimicrobial activity of 6DSS-b-34 somewhat, the resulting MIC of 12.5 pM still represents considerable activity against *Streptococcus mutans*. In yet another alternative, peptide PL-135 (SEQ ID NO:32 in WO 2007/038683) showed an MIC of 21 pM against planktonic *S. mutans* in medium alone. Conjugation of this peptide with a $(DSS)_5$ (SEQ ID NO:22) moiety to generate peptide 5DSS-PL135 (DSS DSS DSS DSS DSS GGG FHFHLHF (SEQ ID NO:29) ((SEQ ID NO:33 in WO 2007/038683)) reduces its antimicrobial activity against *S. mutans* to >170 pM in medium alone. Addition of 0.03% hydroxyapatite suspension to the medium lead to the recovery of much of this activity, reducing the MIC to 42.5 pM.

This shows that other compounds can maintain their activity when conjugated with DSS peptides. Further, this demonstrates that compounds can be readily generated that only have significant activity in the presence of a DSS peptide target, suggesting a facile means of developing compounds that are only active at calcified (bone, tooth, etc.) surfaces and are inert in other environments. Such compounds represent a major step forward in enhancing the safety and efficacy of therapeutic approaches to mineralized tissue disorders.

Example 6

Specific Binding and Mineralization of Calcified Surfaces by Small Peptides

Several small (<25 aa) peptides have been designed based on the sequence of the dentin phosphoprotein (DPP), one of the major noncollagenous proteins thought to be involved in the mineralization of the dentin extracellular matrix during tooth development. These peptides, consisting of multiple repeats of the tripeptide aspartate-serine-serine (DSS), bind with high affinity to calcium phosphate compounds and, when immobilized, can recruit calcium phosphate to peptide-derivatized polystyrene beads or to demineralized human dentin surfaces. The affinity of binding to hydroxyapatite surfaces increases with the number of $(DSS)_n$ repeats, and though similar repeated sequences—$(NTT)_n$, $(DTT)_n$, $(ETT)_n$, $(NSS)_n$, $(ESS)_n$, $(DAA)_n$, $(ASS)_n$, and $(NAA)_n$—also showed HA binding activity, it was generally not at the same level as the natural sequence. Binding of the $(DSS)_n$ peptides to sectioned human teeth was shown to be tissue-specific, with high levels of binding to the mantle dentin, lower levels of binding to the circumpulpal dentin, and little or no binding to healthy enamel. Phosphorylation of the serines of these peptides was found to affect the avidity, but not the affinity, of binding. The potential utility of these peptides in the detection of carious lesions, the delivery of therapeutic compounds to mineralized tissues, and the modulation of remineralization is discussed.

Materials and Methods

Peptide Synthesis

The following peptide sequences were synthesized: 2DSS (DSS DSS, SEQ ID NO:30), 4DSS (DSS DSS DSS DSS, SEQ ID NO:31), 6DSS (DSS DSS DSS DSS DSS DSS, SEQ ID NO:32), 8DSS (DSS DSS DSSDSS DSS DSS DSS DSS, SEQ ID NO:33), 4ESS (ESS ESS ESS ESS, SEQ ID NO:34), 4NSS (NSS NSS NSS NSS, SEQ ID NO:35), 4DTT (DTT DTT DTT DTT, SEQ ID NO:36), 4ETT (ETT ETT ETT ETT, SEQ ID NO:37), 4NTT (NTT NTT NTT NTT, SEQ ID NO:38), 8DAA (DAA DAA DAA DAA DAA DAA DAA DAA, SEQ ID NO:39), 8NAA (NAA NAA NAA NAA NAA NAA NAA NAA, SEQ ID NO:40), 8ASS (ASS ASS ASS ASS ASS ASS ASS ASS SEQ ID NO:26), #3-1 (LIKHIL-HRL SEQ ID NO:41).

Peptides were synthesized using standard Fmoc solid phase chemistry on an Apex 396 multiple peptide synthesizer (AAPPTec, Louisville, Ky.) at 0.015 mM scale. Completed peptides were cleaved from the resin with 95% trifluoroacetic acid and appropriate scavengers. Crude peptide was purified to 90-95% purity using reverse-phase high-performance liquid chromatography (ACTA Purifier; Amersham, Arlington Heights, Ill.), and peptide mass was confirmed by matrix-assisted laser desorption/ionization (MALDI) mass spectroscopy. Peptides for use in binding analyses were labeled with 5(6)-carboxyfluorescein prior to cleavage, and peptides for use in assays requiring peptide immobilization were C-terminally labeled with biotin immediately following the cleavage step.

HA Binding Assay

Fluorescein-labeled DSS-containing peptides of various lengths were subjected to pulldown assays as follows: Samples containing varying concentrations of fluorescein-labeled peptide (0-100 μM) and a fixed amount (0.3 mg) of HA nanocrystals with a specific surface area of 100 m²/g (Berkeley Advanced Biomaterials, Berkeley, Calif.) were prepared. Measurements were taken of the absorbance of the labeled peptide at 488 nm (the peak absorbance of the fluorescein label) before and after exposure to the HA. The amount of peptide bound was calculated by comparing the ratio of the final (Af) and initial ($A_i$) absorbances to the initial concentration ($C_0$) [$C_{bound}=(A_f/A_i)C_0$]. Plots were generated of the amount of peptide bound per meter squared of HA surface area vs. concentration of unbound peptide at equilibrium. The resulting isotherms were fit to the Langmuir isotherm, $x/m=(K_A N_{max} C_{eq})/(1+K_A C_{eq})$, where x/m represents the molar amount of peptide bound per unit of HA surface area, $K_A$ is the affinity constant of the peptide for the HA surface (L/Mol), $N_{max}$ is the maximum surface concentration (mol/m²), and $C_{eq}$ is the molar concentration of unbound peptide at equilibrium (Calis et al. (1995) *Pharm Res.,* 12: 1072-1076).

Binding of Calcium Phosphate to Immobilized DSS Peptides

Streptavidin-coated polystyrene beads with an average diameter of 4 μm (Spherotech, Lake Forest, Ill.) were incubated with either biotin-conjugated 8DSS (SEQ ID NO:33) peptide or unconjugated biotin (control beads). Beads were washed with PBS to remove unbound peptide (or unbound biotin in control beads) and incubated in a solution of PBS+1 mM $CaCl_2$+1 mM $NaHPO_4$ for 12 days prior to imaging.

Mouse Bone Marrow Culture

Mouse bone marrow cultures were grown to confluence in DMEM+10% FBS and then treated continuously for 3 weeks with either 2.5 p.M 5(6)-carboxyfluorescein-labeled 6DSS (SEQ ID NO:32) or 2.5 p.M 5(6)-carboxyfluorescein-labeled peptide #3-1 (control peptide) in α-MEM+10% FBS+50 p.g/mL ascorbic acid 4 mM β-glycerophosphate. Cultures were imaged by fluorescence microscopy using a FITC excitation/emission filter set.

Binding and Mineralization of Tooth Surfaces

Adult human molars, extracted during normal clinical practice, were sagittally sectioned (Accutom-50, Copenhagen, Denmark; CA-231 diamond blade) and demineralized with 19% ethylenediaminotetraacetic acid (EDTA) gel for 1 h, followed by immersion in deionized water and ultrasonication to remove debris. Samples were treated with either 12.5 p.M 8DSS (SEQ ID NO:33) peptide in 50 mM HEPES buffer (pH 7.0) or buffer alone (no peptide) or were left untreated for 1 h prior to remineralization with Quell Desensitizer (Pentron Technologies, Wallingford, Conn.), a remineralization solution consisting of aqueous solutions of calcium chloride and potassium phosphate, for 15 min. Samples were rinsed thoroughly prior to imaging by scanning electron microscopy.

For binding experiments, sagittally sectioned adult human molars were incubated for 10 min in a solution of 12.5 p.M 5(6)-carboxyfluorescein-labeled 6DSS (SEQ ID NO:32) peptide containing 10 mM NaCl and 50 mM HEPES, pH 7.0. Control samples were prepared without peptide. Samples were rinsed after treatment and imaged by confocal laser scanning microscopy (CLSM) with illumination by a blue Kr/Ar laser (λ=488 nm) and a FITC emission filter.

Results

Quantitative Analysis of DSS-Peptide Binding to HA Surfaces

In order to quantitatively assess the strength of the DSS-HA interaction as well as to determine the roles of peptide length and sequence on binding, fluorescein-labeled, DSS-containing peptides of various lengths were subjected to pulldown assays as described in "Materials and Methods."

Figure 7A:
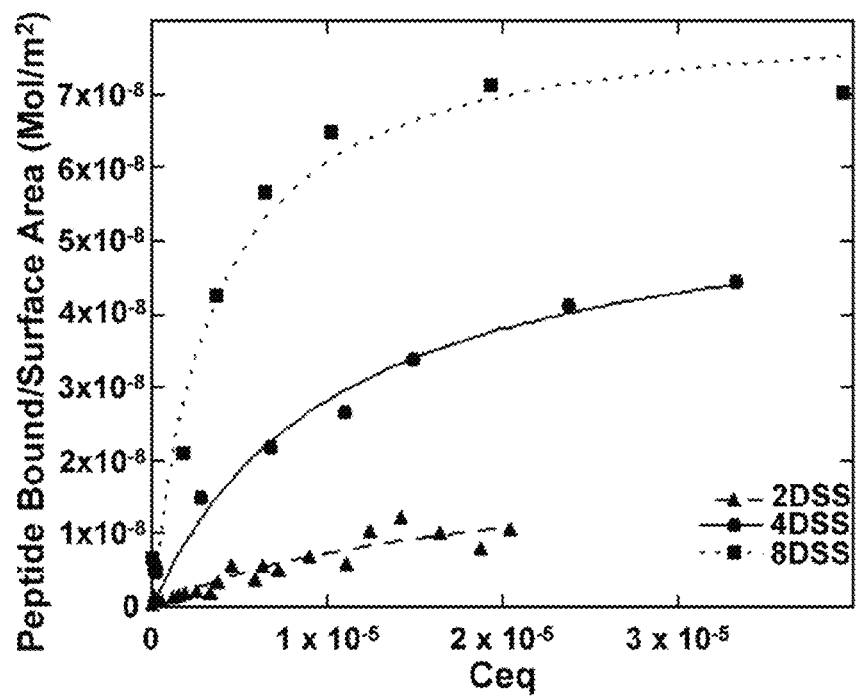
FIGS. 7A, 7B, and 7C show equilibrium isotherms for binding of selected (DSS)n-containing peptides and variants (2DSS=SEQ ID NO:30; 4DSS=SEQ ID NO:31; 8DSS=SEQ ID NO:33; 4ESS=SEQ ID NO:34; 4NTT=SEQ ID NO:38; 4DTT=SEQ ID NO:36; 8DAA=SEQ ID NO:39; 8NAA=SEQ ID NO:41; 8ASS=SEQ ID NO:26) to HA.

The experimental data were fit to the Langmuir isotherm, which describes the binding of molecules to surfaces with the conditions that (1) all binding sites have the same affinity for the peptide and (2) the peptide will form a monolayer on the surface but cannot accumulate to higher levels (Atkins (1994) *Physical chemistry.* Freeman, New York). The excellent fit of the Langmuir isotherm to the experimental data validates these conditions, and the constants obtained from this analysis were used for comparisons between peptides. As shown in FIG. 7A and summarized in Table 6, both the binding affinity ($K_A$) and the monolayer concentration ($N_{Max}$) of the various peptides increased with the number of DSS repeats per peptide. Additionally, several variant peptides were tested (FIGS. 7B, 7C, Table 6): a peptide containing a longer side chain at the first position (4ESS (SEQ ID NO:34)), peptides containing a more sterically hindered hydroxyl group at the second and third positions (4DTT (SEQ ID NO:36), 4NTT (SEQ ID NO:38), 4ETT (SEQ ID NO:37)), peptides lacking a charged group at the first position (4NSS (SEQ ID NO:35), 8ASS (SEQ ID NO:26)), and peptides lacking hydroxyl groups at the second and third positions (DAA-8 (SEQ ID NO:40), 8NAA (SEQ ID NO:41)). By comparing the affinities of these variants with those of DSS-containing peptides of the same size, it was determined that elimination of the negatively charged residue (4NSS (SEQ ID NO:35), 4NTT (SEQ ID NO:38), FIG. 7B; 8ASS (SEQ ID NO:26), FIG. 7C) resulted in significant loss of binding affinity, while replacement of the Ser residues with Thr or Ala (4DTT (SEQ ID NO:36), 4ETT (SEQ ID NO:37), FIG. 7B; DAA8 (SEQ ID NO:39), FIG. 7C) had little observable effect on this parameter (e.g., DAA-8 (SEQ ID NO:39) has a KA that is within experimental error of the KA for 8DSS (SEQ ID NO:33)). Peptides in which both the acidic residue at the first position and the serine residues at positions 2 and 3 were replaced (4NTT (SEQ ID NO:38), FIG. 7B; 8NAA (SEQ ID NO:41), FIG. 7C) led to near-total loss of binding activity.

Because binding activity is determined by both the binding affinity ($K_A$) and the maximum monolayer concentration ($N_{Max}$), peptides that show similar affinities can vary widely in their overall activity due to differences in $N_{Max}$. Thus, while the presence of a negative charge at position 1 of the repeat is clearly the key sequence parameter in determining binding affinity, these data suggest that both the acidic residues and the serines are involved in binding of these peptides to HA surfaces: Asp-Ser-Ser is the optimal sequence giving rise to HA-binding activity (due to the effect of the serines on the maximum monolayer concentration), while all of the variant peptides show markedly reduced binding to HA in vitro. Interestingly, phosphorylation of the first position of the DSS repeat-peptide 4DS(P)S (SEQ ID NO:4) did not lead to a significant change in binding affinity relative to an unphosphorylated peptide of the same size (peptide 4DSS (SEQ ID NO:31)) but rather gave a large increase in the surface binding density, suggesting an alteration in the binding mode rather than simply the affinity of the interaction (Table 6).

TABLE 6

Langmuir parameters of peptides described in this study, based on fits of the Langmuir equation to raw data.

| Peptide | SEQ ID NO: | $K_A$ (M$^{-1}$) | Nmax (mol/m$^2$) | r |
|---|---|---|---|---|
| 2DSS | 30 | 57,000 ± 24,000 | $2 \times 10^{-8} \pm 5 \times 10^{-9}$ | 0.94 |
| 4DSS | 31 | 94,000 ± 26,000 | $5.8 \times 10^{-8} \pm 6 \times 10^{-9}$ | 0.98 |
| 5DSS | 22 | 148,000 ± 14,000 | $9.2 \times 10^{-8} \pm 2 \times 10^{-9}$ | 0.99 |
| 6DSS | 32 | 272,000 ± 26,000 | $1.3 \times 10^{-7} \pm 3 \times 10^{-9}$ | 0.99 |
| 8DSS | 33 | 290,000 ± 70,000 | $8.2 \times 10^{-8} \pm 6 \times 10^{-9}$ | 0.99 |
| 4ESS | 34 | 81,000 ± 18,000 | $4.6 \times 10^{-8} \pm 4 \times 10^{-9}$ | 0.99 |
| 4NSS | 35 | 16,000 ± 4,000 | $3.0 \times 10^{-8} \pm 1 \times 10^{-9}$ | 0.99 |
| 4DTT | 36 | 161,000 ± 79,000 | $1.3 \times 10^{-8} \pm 1 \times 10^{-9}$ | 0.92 |
| 4ETT | 37 | 79,000 ± 25,000 | $8.8 \times 10^{-8} \pm 9 \times 10^{-9}$ | 0.94 |
| 4NTT | 38 | 17,000 ± 7,000 | $5.8 \times 10^{-8} \pm 2 \times 10^{-8}$ | 0.98 |
| 8DAA | 39 | 310,000 ± 74,000 | $6.0 \times 10^{-8} \pm 6 \times 10^{-9}$ | 0.99 |
| 8ASS | 26 | ND | ND | ND |
| 8NAA | 41 | ND | ND | ND |
| 4DS(P)S | 4 | 83,000 ± 9,000 | $1.2 \times 10^{-7} \pm 5 \times 10^{-9}$ | 0.99 |

Binding of DSS-Containing Cultures to Mineralizing Tissue Cultures

Figure 8:
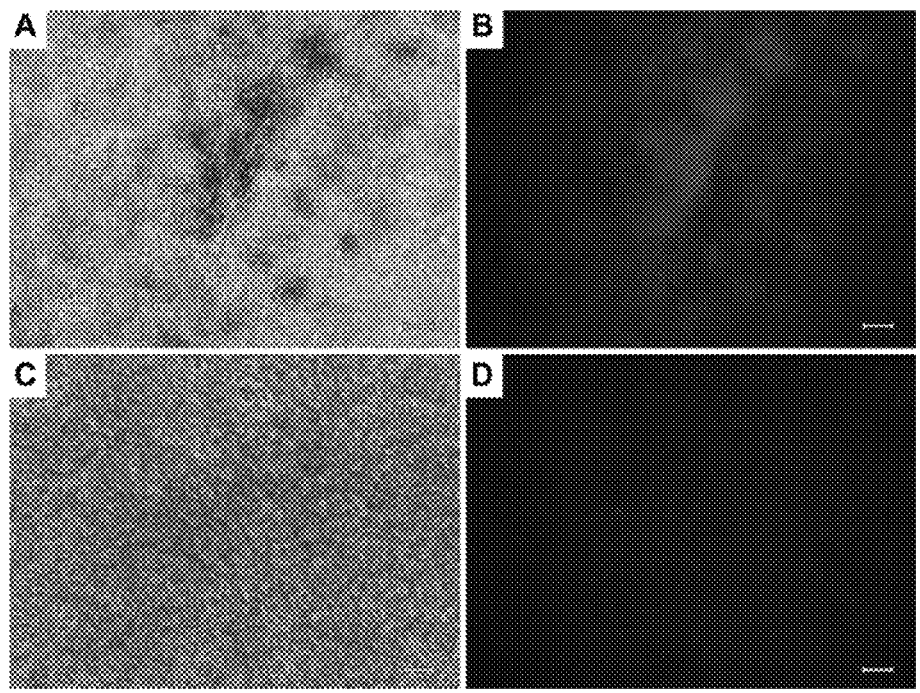
FIG. 8, panels A-D, show binding of fluorescently labeled 6DSS (SEQ ID NO:32) peptide to mineralized bone marrow nodules. MBM cultures were grown and imaged as described in Example 6. Panel A: Bright field image of mineralized mouse bone marrow nodules (MBMNs) from a culture treated with 6DSS (SEQ ID NO:32). Panel B: Fluorescence image of the field shown in panel A. Panel C: Bright field image of mineralized MBMNs from a culture treated with scrambled control peptide. Panel D: Fluorescence image of the field shown in panel C. Bars=600 µm.

Having established that (DSS)n-containing peptides are able to actively bind HA, we sought to determine whether they would bind to emerging sites of mineralization in biologically derived tissue. Mouse bone marrow (MBM) cultures, cultured under osteogenic conditions, were treated continuously for 3 weeks with either labeled 6DSS (SEQ ID NO:32) peptide or labeled peptide #3-1 (non-calcium-binding control peptide). Cultures were imaged by fluorescence microscopy using a FITC excitation/emission filter set. FIG. 8, panel B shows bright staining of the mineralizing MBM nodules in the DSS-treated sample, with no binding seen in the control sample (FIG. 8, panel D), indicating not only that the labeled 6DSS (SEQ ID NO:32) peptide binds to mineralizing nodules in MBM cultures but also that this binding is a property of the DSS sequence, rather than a general property of small peptides.

Binding of Amorphous Calcium Phosphate by DSS-Containing Peptides

Figure 9:
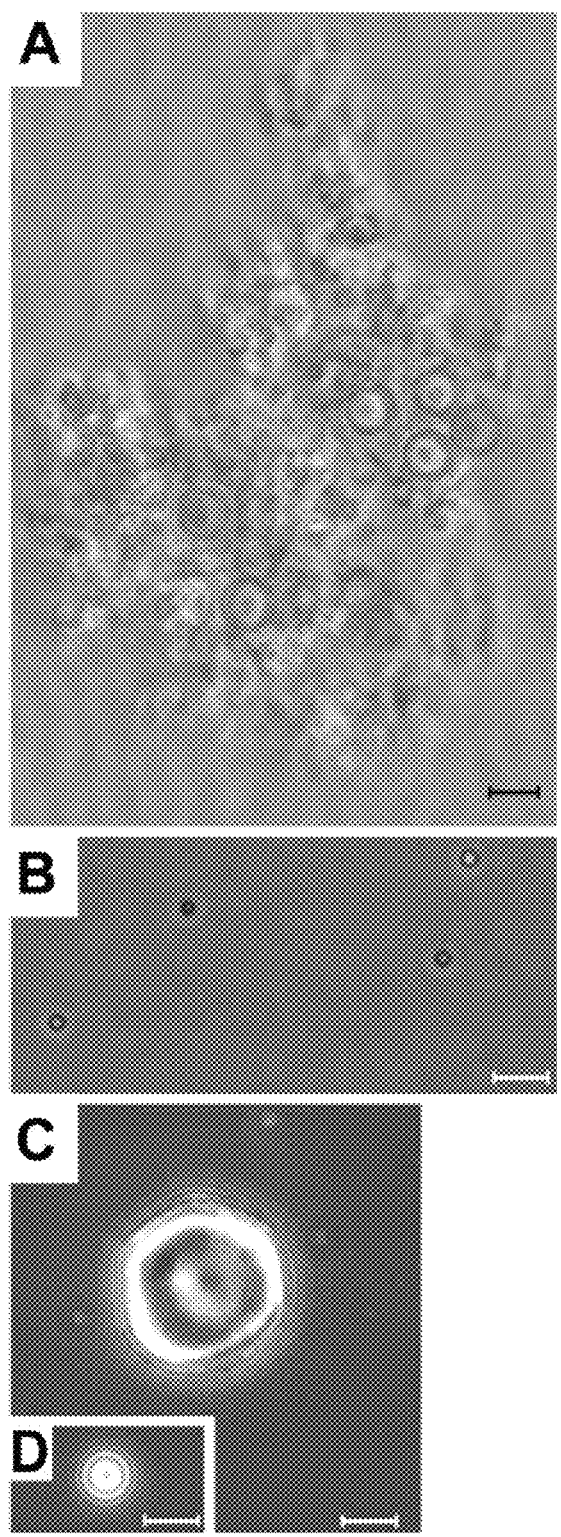
FIG. 9, panels A-D, show the interaction of immobilized 8DSS (SEQ ID NO:33) peptide with $CaHPO_4$. Streptavidin-coated polystyrene beads (4 µm average diameter) were incubated with either biotin-conjugated 8DSS (SEQ ID NO:33) peptide (Panels A, C) or unconjugated biotin (Panels B, D). Panel A: Bright field micrographs of amorphous calcium phosphate aggregates accumulated around DSS-coated beads. Bar=4 µm. Panel B: Bright field image of representative biotin-blocked beads (no DSS peptide). Bar=12 µm. Panel C: Phase-contrast micrograph of a DSS-coated bead with a more ordered accretion of calcium phosphate around its exterior. Bar=4 µm. Panel D: Control sample (biotin-blocked, no DSS peptide). Bar=4 µm.

To test the ability of DSS-containing peptides to recruit calcium phosphate and to nucleate crystal growth, 25 μM 6DSS peptide was combined with varying concentrations of $CaCl_2$ and $NaHPO_4$ and incubated as described in "Materials and Methods." Though it was expected that the presence of the free DSS-containing peptide would enhance the formation of HA crystals at subcritical $CaHPO_4$ concentrations, this was not observed (data not shown). DSS-containing peptides containing C-terminal biotin labels were then synthesized and immobilized on streptavidin-coated beads. The beads were washed and incubated in solutions containing varying concentrations of $CaHPO_4$ as before. Consistent with previous observations for the dentin phosphoproteins/phosphophoryns as well as other phosphoproteins (Saito et al. (1997) Bone 21: 305-311; Saito et al. (2000) J Bone Miner Res., 15: 1615-1619), these immobilized peptides caused coaggregation of the beads with particles of amorphous $CaHPO_4$ and eventually led to the deposition of crystalline material around the bead. As illustrated in FIG. 9, panel A, nearly all peptide-coated beads were incorporated into large aggregates of precipitated amorphous calcium phosphate. By comparison, in the biotin-blocked control sample, nearly all beads were unaggregated and unassociated with precipitate (FIG. 9, panel B). Interestingly, several peptide-coated beads became covered with more ordered layers of mineral during the experiment (a representative is shown in FIG. 9, panel C), while all of the uncoated/biotin-blocked control beads failed to accumulate mineral (FIG. 9, panel D).

Tissue-Specific Binding of DSS Peptides to Tooth Surfaces

Figure 10:
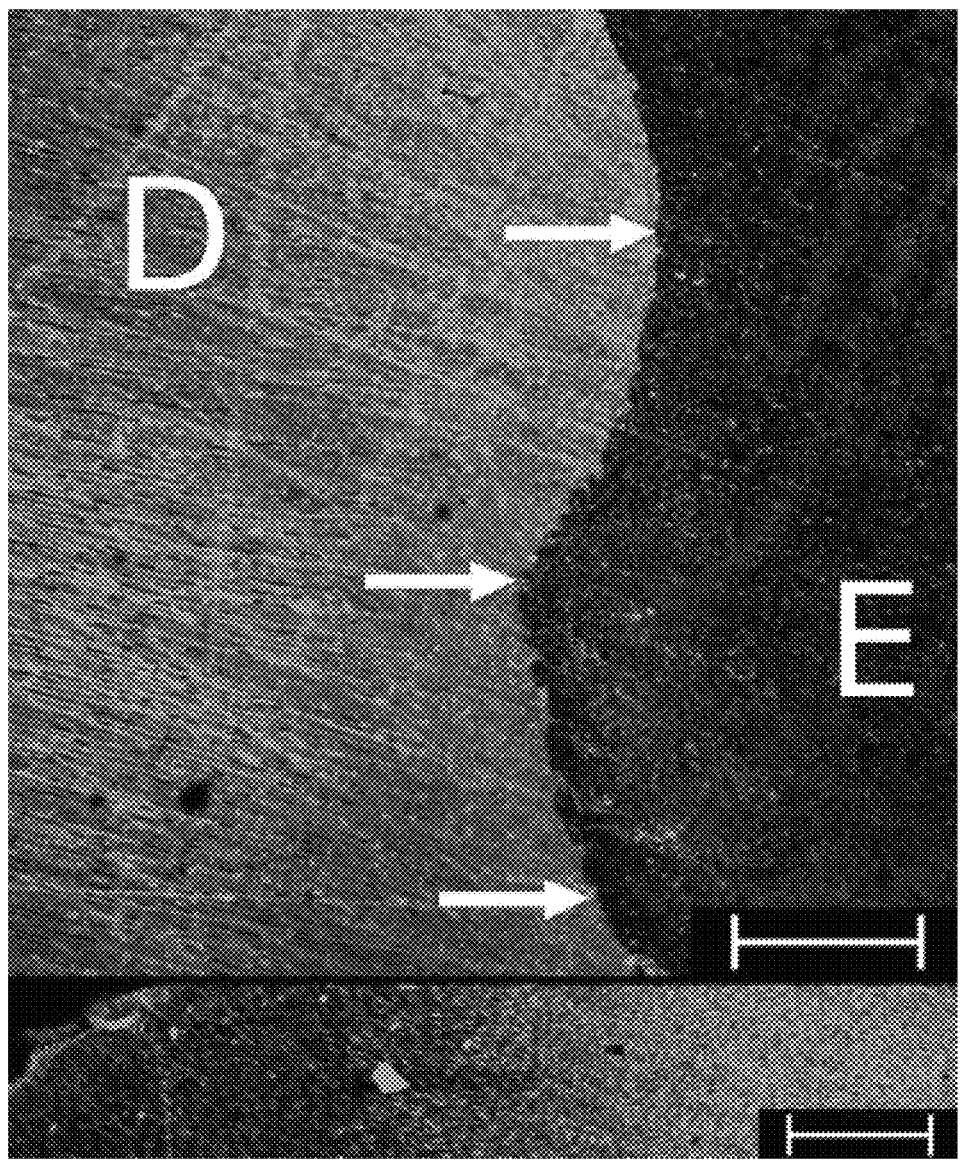
FIG. 10 shows binding of labeled DSS to dentin in human teeth. Top: Confocal image of fluorescently labeled $(DSS)_8$ (SEQ ID NO:33) peptide to a sectioned human tooth, showing the enamel (E) and the dentin (D). Arrows indicate the DEJ. Bottom: Confocal image of the same tooth, in the region between the mantle dentin (right) and the pulp cavity (left), showing preference of this peptide for mantle dentin over circumpulpal dentin and enamel. Bars=50 µm.

To test binding of DSS-containing peptides to biological tissue, sagittally sectioned human teeth were incubated treated with 6DSS (SEQ ID NO:32) (control samples were prepared without peptide), washed, and imaged by CLSM. FIG. 10 shows the intense fluorescent staining of the tooth by the labeled peptide. Mock-treated control sections stained either with scrambled peptide or with free 5(6)-carboxyfluorescein showed no fluorescence (not shown). Interestingly, this peptide specifically binds to the dentin as no binding to the enamel was seen (the leftmost edge of the stained area in FIG. 10 corresponds to the dentin-enamel junction [DEJ]). Examining the spatial pattern of dentin binding by labeled 6DSS (SEQ ID NO:32) (FIG. 10) reveals that staining is brightest in the mantle dentin nearest the DEJ, with noticeably lower levels of staining in the circumpulpal dentin, near the pulp cavity.

DSS-Mediated Remineralization of Tooth Surfaces
In vitro

Figure 11:
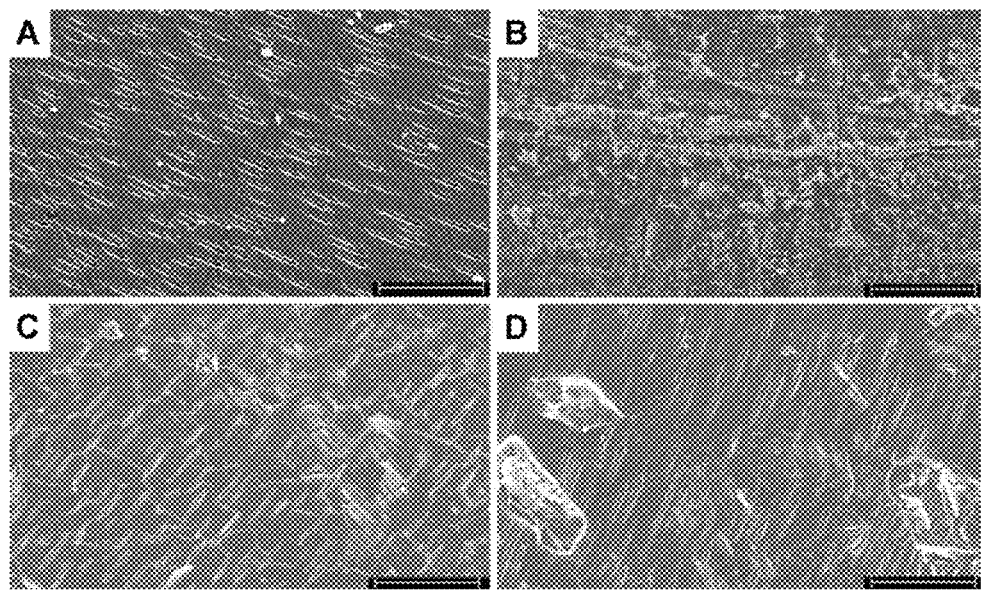
FIG. 11, panels A-D, show scanning electron micrographs of sagittal tooth sections, treated as indicated: Panel A: untreated control; Panel B: pretreated with 8DSS (SEQ ID NO:33) for 1 h, rinsed, and remineralized using Quell desensitizer; Panel C: preincubated with buffer (50 mM HEPES, pH 7.0), followed by remineralization as in panel B; Panel D: no preincubation, remineralization as in panel B. Bars=50 µm.

Having established that $(DSS)_n$-containing peptides can bind to the dentin surface and that immobilized peptides could cause the accretion of calcium phosphate, we sought to determine whether these peptides could be used to recruit calcium phosphate to the dentin surface. Demineralized sections of extracted human teeth were treated with 8DSS (SEQ ID NO:33) peptide and then subjected to remineralization with Quell Desensitizer (Pentron Technologies), a commercially available remineralization product consisting of aqueous solutions of calcium chloride and potassium phosphate. As shown in the electron micrographs in FIG. 11, mock-treated (FIG. 11, panel C) and untreated samples (treated with desensitizer only, FIG. 11, panel D) showed low levels of mineral accumulation, with several dentinal tubules remaining exposed. In contrast, DSS-treated dentin samples (FIG. 11, panel B) accumulated a continuous layer of calcium phosphate precipitate in the presence of desensitizer solution, fully occluding the dentinal tubules.

Discussion

Biomineralization is one of the central processes in vertebrate development and evolution (Kawasaki et al. (2004) *Proc. Natl. Acad. Sci., USA,* 101: 11356-11361) and references within, affecting processes as diverse as feeding, locomotion, predator avoidance, hearing, and balance. Defects in mineralization or mineralized tissue proteins are involved in human maladies ranging from hereditary deafness (Xiao et al. (2001) *Nat. Genet.,* 27: 201-204) and atherosclerosis (Magne et al. (2005) *Bioessays* 27: 708-716) to dental caries and osteoporosis. Proteins that mediate the mineralization process offer us a template for understanding how to manipulate the deposition of calcium compounds and thus potentially enhance the treatment of calcified tissue defects.

The ubiquitous presence of DPP at sites of calcium phosphate deposition in mammals suggests that this protein plays a direct role in the mineralization process (Hao et al. (2004) *Bone* 34: 921-932; Rahima et al. (1988) *J Histochem Cytochem.,* 36: 153-157; Begue-Kirn et al. (1998) *Eur J Oral Sci.,* 106: 963-970; Bleicher et al. (1999) *Matrix Biol.,* 18: 133-143; Baba et al. (2004) *Eur J Oral Sci.,* 112: 163-170). Biochemical studies have shown that DPP can indeed affect the formation of biologically relevant HA crystals by causing nucleation (at low concentrations) or inhibition (at high concentrations) of crystal growth (Lussi et al. (1988) *Arch Oral Biol.,* 33: 685-691; Saito et al. (2000) *J Bone Miner Res.,* 15: 1615-1619). Proteins involved in mineralization processes in vertebrates (including DPP) often contain negatively charged, Asp- or Glu-rich domains (Harris et al. (2000) *Bone* 27: 795-802, and references within). This observation combined with computational and biochemical studies of the $(DSS)_n$ repeat region (Veis et al. (1998) *Eur J Oral Sci.,* 106(*Suppl* 1): 234-238; Lee and Veis (1980) *Int J Pept Protein Res.,* 16: 231-240; George et al. (1996) *J Biol. Chem.,* 271: 32869-32873; Chang et al. (2006) *Calcif Tissue Int.,* 78: 55-61) indicated that this short repeated sequence governs the mineral binding and nucleation activity of DPP.

Given the known dependence of DPP activity on its phosphorylation state (Saito et al. (1997) *Bone* 21: 305-311; He et al. (2005) *J Biol. Chem.,* 280: 33109-33114), it was not surprising that unphosphorylated DSS-containing peptides failed to nucleate HA formation in free solution. However, we found that even in the absence of phosphorylation, these peptides bound tightly and specifically to calcium phosphate compounds, suggesting that the $(DSS)_n$ motif itself may be useful in identifying, illuminating, and manipulating calcified surfaces.

In characterizing the behavior of these molecules, it was found that the binding affinities measured for the DSS peptides compare favorably with affinities measured for other known HA-binding proteins and peptides. For example, the HA binding affinity of the 8DSS (SEQ ID NO:33) peptide (290,000 $M^{-1}$), which consists of 24 amino acids, is only sevenfold less than that of fully assembled amelogenin nanospheres (1,970,000 M 1 $M^{-1}$) (Bouropoulos and Moradian-Oldak (2003) *Calcif. Tissue Int.,* 72: 599-603), which consist of up to 40 individual ~25-kDa subunits. Additionally, the C-terminal region of amelogenin is reported to have an HA-binding affinity of 6,200 $M^{-1}$ (Aoba et al. (1989) *J Dent Res.,* 68: 1331-1336), while in contrast, the similarly sized 4DSS (SEQ ID NO:31) peptide has an affinity of 94,000 $M^{-1}$. The binding affinity of 8DSS (SEQ ID NO:33) compares favorably with measured values for the comparably sized histatins (K=353,000-1,903,000 $M^{-1}$ Yin et al. (2003) *Arch Oral Biol.,* 48: 361-368), a class of small antimicrobial peptides that are known to bind HA with high affinity.

Binding of DSS-containing peptides to defined HA substrates depends strongly on the length of the peptides, with the affinity increasing in proportion to peptide size up to a length of six repeats (18 amino acids), with little additional increase in affinity seen in peptides with eight repeats (Table 6). Six repeats thus appears to be optimal for interaction with HA surfaces, possibly reflecting the maximum number of functional groups from the peptide that can effectively interact with the surface at a given time. On the other end of the length scale, the 2DSS (SEQ ID NO:30) peptide, containing only two repeats of the DSS sequence, shows an HA binding affinity much lower than that of the longer variants (57,000 $M^{-1}$), but well above values observed for the binding of individual amino acids (5,000-13,200 $M^{-1}$ for phosphoserine (Moreno et al. (1984) *Calcif Tissue Int.,* 36: 48-59; Benaziz et al. (2001) *J Colloid Interface Sci.,* 238: 48-53), 220 $M^{-1}$ for Asp (Moreno et al. (1984) *Calcif Tissue Int.,* 36: 48-59), 206 $M^{-1}$ for glutamic acid (Kresak et al. (1977) *J Colloid Interface Sci.,* 59: 283-292).

Figure 7B:
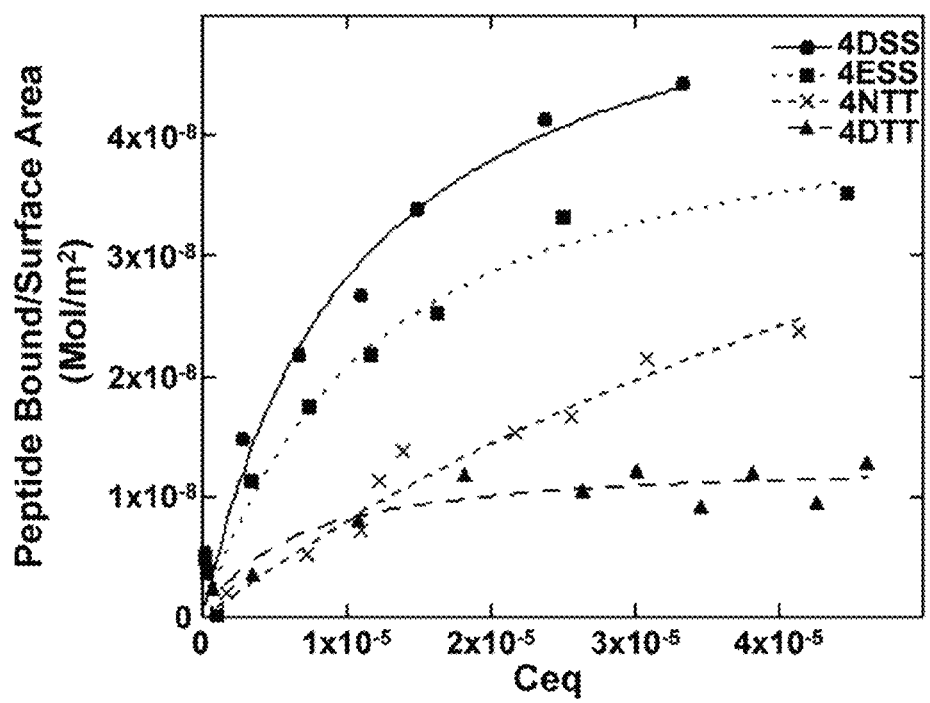
Figure 7C:
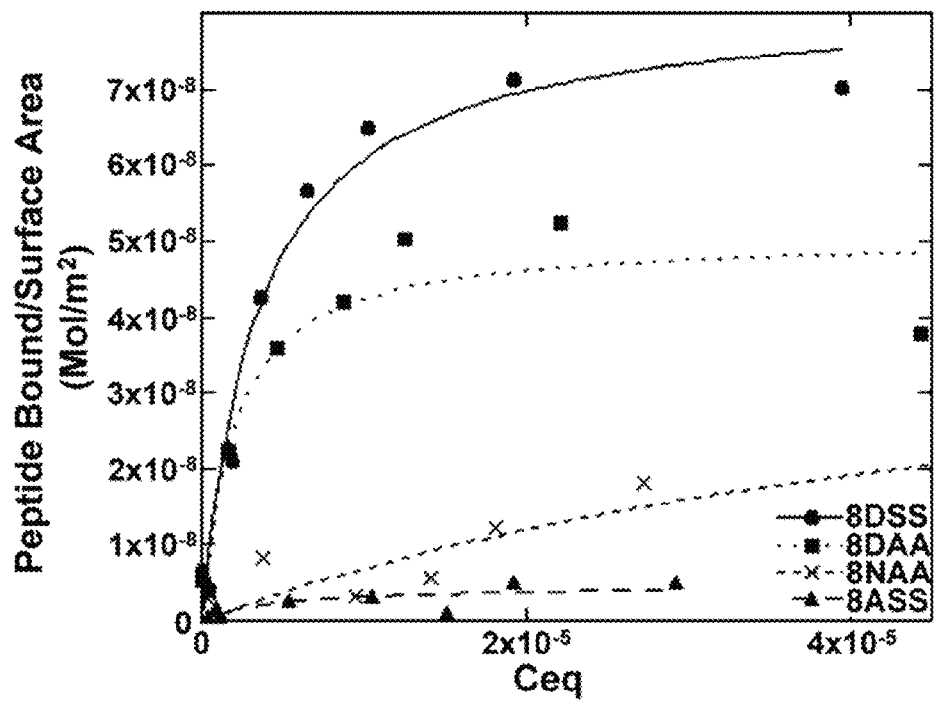

Peptide binding to HA surfaces also depended on their sequence, with nearly all variant peptides showing significant reductions in binding affinity relative to the parent DSS sequence (Table 6, FIGS. 7B, 7C). Our results show that the primary sequence determinant of binding is a negative charge at position 1 of the repeat. Studies of extremely large polymers of aspartic acid show a very high HA binding affinity (3,000,000 $M^{-1}$ for a 28.8-kDa polymer (Tsortos and Nancollas (1999) *J Colloid Interface Sci.,* 209: 109-115)). Substitutions of the serines in the DSS repeat also lead to reductions in binding activity, albeit much less severely. In the past, measurements of the binding affinity of serine to HA have ranged from those too low to subject to Langmuir analysis (Benaziz et al. (2001) *J Colloid Interface Sci.,* 238: 48-53) to much higher values (317,000 $M^{-1}$, but with a very small number of binding sites per meter squared of HA (Moreno et al. (1984) *Calcif Tissue Int.,* 36: 48-59)) depending on the specific HA preparation used, suggesting the possibility of a complex and possibly highly specific interaction between serine and discrete regions of HA surfaces. Our initial experiments indicate that binding of DSS-containing peptides to HA results primarily from the contributions of the aspartic acid residues, with the serines playing a smaller but still significant role.

Binding of (DSS)$_n$-containing peptides to defined HA surfaces in vitro led us to investigate the binding of these peptides to calcified biological tissues. Fluorescein-labeled 8DSS (SEQ ID NO:33) peptide binds tightly to the dentin of extracted adult human molars with remarkable tissue specificity, binding primarily to the mantle dentin, with binding to the enamel almost completely absent. It should be noted that the HA crystals of the dentin show very different morphologies from those of the enamel, consisting of smaller, platelike crystals with essentially random orientations, rather than the elongated, well-oriented HA crystals of the enamel surface (Paine et al. (2005) *J Biol Chem.*, 280: 31991-31998; Bath-Balogh and Fehrenbach (2006) *Dental embryology, histology, and anatomy*. Elsevier Saunders, St. Louis). Thus, it is possible that the binding specificity of (DSS)$_n$-containing peptides to regions of the dentin may be due to selective binding of this specific HA crystal form or (especially in light of the observed binding to amorphous calcium phosphates) may reflect a simple preference of these peptides for less ordered surfaces. Binding was also observed to mineralizing mouse bone marrow nodules, further indicating that these peptides may be useful in identifying and manipulating a wide variety of mineralized tissues.

Though the unphosphorylated DSS-containing peptides examined in this study failed to nucleate HA formation in free solution, they were able to effectively bind amorphous calcium phosphate aggregates. By immobilizing these peptides on a solid support, we were able to harness this ability as a means of controlling the site of calcium phosphate deposition in saturated solutions. Polystyrene beads with 8DSS (SEQ ID NO:33) peptide immobilized on their surfaces were found to effectively aggregate amorphous calcium phosphate from saturated CaHPO$_4$ solutions. Upon further incubation, however, single beads were found to accrete layers of more ordered, crystalline calcium phosphate, even without phosphorylation of the peptides. This unexpected behavior marks a departure from what has been observed for the DPP protein and suggests that the full-length protein likely contains additional regulatory mechanisms to help govern HA nucleation. This result also suggests that the (DSS)$_n$-containing peptides can be enormously versatile in manipulating the deposition of calcium phosphate.

Our investigations of the ability of (DSS)$_n$-containing peptides to initiate mineral deposition on tooth surfaces revealed that pretreatment with 8DSS (SEQ ID NO:33) peptide markedly enhanced the effectiveness of a commercially available remineralization product in causing the aggregation of mineral at the surface of partially demineralized dentin. Molecular dynamics simulations using theoretical Asp/Ser and Asp/phosphoserine-rich peptides have shown that these peptides likely adopt extended conformations, presenting functional groups on either side of a plane parallel to the interaction surface (George et al. (1996) *J Biol Chem.*, 271: 32869-32873; Dahlin et al. (1998) *Eur J Oral Sci.*, 106(Suppl 1): 239-248). In the specific case of peptides based on the Asp-Ser-Ser repeat, this has the effect of providing two equivalent mineral binding faces, allowing surface-immobilized peptides to actively bind passing amorphous calcium phosphate particles, thus leading to the observed increase in amorphous calcium phosphate accumulation on 8DSS (SEQ ID NO:33) pretreated HA surfaces. This activity presents these peptides as promising alternatives for enhancing tooth remineralization.

The ability to specifically bind to calcified surfaces and to recruit calcium phosphate offers many other unique opportunities for diagnostic and therapeutic interventions. While these activities resided in large proteins, it was not practical to contemplate their use in clinical applications; but the present demonstration of similar behavior by readily synthesized small peptides provides the possibility of powerful new tools to diagnose and treat disorders of calcified tissues. We have already presented the example of enhancing the effectiveness of existing remineralization regimens by pretreatment of surfaces with (DSS)$_n$-containing peptides, and many other possibilities remain to be explored. Current methods of diagnosing dental caries, e.g., rely on manual probing, colorimetric staining, or laser-based fluorimetry or interferometry to identify the sites of carious lesions (Audette et al. (2004) *Biochemistry* 43: 11427-11435; Tranaeus et al. (2005) *Community Dent Oral Epidemiol.*, 33: 265-273). Given the affinity of the (DSS)$_n$ peptides for amorphous calcium phosphate and their lack of binding to healthy enamel, fluorescently labeled (DSS)$_n$ peptides could possibly be used to rapidly identify carious and pre-carious lesions in teeth. This method would have far greater precision than colorimetric dyes (reliance on which can lead to the removal of healthy enamel (Yip et al. (1994) *Br Dent J.*, 176: 417-421)) and improved sensitivity compared to radiography or fluorescence-based methods that rely on native tissue fluorescence.

Because (DSS)$_n$-containing peptides can readily be attached to any number of labels or accessory compounds, their usefulness in diagnostic applications is limited only by the range of their tissue specificity. We have made extensive use of fluorescently labeled peptides in this study, but it is also possible to attach iodinated compounds for use as radiographic contrast agents (Lee et al. (2003) *J Anat.*, 203: 161-172) as well as spin-labeled tags to enhance contrast in magnetic resonance imaging. Yokogawa et al. (2001) *Endocrinology* 142: 1228-1233, showed that it was possible to target estradiol to calcified tissues by attaching it to short chains of polyaspartate. Similarly, it is possible to attach therapeutic compounds, such as antimicrobials or growth factors, to (DSS)$_n$-containing peptides in order to target their delivery to specific calcified surfaces with even greater precision.

Currently, efforts are under way to identify the range of tissue specificity of these peptides and to engineer variants with expanded or narrowed specificity that will allow us to take advantage of their mineral binding activity in more precise ways. The DPP is composed in large part of (DSS)$_n$ repeats and exerts powerful effects on the rate and type of mineralization in developing teeth (Paine et al. (2005) *J Biol. Chem.*, 280: 31991-31998). By applying the tools of peptide engineering to DPP-derived (DSS)$_n$-like peptides, we will unlock the full potential of this unique mineral-binding motif.

Example 7

Calcium-binding Agents Induce Nail Growth

New Zealand White rabbits had their paws shaved and their nails trimmed to a uniform length with respect to the visible aspect of new growth within the nail, and each digit was treated either with (D)-8DSS peptide in Dioctyl Sulfosuccinate (Aerosol OT or AOT)/isopropanol water-in-oil (W/O) nanoemulsion (formulation A1D), with (D)-8DSS peptide in DiMethylSulfOxide (DMSO, formulation D1D), or with phosphate buffered saline solution (PBS) every three days for 19 days, as described below.

Two formulations were tested, both incorporating the D form of 8DSS: A1D (Aerosol OT/Isopropanol) and D1D (DMSO Solution). In addition, negative controls were included, consisting of topical normal saline solution. Two animals were used, and eight sites were treated on each animal: on each foot, the nail beds of two digits were treated with the sample compound, while the nail beds of the remaining two digits were treated with normal saline solution. On one animal, the first and second digits were treated with the active compound while the third and fourth digits were treated with a control solution (normal saline); on the other animal this pattern is reversed in order to control for position-specific effects within the paw. At the end of the experiment, the feet of the animals were photographed and the photographs subjected to image analysis to determine the effect, of the test formulations on either the extent or the rate of nail growth. Details of the setup are shown in Table 7.

TABLE 7

| Treatment setup. | | |
|---|---|---|
| Treatment formulations: | | |
| Sample Name | Formulation | |
| A1D | AOT reverse micelles containing 20 mM (D)-8DSS peptide resuspended in 2-propanol. Effective peptide concentration in formulation is 100 µM. Applied topically. | |
| D1D | (D)-8DSS dissolved in DMSO to a concentration of 200 µM. Applied topically. | |
| C2 | Negative control. Normal saline solution applied topically | |
| Treatment: | | |
| Limb | Digits | Treatment |
| Right Foreleg | 1, 2 | A1D administered topically to the nail bed every other day |
| | 3, 4 | PBS administered topically to the nail bed every other day |
| Left Foreleg | 1, 2 | D1D administered topically to the nail bed every other day |
| | 3, 4 | PBS administered topically to the nail bed every other day |
| Right Hindleg | 1, 2 | D1D administered topically to the nail bed every other day |
| | 3, 4 | PBS administered topically to the nail bed every other day |
| Left Hindleg | 1, 2 | A1D administered topically to the nail bed every other day |
| | 3, 4 | PBS administered topically to the nail bed every other day |

At the beginning of the experiments, nails were scratched at the cuticle to indicate the position of nail growth prior to drug administration.

Topical formulations were administered to the nail bed, 20 ⌈ l per administration, every other day.

Animals were maintained according to standard husbandry guidelines and observed for any obvious defects in behavior or general health. Any skin irritation was noted.

At the end of the experiment, feet were photographed from multiple angles as necessary to show the extent of nail growth as well as any thickening or gross morphological changes on each digit; measurements were made by quantitative analysis of the images. Nails were scratched again to indicate the position of nail growth at the end of the experiment.

On day 19, images were recorded and each nail was measured. As shown in FIG. 12, treated nails showed significantly more growth than untreated nails. Aggregate measurements from the study show significant increases in nail growth for D1D-treated nails than for A1D-treated nails, and both treatment groups showed 4-fold to 5-fold greater growth over the 19-day test period than untreated or mock-treated nails (FIG. 13).

The nanoemulsion developed for hair growth applications functions well to deliver the compound as well to the nail matrix, while DMSO solutions of the active compound, found to be only marginally effective in fostering hair growth, appear to provide the most robust growth of nails. This is likely due to the propensity for vesicles from nanoemulsions to accumulate in hair follicles, while DMSO solutions deliver their solutes in a more dispersed manner throughout the tissue on which they are applied.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A formulation for inducing hair growth or inhibiting hair loss and/or inducing nail growth in a mammal, said formulation comprising:
a "D" peptide comprising the amino acid sequence (X-Y-Z)$_n$, wherein X is an amino acid selected from the group consisting of aspartic acid, glutamic acid, asparagine, and glutamine, Y and Z are amino acids independently selected from alanine, serine, and threonine, and n is a number from 2 to 100;
wherein said peptide is not phosphorylated, and wherein said peptide induces hair or nail growth when topically applied to a mammal; and
a carrier for topical application to the skin or nails of a mammal, where said formulation permits said peptide to induce hair growth and/or inhibit hair loss and/or induce nail growth when topically applied to the skin or nails of a mammal.

2. The formulation of claim 1, wherein X-Y-Z is selected from the group consisting of Asp-Ala-Ala, Asp-Ala-Ser, Asp-Ala-Thr, Asp-Ser-Ala, Asp-Ser-Ser, Asp-Ser-Thr, Asp-Thr-Ala, Asp-Thr-Ser, Asp-Thr-Thr, Glu-Ala-Ala, Glu-Ala-Ser, Glu-Ala-Thr, Glu-Ser-Ala, Glu-Ser-Ser, Glu-Ser-Thr, Glu-Thr-Ala, Glu-Thr-Ser, Glu-Thr-Thr, Asn-Ala-Ala, Asn-Ala-Ser, Asn-Ala-Thr, Asn-Ser-Ala, Asn-Ser-Ser, Asn-Ser-Thr, Asn-Thr-Ala, Asn-Thr-Ser, Asn-Thr-Thr, Gln-Ala-Ala, Gln-Ala-Ser, Gln-Ala-Thr, Gln-Ser-Ala, Gln-Ser-Ser, Gln-Ser-Thr, Gln-Thr-Ala, Gln-Thr-Ser, and Gln-Thr-Thr.

3. The formulation of claim 1, wherein said peptide ranges in length up to 100 amino acids.

4. The formulation of claim 3, wherein, wherein n is a number from 2 to 8.

5. The formulation of claim 3, wherein, wherein X is aspartic acid.

6. The formulation of claim 3, wherein Y and Z are serine.

7. The formulation of claim 3, wherein:
X is aspartic acid; and
Y and Z are serine.

8. The formulation of claim 7, wherein said peptide comprises an amino acid sequence selected from the group consisting of 4DSS (SEQ ID NO:31), 5DSS (SEQ ID NO:22), 6DSS (SEQ 10 NO:32), 7DSS (SEQ ID NO:28), 8DSS (SEQ ID NO:33), 9DSS (SEQ ID NO:42), and 10DSS (SEQ ID NO:43).

9. The formulation of claim 7, wherein the amino acid sequence of said peptide consists of a sequence selected from the group consisting of 4DSS (SEQ ID NO:31), 5DSS (SEQ ID NO:22), 6DSS (SEQ 10 NO:32), 7DSS (SEQ ID NO:28), 8DSS (SEQ ID NO:33), 9DSS (SEQ ID NO:42), and 10DSS (SEQ ID NO:43).

10. The peptide formulation according to any one of claims 8-9, wherein said peptide bears a protecting group.

11. The formulation according to any one of claims 8-9, wherein said carrier comprises an emulsion.

12. The formulation of claim 11, wherein said emulsion is a water-in-oil emulsion.

13. The formulation of claim 11, wherein said emulsion is an oil-in-water emulsion.

14. The formulation according to any one of claims 8-9, wherein said peptide is attached to a calcium phosphate nanoparticle or microparticle.

15. The formulation of claim 14, wherein said nanoparticle or microparticle comprises a calcium phosphate selected from the group consisting of hydroxyapatite, beta tricalcium phosphate, octacalcium phosphate and dicalcium phosphate dehydrate.

16. The formulation of claim 14, wherein said nanoparticle or microparticle ranges in size from about 1 nm to about 1 μm.

17. The formulation according to any one of claims 8-9, wherein said formulation comprises a product selected from the group consisting of a shampoo, a hair conditioner, a hair detangler, a hair coloring agent, a hair growth tonic, sunscreen, cream, gel, or salve, a rinse, a tonic, a solution, an emulsion, a foam, a cream, a gel, an ointment, a dusting powder, a liniment or balm, a lotion, and an ointment.

18. The formulation according to any one of claims 8-9, wherein said formulation comprises a product selected from the group consisting of a nail a nail polish, a nail strengthener, a hoof balm, a varnish, a hoof or nail glue, a sealant, a cream, a lotion, a foot bath, and a hoof bath.

* * * * *

SEQUENCE LISTING

```
<160> NUMBER OF SEQ ID NOS: 44

<210> SEQ ID NO 1
<211> LENGTH: 7
<212> TYPE: PRT
<213> ORGANISM: Artificial Sequence
<220> FEATURE:
<223> OTHER INFORMATION: synthetic antimicrobial peptide 2c-4

<400> SEQUENCE: 1

Arg Trp Arg Trp Arg Trp Phe
1               5

<210> SEQ ID NO 2
<211> LENGTH: 7
<212> TYPE: PRT
<213> ORGANISM: Artificial Sequence
<220> FEATURE:
```

```
<223> OTHER INFORMATION: synthetic antimicrobial peptide PL135

<400> SEQUENCE: 2

Phe His Phe His Leu His Phe
1               5

<210> SEQ ID NO 3
<211> LENGTH: 11
<212> TYPE: PRT
<213> ORGANISM: Artificial Sequence
<220> FEATURE:
<223> OTHER INFORMATION: synthetic antimicrobial peptide b-34

<400> SEQUENCE: 3

Leu Lys Arg Phe Leu Lys Trp Phe Lys Arg Phe
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic calcium-binding peptide 4DS(P)S
<221> NAME/KEY: MOD_RES
<222> LOCATION: (2)...(11)
<223> OTHER INFORMATION: Xaa = phosphoserine

<400> SEQUENCE: 4

Asp Xaa Ser Asp Xaa Ser Asp Xaa Ser Asp Xaa Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: synthetic calcium-binding peptide with
      non-contiguous subunit repeats interspersed with
      other subunits

<400> SEQUENCE: 5

Asp Ser Ser Asn Ser Ser Asp Ser Ser Asn Ser Ser
1               5                   10

<210> SEQ ID NO 6
<211> LENGTH: 4
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 6

Gly Gly Gly Gly
1

<210> SEQ ID NO 7
<211> LENGTH: 5
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 7

Gly Gly Gly Gly Gly
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 8

Gly Gly Ser Gly Gly Ser
 1               5

<210> SEQ ID NO 9
<211> LENGTH: 5
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 9

Ala Ser Ala Ser Ala
 1               5

<210> SEQ ID NO 10
<211> LENGTH: 5
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 10

Pro Ser Gly Ser Pro
 1               5

<210> SEQ ID NO 11
<211> LENGTH: 5
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 11

Pro Ser Pro Ser Pro
 1               5

<210> SEQ ID NO 12
<211> LENGTH: 5
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 12

Ala Ser Ala Ser Ala
 1               5

<210> SEQ ID NO 13
<211> LENGTH: 5
<212> TYPE: PRT
<213> ORGANISM: Artificial Sequence
<220> FEATURE:
<223> OTHER INFORMATION: synthetic linker peptide joining calcium-
      binding domains
```

```
<400> SEQUENCE: 13

Pro Ser Pro Ser Pro
1               5

<210> SEQ ID NO 14
<211> LENGTH: 4
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 14

Lys Lys Lys Lys
1

<210> SEQ ID NO 15
<211> LENGTH: 4
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 15

Arg Arg Arg Arg
1

<210> SEQ ID NO 16
<211> LENGTH: 5
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 16

Gly Gly Gly Gly Ser
1               5

<210> SEQ ID NO 17
<211> LENGTH: 10
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 17

Gly Gly Gly Gly Ser Gly Gly Gly Gly Ser
1               5                   10

<210> SEQ ID NO 18
<211> LENGTH: 15
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 20
<212> TYPE: PRT
```

<213> ORGANISM: Artificial Sequence
<220> FEATURE:
<223> OTHER INFORMATION: synthetic linker peptide joining calcium-
      binding domains

<400> SEQUENCE: 19

Gly Gly Gly Gly Ser Gly Gly Gly Gly Ser Gly Gly Gly Gly Ser Gly
1               5                   10                  15

Gly Gly Gly Ser
            20

<210> SEQ ID NO 20
<211> LENGTH: 25
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 20

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 21
<211> LENGTH: 30
<212> TYPE: PRT
<213> ORGANISM: Artificial Sequence
<220> FEATURE:
<223> OTHER INFORMATION: synthetic linker peptide joining calcium-
      binding domains

<400> SEQUENCE: 21

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 22
<211> LENGTH: 15
<212> TYPE: PRT
<213> ORGANISM: Artificial Sequence
<220> FEATURE:
<223> OTHER INFORMATION: synthetic calcium-binding peptide 5DSS, (DSS)-5

<400> SEQUENCE: 22

Asp Ser Ser Asp Ser Ser Asp Ser Ser Asp Ser Ser Asp Ser Ser
1               5                   10                  15

<210> SEQ ID NO 23
<211> LENGTH: 22
<212> TYPE: PRT
<213> ORGANISM: Artificial Sequence
<220> FEATURE:
<223> OTHER INFORMATION: synthetic 4DSS-2c4 fusion protein

<400> SEQUENCE: 23

Asp Ser Ser Asp Ser Ser Asp Ser Ser Asp Ser Ser Gly Gly Gly Arg
1               5                   10                  15

Trp Arg Trp Arg Trp Phe
            20

<210> SEQ ID NO 24
<211> LENGTH: 25

```
<212> TYPE: PRT
<213> ORGANISM: Artificial Sequence
<220> FEATURE:
<223> OTHER INFORMATION: synthetic 5DSS-2c4 fusion protein

<400> SEQUENCE: 24

Asp Ser Ser Asp Ser Ser Asp Ser Ser Asp Ser Ser Asp Ser Ser Gly
1               5                   10                  15

Gly Gly Arg Trp Arg Trp Arg Trp Phe
            20                  25

<210> SEQ ID NO 25
<211> LENGTH: 28
<212> TYPE: PRT
<213> ORGANISM: Artificial Sequence
<220> FEATURE:
<223> OTHER INFORMATION: synthetic 6DSS-2c4 fusion protein

<400> SEQUENCE: 25

Asp Ser Ser Asp Ser Ser Asp Ser Ser Asp Ser Ser Asp Ser Ser Asp
1               5                   10                  15

Ser Ser Gly Gly Gly Arg Trp Arg Trp Arg Trp Phe
            20                  25

<210> SEQ ID NO 26
<211> LENGTH: 24
<212> TYPE: PRT
<213> ORGANISM: Artificial Sequence
<220> FEATURE:
<223> OTHER INFORMATION: synthetic calcium-binding peptide 8ASS

<400> SEQUENCE: 26

Ala Ser Ser Ala Ser Ser Ala Ser Ser Ala Ser Ser Ala Ser Ser Ala
1               5                   10                  15

Ser Ser Ala Ser Ser Ala Ser Ser
            20

<210> SEQ ID NO 27
<211> LENGTH: 32
<212> TYPE: PRT
<213> ORGANISM: Artificial Sequence
<220> FEATURE:
<223> OTHER INFORMATION: synthetic 6DSS-b-34 fusion protein

<400> SEQUENCE: 27

Asp Ser Ser Asp Ser Ser Asp Ser Ser Asp Ser Ser Asp Ser Ser Asp
1               5                   10                  15

Ser Ser Gly Gly Gly Leu Lys Arg Phe Leu Lys Trp Phe Lys Arg Phe
            20                  25                  30

<210> SEQ ID NO 28
<211> LENGTH: 21
<212> TYPE: PRT
<213> ORGANISM: Artificial Sequence
<220> FEATURE:
<223> OTHER INFORMATION: synthetic calcium-binding peptide 7DSS

<400> SEQUENCE: 28

Asp Ser Ser Asp Ser Ser Asp Ser Ser Asp Ser Ser Asp Ser Ser Asp
1               5                   10                  15

Ser Ser Asp Ser Ser
            20

<210> SEQ ID NO 29
```

```
<211> LENGTH: 25
<212> TYPE: PRT
<213> ORGANISM: Artificial Sequence
<220> FEATURE:
<223> OTHER INFORMATION: synthetic 5DSS-PL135 fusion protein

<400> SEQUENCE: 29

Asp Ser Ser Asp Ser Ser Asp Ser Ser Asp Ser Ser Asp Ser Ser Gly
1               5                   10                  15

Gly Gly Phe His Phe His Leu His Phe
            20                  25

<210> SEQ ID NO 30
<211> LENGTH: 6
<212> TYPE: PRT
<213> ORGANISM: Artificial Sequence
<220> FEATURE:
<223> OTHER INFORMATION: synthetic calcium-binding peptide 2DSS

<400> SEQUENCE: 30

Asp Ser Ser Asp Ser Ser
1               5

<210> SEQ ID NO 31
<211> LENGTH: 12
<212> TYPE: PRT
<213> ORGANISM: Artificial Sequence
<220> FEATURE:
<223> OTHER INFORMATION: synthetic calcium-binding peptide 4DSS

<400> SEQUENCE: 31

Asp Ser Ser Asp Ser Ser Asp Ser Ser Asp Ser Ser
1               5                   10

<210> SEQ ID NO 32
<211> LENGTH: 18
<212> TYPE: PRT
<213> ORGANISM: Artificial Sequence
<220> FEATURE:
<223> OTHER INFORMATION: synthetic calcium-binding peptide 6DSS

<400> SEQUENCE: 32

Asp Ser Ser Asp Ser Ser Asp Ser Ser Asp Ser Ser Asp Ser Ser Asp
1               5                   10                  15

Ser Ser

<210> SEQ ID NO 33
<211> LENGTH: 24
<212> TYPE: PRT
<213> ORGANISM: Artificial Sequence
<220> FEATURE:
<223> OTHER INFORMATION: synthetic calcium-binding peptide 8DSS

<400> SEQUENCE: 33

Asp Ser Ser Asp Ser Ser Asp Ser Ser Asp Ser Ser Asp Ser Ser Asp
1               5                   10                  15

Ser Ser Asp Ser Ser Asp Ser Ser
            20

<210> SEQ ID NO 34
<211> LENGTH: 12
<212> TYPE: PRT
<213> ORGANISM: Artificial Sequence
<220> FEATURE:
<223> OTHER INFORMATION: synthetic calcium-binding peptide 4ESS
```

```
<400> SEQUENCE: 34

Glu Ser Ser Glu Ser Ser Glu Ser Ser Glu Ser Ser
1               5                   10

<210> SEQ ID NO 35
<211> LENGTH: 12
<212> TYPE: PRT
<213> ORGANISM: Artificial Sequence
<220> FEATURE:
<223> OTHER INFORMATION: synthetic calcium-binding peptide 4NSS

<400> SEQUENCE: 35

Asn Ser Ser Asn Ser Ser Asn Ser Ser Asn Ser Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: synthetic calcium-binding peptide 4DTT

<400> SEQUENCE: 36

Asp Thr Thr Asp Thr Thr Asp Thr Thr Asp Thr Thr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: synthetic calcium-binding peptide 4ETT

<400> SEQUENCE: 37

Glu Thr Thr Glu Thr Thr Glu Thr Thr Glu Thr Thr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: synthetic calcium-binding peptide 4NTT

<400> SEQUENCE: 38

Asn Thr Thr Asn Thr Thr Asn Thr Thr Asn Thr Thr
1               5                   10

<210> SEQ ID NO 39
<211> LENGTH: 24
<212> TYPE: PRT
<213> ORGANISM: Artificial Sequence
<220> FEATURE:
<223> OTHER INFORMATION: synthetic calcium-binding peptide 8DAA

<400> SEQUENCE: 39

Asp Ala Ala Asp Ala Ala Asp Ala Ala Asp Ala Ala Asp Ala Ala Asp
1               5                   10                  15

Ala Ala Asp Ala Ala Asp Ala Ala
            20

<210> SEQ ID NO 40
<211> LENGTH: 24
<212> TYPE: PRT
<213> ORGANISM: Artificial Sequence
<220> FEATURE:
```

<223> OTHER INFORMATION: synthetic calcium-binding peptide 8NAA

<400> SEQUENCE: 40

Asn Ala Ala Asn Ala Ala Asn Ala Ala Asn Ala Ala Asn Ala Ala Asn
1               5                   10                  15

Ala Ala Asn Ala Ala Asn Ala Ala
            20

<210> SEQ ID NO 41
<211> LENGTH: 9
<212> TYPE: PRT
<213> ORGANISM: Artificial Sequence
<220> FEATURE:
<223> OTHER INFORMATION: synthetic peptide #3-1

<400> SEQUENCE: 41

Leu Ile Lys His Ile Leu His Arg Leu
1               5

<210> SEQ ID NO 42
<211> LENGTH: 27
<212> TYPE: PRT
<213> ORGANISM: Artificial Sequence
<220> FEATURE:
<223> OTHER INFORMATION: synthetic calcium-binding peptide 9DSS

<400> SEQUENCE: 42

Asp Ser Ser Asp Ser Ser Asp Ser Ser Asp Ser Ser Asp Ser Ser Asp
1               5                   10                  15

Ser Ser Asp Ser Ser Asp Ser Ser Asp Ser Ser
            20                  25

<210> SEQ ID NO 43
<211> LENGTH: 30
<212> TYPE: PRT
<213> ORGANISM: Artificial Sequence
<220> FEATURE:
<223> OTHER INFORMATION: synthetic calcium-binding peptide 10DSS

<400> SEQUENCE: 43

Asp Ser Ser Asp Ser Ser Asp Ser Ser Asp Ser Ser Asp Ser Ser Asp
1               5                   10                  15

Ser Ser Asp Ser Ser Asp Ser Ser Asp Ser Ser Asp Ser Ser
            20                  25                  30

<210> SEQ ID NO 44
<211> LENGTH: 12
<212> TYPE: PRT
<213> ORGANISM: Artificial Sequence
<220> FEATURE:
<223> OTHER INFORMATION: synthetic calcium-binding peptide 4NAA

<400> SEQUENCE: 44

Asn Ala Ala Asn Ala Ala Asn Ala Ala Asn Ala Ala
1               5                   10